(12) United States Patent
Dixon et al.

(10) Patent No.: US 7,663,023 B2
(45) Date of Patent: Feb. 16, 2010

(54) MODIFICATION OF LIGNIN BIOSYNTHESIS

(75) Inventors: Richard A. Dixon, Ardmore, OK (US); M. S. Srinivasa Reddy, Ardmore, OK (US); Fang Chen, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 186 days.

(21) Appl. No.: 11/189,109

(22) Filed: Jul. 25, 2005

(65) Prior Publication Data

US 2007/0079398 A1    Apr. 5, 2007

Related U.S. Application Data

(60) Provisional application No. 60/590,991, filed on Jul. 24, 2004.

(51) Int. Cl.
*A01H 1/00* (2006.01)
*C12N 15/82* (2006.01)
*C12N 15/87* (2006.01)

(52) U.S. Cl. .................. 800/285; 800/278; 800/286
(58) Field of Classification Search .................. None
See application file for complete search history.

(56) References Cited

U.S. PATENT DOCUMENTS

| | | | | |
|---|---|---|---|---|
| 5,451,514 | A | 9/1995 | Boudet | 435/172.03 |
| 5,850,020 | A | 12/1998 | Bloksberg | 800/205 |
| 5,922,928 | A | 7/1999 | Chang | 800/205 |
| 6,610,908 | B1 | 8/2003 | Chapple | 800/287 |
| 2006/0260011 | A1 | 11/2006 | Carter et al. | 429/231.1 |

FOREIGN PATENT DOCUMENTS

| NZ | 334565 | 8/2000 |
|---|---|---|
| WO | WO 94/23044 | 10/1994 |
| WO | WO 98/03535 | 1/1998 |
| WO | WO 00/22099 | 4/2000 |
| WO | WO 01/73090 | 10/2001 |
| WO | WO 02/14497 | 2/2002 |
| WO | WO 02/20717 | 3/2002 |

OTHER PUBLICATIONS

Jeandet et al. 2002, J. Agric. Food Chem. 50:2731-2741.*
Hoffmann et al. first published online on May 25, 2004, The Plant Cell 16:1446-1465.*
Buhr et al. 2002, The Plant Journal 30:155-163.*
Thomas et al. 2001, The Plant Journal 25(4):417-425.*
Anterola et al., "Trends in lignin modification: a comprehensive analysis of the effects of genetic manipulations/mutations on lignification and vascular integrity," *Phytochemistry*, 61:221-294, 2002.
Franke et al., "Changes in secondary metabolism and deposition of an unusual lignin in the ref8 mutant of arabidopsis," *Plant Journal*, 30:47-59, 2002.
Rae et al., "Antisense suppression of the lignin biosynthetic enzyme, caffeate O-methyltransferase, improves in vitro digestibility of the tropical pasture legume, Stylosanthes humilis," *Australian Journal of Plant Physiology*, 28:289-297, 2001.
Reddy et al., "Targeted down-regulation of cytochrome P450 enzymes for forage quality improvement in alfalfa (*Medicago sativa* L.)," *Proceedings of the National Academy of Sciences of the United States of America*, 202:16573-16578, 2005.
Baucher et al., "Down-regulation of cinnamyl alcohol dehydrogenase in transgenic alfalfa (*Medicago sativa* L.) and the effect on lignin composition and digestibility," *Plant Mol Biol*, 39:437-447, 1999.
Buxton and Russell, "Lignin constituents and cell wall digestibility of grass and legume stems," *Crop Sci*, 28:553-558, 1988.
Casler, "Invitro digestibility of dry matter and cell wall constituents of smooth bromegrass forage," *Crop Sci*, 27:931-934, 1987.
Dixon et al., "Genetic manipulation of lignin and phenylpropanoid compounds involved in interactions with microorganisms," *Rec Adv Phytochem*, 28:153178, 1994.
Franke et al., "The arabidopsis ref8 gene encodes the 3-hydroxylase of phenylpropanoid metabolism," *Plant J.*, 301:33-45, 2002.
Grabber, et al., "Digestion kinetics of parachyma and sclerenchyma cell walls isolated from orchadgrass and switchgrass," *Crop Sci*, 32:806-810, 1992.
Grabber, et al., "P-hydroxyphenyl, guaiacyl, and syringyl lignins have similar inhibitory effects on wall degradability," *J Agric Food Chem*, 45:2530-2532, 1997.
GenBank Accession No. AB035183.1, Jun. 29, 2000.
GenBank Accession No. AB185953.1, Jan. 23, 2008.
GenBank Accession No. AB185954.1, Jan. 23, 2008.
GenBank Accession No. AJ507825.1, Jan. 2, 2003.
GenBank Accession No. AJ555865.1, Jun. 8, 2004.
GenBank Accession No. AJ582651.1, Jun. 10, 2004.
GenBank Accession No. AJ582652.1, Jun. 10, 2004.
GenBank Accession No. AM116757.1, Oct. 21, 2006.
GenBank Accession No. AM283092.1, Dec. 2, 2006.
GenBank Accession No. AY084652.1, Jan. 27, 2006.
GenBank Accession No. BT026488.1, Aug. 2, 2006.
GenBank Accession No. BX830476.1, Feb. 6, 2004.
GenBank Accession No. BX830698.1, Feb. 6, 2004.
GenBank Accession No. BX830912.1, Feb. 6, 2004.
GenBank Accession No. BX831467.1, Feb. 6, 2004.
GenBank Accession No. BX832315.1, Feb. 6, 2004.
GenBank Accession No. BX832778.1, Feb. 6, 2004.
GenBank Accession No. DQ104740.1, Apr. 10, 2007.
GenBank Accession No. EF121452, Jul. 12, 2007.
GenBank Accession No. EF121452.1, Jul. 12, 2007.
GenBank Accession No. EF137954.1, Apr. 22, 2007.
GenBank Accession No. EF143341.1, Apr. 22, 2007.
GenBank Accession No. EF153929.1, Apr. 22, 2007.

(Continued)

*Primary Examiner*—Ashwin Mehta
*Assistant Examiner*—Li Zheng
(74) *Attorney, Agent, or Firm*—Stephen P. Rhines, Esq.; Sonnenschein Nath & Rosenthal LLP

(57) ABSTRACT

The invention provides methods for decreasing lignin content and improving lignin profiles. Also provided are the plants prepared by the methods of the invention. Such plants may exhibit improved digestibility relative to prior plants.

18 Claims, 20 Drawing Sheets

OTHER PUBLICATIONS

GenBank Accession No. EF153930, Apr. 22, 2007.
GenBank Accession No. EF153930.1, Apr. 22, 2007.
GenBank Accession No. EF153931, Apr. 22, 2007.
GenBank Accession No. EF153931.1, Apr. 22, 2007.
GenBank Accession No. EF450248, Dec. 1, 2007.
GenBank Accession No. EU124731.1, Sep. 30, 2007.
GenBank Accession No. NM 124270.3, Apr. 20, 2007.
Medicago Accession No. TC106825, undated.
Klug, "The discovery of zinc fingers and their development for practical applications in gene regulation," *Proc. Japan Acad.*, 81B(4):87-102, 2005.
Usman et al., "Nuclease-resistant synthetic ribozymes: developing a new class of therapeutics," *J. of Clinical Investigation*, 106(10):1197-1202, 2000.
Boudet et al., "Lignins and lignocellulosics: a better control of synthesis for new and improved uses," *TRENDS* in Plant Science, 8(12): 576-581, 2003.
Hoffmann et al., "Purification, Cloning, and Properties of an Acyltransferase Controlling Shikimate and Quinate Ester Intermediates in Phenylpropanoid Metabolism," *J. Biol. Chem.*, 278:95-103, 2003.

* cited by examiner

Down-regulation of 4-coumarate 3-hydroxylase (C3H) in transgenic alfalfa

C, control alfalfa lines
1-20, antisense C3H lines

Lignin composition in transgenic alfalfa transformed with pCAMBIA2200-C3H

| Line # | H/T ratio | S/G ratio | Total (mmol/g) |
|---|---|---|---|
| C1 | 0.03 | 0.55 | 1.05 |
| C2 | 0.02 | 0.49 | 1.12 |
| 1 | 0.21 | 0.64 | 0.57 |
| 2 | 0.03 | 0.39 | 0.94 |
| 3 | 0.48 | 0.48 | 0.22 |
| 4 | 0.55 | 0.48 | 0.28 |
| 5 | 0.37 | 0.67 | 0.60 |
| 6 | 0.02 | 0.44 | 0.96 |
| 7 | 0.42 | 0.77 | 0.48 |
| 8 | 0.40 | 0.84 | 0.38 |
| 9 | 0.02 | 0.46 | 0.82 |
| 13 | 0.02 | 0.42 | 0.96 |
| 14 | 0.29 | 0.50 | 0.54 |
| 15 | 0.02 | 0.45 | 0.82 |
| 16 | 0.32 | 0.60 | 0.45 |
| 19 | 0.20 | 0.61 | 1.01 |
| 20 | 0.01 | 0.51 | 1.09 |

FIG. 5

Down-regulation of cinnamate 4-hydroxylase (C4H) in transgenic alfalfa

| Line # | S/G ratio | Total mmol/g |
|---|---|---|
| C1 | 0.546 | 1.070 |
| 1 | 0.476 | 0.809 |
| 2 | 0.136 | 0.222 |
| 5 | 0.241 | 0.406 |
| 6 | 0.574 | 0.940 |
| 9 | 0.126 | 0.072 |
| 14 | 0.132 | 0.081 |
| 25 | 0.122 | 0.088 |

Lignin composition

C, control alfalfa lines
1-25, antisense C4H lines

Down-regulation of ferulate 5-hydroxylase (F5H) in transgenic alfalfa

C, control alfalfa lines
1-24, antisense F5H lines

HCT & C3H - Alfalfa

MODIFICATION OF LIGNIN BIOSYNTHESIS

This application claims the benefit of U.S. Provisional Patent Application Ser. No. 60/590,991, filed Jul. 24, 2004, the entire contents of which are herein specifically incorporated by reference.

BACKGROUND OF THE INVENTION

1. Field of the Invention

The present invention relates generally to the field of molecular biology. More specifically, the invention relates to modification of lignin biosynthesis.

2. Description of the Related Art

Lignin is the major structural component of secondarily thickened plant cell walls. It is a complex polymer of hydroxylated and methoxylated phenylpropane units, linked via oxidative coupling that is probably catalyzed by both peroxidases and laccases (Boudet, et al., 1995. "Tansley review No. 80: Biochemistry and molecular biology of lignification," *New Phytologist* 129:203-236). Lignin imparts mechanical strength to stems and trunks, and hydrophobicity to water-conducting vascular elements. Although the basic enzymology of lignin biosynthesis is reasonably well understood, the regulatory steps in lignin biosynthesis and deposition remain to be defined (Davin, L. B. and Lewis, N. G. 1992. "Phenylpropanoid metabolism: biosynthesis of monolignols, lignans and neolignans, lignins and suberins," *Rec Adv Phytochem* 26:325-375).

There is considerable interest in the potential for genetic manipulation of lignin levels and/or composition to help improve digestibility of forages and pulping properties of trees (Dixon, et al., 1994. "Genetic manipulation of lignin and phenylpropanoid compounds involved in interactions with microorganisms," *Rec Adv Phytochem* 28:153178; Tabe, et al., 1993. "Genetic engineering of grain and pasture legumes for improved nutritive value," *Genetica* 90:181-200; Whetten, R. and Sederoff, R. 1991. "Genetic engineering of wood," *Forest Ecology and Management* 43:301-316; U.S. Patent Appl. Pub. 2004/0049802.). Small decreases in lignin content have been reported to positively impact the digestibility of forages (Casler, M. D. 1987. "In vitro digestibility of dry matter and cell wall constituents of smooth bromegrass forage," *Crop Sci* 27:931-934). By improving the digestibility of forages, higher profitability can be achieved in cattle and related industries. In forestry, chemical treatments necessary for the removal of lignin from trees are costly and potentially polluting.

Lignins contain three major monomer species, termed p-hydroxyphenyl (H), guaiacyl (G) and syringyl (S), produced by reduction of CoA thioesters of coumaric, ferulic and sinapic acids, respectively. In angiosperms, guaiacyl and syringyl units predominate, and the S/G ratio affects the physical properties of the lignin. The S and G units are linked through five different dimer bonding patterns (Davin, L. B. and Lewis, N. G. 1992. *Rec Adv Phytochem* 26:325-375). The mechanisms that determine the relative proportions of these linkage types in a particular lignin polymer have been unknown. Furthermore, there is considerable debate as to whether lignin composition and structure are tightly controlled, or are flexible depending upon monomer availability (Lewis, N. G. 1999. "A 20th century roller coaster ride: a short account of lignification," *Current Opinion in Plant Biology* 2:153-162; Sederoff, et al., 1999. "Unexpected variation in lignin," *Current Opinion in Plant Biology* 2:145-152).

Lignin levels increase with progressive maturity in stems of forage crops, including legumes such as alfalfa (Jung, H. G. and Vogel, K. P. 1986. "Influence of lignin on digestibility of forage cell wall material," *J Anim Sci* 62:1703-1712) and in grasses such as tall fescue (Buxton, D. R. and Russell, J. R. 1988. "Lignin constituents and cell wall digestibility of grass and legume stems," *Crop Sci* 28:553-558). In addition, lignin composition changes with advanced maturity towards a progressively higher S/G ratio (Buxton, D. R. and Russell, J. R. 1988. *Crop Sci* 28:553-558). Both lignin concentration (Albrecht, et al., 1987. "Cell-wall composition and digestibility of alfalfa stems and leaves," *Crop Sci* 27:735-741; Casler, M. D. 1987. *Crop Sci* 27:931-934; Jung, H. G. and Vogel, K. P. 1986. *J Anim Sci* 62:1703-1712) and lignin methoxyl content, reflecting increased S/G ratio (Sewalt, et al., 1996. "Lignin impact on fiber degradation. 1. Quinone methide intermediates formed from lignin during in vitro fermentation of corn stover," *J Sci Food Agric* 71:195-203), have been reported to negatively correlate with forage digestibility for ruminant animals.

Although a number of studies have linked decreased forage digestibility to increased S/G ratio as a function of increased maturity (Buxton, D. R. and Russell, J. R. 1988. *Crop Sci* 28:553-558; Grabber, et al., 1992. "Digestion kinetics of parenchyma and sclerenchyma cell walls isolated from orchardgrass and switchgrass," *Crop Sci* 32: 806-810), other studies have questioned the effect of lignin composition on digestibility (Grabber, et al., 1997. "p-hydroxyphenyl, guaiacyl, and syringyl lignins have similar inhibitory effects on wall degradability," *J Agric Food Chem* 45:2530-2532). Further, the hardwood gymnosperm lignins are highly condensed, essentially lacking S residues, and this makes them less amenable to chemical pulping, in apparent contradiction to the concept that reducing S/G ratio would be beneficial for forage digestibility. The reported lack of agreement in the relationship of lignin composition to forage digestibility and chemical pulping is partly due to the fact that the studies to date either have been in vitro, or have compared plant materials at different developmental stages, different varieties or even different species. Therefore, the development of isogenic lines that can be directly compared to reveal the effects of altered S/G ratio on forage digestibility would be beneficial.

To date, there have been very few published reports on the genetic modification of lignin in forage crops such as alfalfa, other *Medicago* sp., timothy, bromegrass, white or red clover, fescue, orchardgrass, *Lolium* sp. (e.g. rye grass), and bluegrass among others. Most studies having concentrated on model systems such as *Arabidopsis* and tobacco (Hoffmann et al., 2004), or tree species such a poplar, and thus the effect of such modifications on forage digestibility is unclear.

In one study, down-regulation of cinnamnyl alcohol dehydrogenase, an enzyme later in the monolignol pathway than COMT or CCOMT, led to a small but significant improvement in in vitro dry matter digestibility in transgenic alfalfa (Baucher, et al., 1999. *Plant Mol Biol* 39:437-447). U.S. Pat. No. 5,451,514 discloses a method of altering the content or composition of lignin in a plant by stably incorporating into the genome of the plant a recombinant DNA encoding an mRNA having sequence similarity to cinnamyl alcohol dehydrogenase. U.S. Pat. No. 5,850,020 discloses a method for modulating lignin content or composition by transforming a plant cell with a DNA construct with at least one open reading frame coding for a functional portion of one of several enzymes isolated from *Pinus radiata* (pine) or a sequence having 99% homology to the isolated gene: cinnamate 4-hydroxylase (C4H), coumarate 3-hydroxylase (C3H), phenolase (PNL), O-methyltransferase (OMT), cinnamoyl-CoA reductase (CCR), phenylalanine ammonia-lyase (PAL), 4-coumarate:CoA ligase (4CL), and peroxidase (POX). U.S. Pat. No. 5,922,928 discloses a method of transforming and regenerating *Populus* species to alter the lignin content and composition using an O-methyltransferase gene. U.S. Pat. No. 6,610,908 describes manipulation of lignin composition in plants using a tissue-specific promoter and a sequence encoding a ferulate-5-hydroxylase (F5H) enzyme.

While the foregoing studies have provided a further understanding of the production of plant lignin, there remains a great need in the art for plants with greatly improved digestibility as a result of lignin modification. Development of such plants would have a significant benefit in agriculture, particularly for the production of improved forage crops and more particularly forage legumes.

SUMMARY OF THE INVENTION

In one aspect, the invention provides a transgenic plant or plant cell comprising a selected transgenic DNA, wherein the selected transgenic DNA down regulates a 4-coumarate 3-hydroxylase (C3H) (e.g. SEQ ID NO's 1-2), phenylalanine ammonia-lyase (PAL) (e.g. SEQ ID NO's 3-24), cinnamate 4-hydroxylase (C4H) (e.g. SEQ ID NO's 25-36), hydroxycinnamoyl transferase (HCT) (e.g. SEQ ID NO's 37-38), or ferulate 5-hydroxylase (F5H) (e.g. SEQ ID NO's 39-45) lignin biosynthesis gene. In one embodiment, the selected DNA is an antisense or RNAi construct. In another embodiment, the selected DNA encodes a ribozyme, or zinc-finger protein.

In another embodiment, the transgenic plant or plant cell is a monocot or a dicot, and may be selected from alfalfa, *Arabidopsis thaliana*, barley, cotton, sunflower, loblolly pine, clover, maize, potato, rice, rye, sugarcane, sorghum, soybean, tomato, wheat, *Medicago truncatula*, timothy, bromegrass, white or red clover, fescue, orchardgrass, *Lolium* sp. (e.g. rye grass), and bluegrass. Preferably, the transgenic plant is a legume. More preferably, the transgenic plant or plant cell is a forage legume. Most preferably, the transgenic plant or plant cell is alfalfa.

The transgenic plant or plant cell comprising the antisense or RNAi construct may comprise a promoter selected from the group consisting of a developmentally-regulated, organelle-specific, inducible, tissue-specific, constitutive, cell-specific, seed specific, or germination-specific promoter. The transgenic plant may be further defined as an R0 transgenic plant, or a progeny of an R0 transgenic plant of any generation, wherein the transgenic plant has inherited the selected DNA from the R0 transgenic plant.

In one aspect, at least two lignin biosynthesis genes in the transgenic plant or plant cell comprising the selected DNA are down-regulated. In another aspect, at least three lignin biosynthesis genes are down-regulated. In yet another aspect, at least four lignin biosynthesis genes are down-regulated. In still another aspect, all of the lignin biosynthesis genes are down-regulated.

Another embodiment of the present invention comprises seed of the transgenic plant comprising a selected DNA that down-regulates a 4-coumarate 3-hydroxylase (C3H), phenylalanine ammonia-lyase (PAL), cinnamate 4-hydroxylase (C4H), hydroxycinnamoyl transferase (HCT) or ferulate 5-hydroxylase (F5H) lignin biosynthesis gene, wherein the seed comprises the selected DNA.

In another aspect, the present invention comprises a method of modifying lignin biosynthesis in a plant, comprising transforming a plant with an isolated nucleic acid that encodes all or part of a lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), ferulate 5-hydroxylase (F5H) wherein the down-regulating is accomplished by introduction of an isolated nucleic acid sequence that encodes all or part of at least one of the lignin biosynthesis genes, or its complement. In one embodiment, the isolated nucleic acid sequence is in sense orientation; in another embodiment the isolated nucleic acid is in antisense orientation The isolated nucleic acid may also be in sense and antisense orientation. In still yet another embodiment, the lignin content is decreased in the plant. The present invention also provides a method to decrease the ratio of syringyl monomers to guaiacyl monomers in the plant.

In another aspect, the present invention provides a method to down-regulate lignin biosynthesis in a plant, and comprises introducing into the plant a selected DNA that down regulates the function of at least one of the 4-coumarate 3-hydroxylase (C3H), phenylalanine ammonia-lyase (PAL), cinnamate 4-hydroxylase (C4H), hydroxycinnamoyl transferase (HCT) and ferulate 5-hydroxylase (F5H) lignin biosynthesis enzymes, wherein the down-regulating is accomplished by introduction of an isolated nucleic acid sequence that encodes all or part of at least one of the lignin biosynthesis genes, or its complement. The selected DNA may be an antisense or RNAi construct. The present invention also includes an embodiment wherein the selected DNA encodes a ribozyme or zinc-finger protein that inhibits the expression of the lignin biosynthesis gene. In another embodiment, the isolated nucleic acid sequence is in sense orientation; in yet another embodiment the isolated nucleic acid is in antisense orientation The isolated nucleic acid may also be in sense and antisense orientation. In yet another embodiment, down-regulating a lignin biosynthesis gene may comprise mutating the lignin biosynthesis gene. In a particular embodiment the plant exhibits improved digestibility relative to a plant in which the down-regulating has not been carried out.

In one embodiment of the method of the present invention, introducing into a plant comprises breeding a transgenic plant comprising the isolated nucleic acid with another plant. In another embodiment, introducing the isolated nucleic acid comprises genetic transformation.

Another embodiment of the present invention comprises introducing into the plant a selected DNA that down regulates the function of at least one of the 4-coumarate 3-hydroxylase (C3H), phenylalanine ammonia-lyase (PAL), cinnamate 4-hydroxylase (C4H), hydroxycinnamoyl transferase (HCT) and ferulate 5-hydroxylase (F5H) lignin biosynthesis enzymes, wherein the plant is a monocot or a dicot. More particularly, the plant is selected from the group consisting of: alfalfa (*Medicago sativa*), *Medicago* sp., including *Medicago truncatula, Arabidopsis thaliana*, barley, cotton, sunflower, clover, loblolly pine, maize, potato, rice, rye, sugarcane, sorghum, soybean, tomato, wheat, timothy, smooth bromegrass, white or red clover, fescue, orchardgrass, ryegrass, and bluegrass. The plant may further be defined as a legume. More particularly, the plant is further defined as a forage legume. Even more particularly, the plant is alfalfa.

Another aspect of the present invention comprises a method of making food for human or animal consumption comprising:

(a) obtaining a plant comprising a selected transgene DNA, wherein the selected DNA down regulates a 4-coumarate 3-hydroxylase (C3H), phenylalanine ammonia-lyase (PAL), cinnamate 4-hydroxylase (C4H), hydroxycinnamoyl transferase (HCT) or ferulate 5-hydroxylase (F5H) lignin biosynthesis gene;

(b) growing the plant under plant growth conditions to produce plant tissue from the plant; and (c) preparing food for human or animal consumption from the plant tissue.

More particularly, another embodiment of the method of the present invention for preparing food comprises harvesting the plant tissue. In another embodiment, the food is starch, protein, meal, flour or grain.

Another aspect of the present invention is a method for delaying flowering in an alfalfa plant comprising down-regulating in the plant a 4-coumarate 3-hydroxylase (C3H) lignin biosynthesis gene.

In another aspect, the present invention comprises a method for altering flower color in an alfalfa plant comprising down-regulating in the plant a cinnamate 4-hydroxylase (C4H) lignin biosynthesis gene.

The use of the word "a" or "an" when used in conjunction with the term "comprising" in the claims and/or the specification may mean "one," but it is also consistent with and encompasses the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 5. Shows lignin composition in transgenic alfalfa transformed with antisense C3H construct.

DETAILED DESCRIPTION OF THE INVENTION

The invention overcomes the limitations of the prior art by providing novel methods and compositions for the reduction and improvement of lignin content in plants. The invention is significant in that lignin, while imparting mechanical strength to plant stems and trunks, and hydrophobicity to water conducting vascular elements, negatively impacts digestibility, particularly by grazing animals. A decrease in the total lignin has also been shown to be good for pulping. Improving or decreasing lignin composition could significantly benefit farming practices. For example, annual alfalfa production, which is in wide use for animal feed, is 84 million metric tons, with an estimated worth of $6 billion. An annual $350 million increase in milk/beef production and 2.8 million tons decrease in manure solids produced each year could be realized by improving lignin composition. Improvements in lignin could also yield multi billion dollar savings for the paper industry and dramatic reduction in pollution, as well as savings in the cost of nitrogen fertilizer.

The inventors conducted studies aimed at determining the effects of down-regulating genes involved in lignin biosynthesis, namely 4-coumarate 3-hydroxylase (C3H), phenylalanine ammonia-lyase (PAL), cinnamate 4-hydroxylase (C4H), hydroxycinnamoyl transferase (HCT), ferulate 5-hydroxylase (F5H), specifically in relation to their impact on forage quality and digestibility. Both lignin content and composition, as well as profiles of phenolic compounds, was measured in transgenic plant down-regulated for each of the genes.

Figure 1:
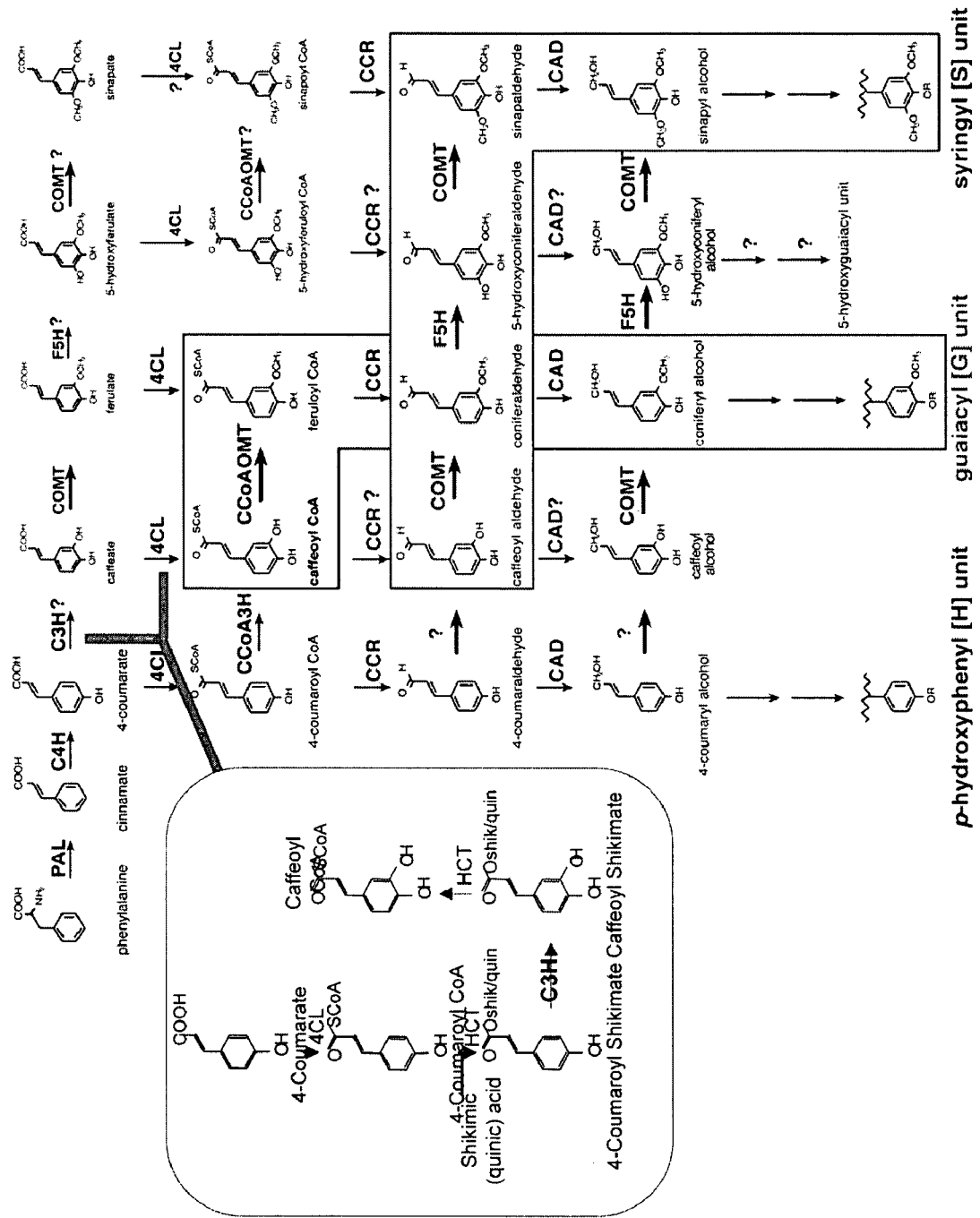
FIG. 1. Shows the lignin biosynthetic pathway.

The lignin pathway starts with the conversion of phenylalanine to cinnamate by phenylalanine ammonia lyase (PAL) (FIG. 1). The second reaction is performed by cinnamate 4-hydroxylase (C4H) which converts cinnamate to 4-coumarate. These two enzymes form the core of the phenylpropanoid pathway including lignin biosynthesis. Other enzymes in the pathway include C3H or 4-coumarate 3-hydroxylase, which converts 4-coumaroyl shikimate or quinate to caffeoyl shikimate or quinate; HCT, hydroxycinnamoyl CoA: hydroxycinnamoyl transferase which acts at two places (FIG. 1): catalyzing the formation of 4-coumaroyl shikimate (or quinate), the substrate for C3H, from 4-Coumaroyl CoA, and also acting in the opposite direction on caffeoyl shikimate (or quinate), to yield caffeoyl CoA.

CCoAOMT converts caffeoyl CoA to feruloyl coA and might also be involved in other reactions. COMT or caffeic acid O-methyl transferase acts on 5-hydroxy coniferaldehyde and converts it into sinapaldehyde. This enzyme also could act on several other substrates in vitro but is not clear if it acts on them in vivo.

Ferulate 5-hydroxylase (F5H) converts coniferaldehyde to 5-hydroxyconiferaldehyde.

Monomethylated guaiacyl units derived from coniferyl alcohol and dimethylated syringyl units derived from sinapyl alcohol are the major monolignols in alfalfa and other angiosperms. In addition p-hydroxyphenyl units are also present in trace amounts. These monolignols can be designated as H lignin, G lignin and S lignin. These may be analyzed by H/T and S/G ratio where T represents total lignin content. Since the H lignin is in trace amounts, H/T ratios are usually very low in alfalfa, around 0.02 to 0.04. Similarly, the S/G ratio is around 0.5 and changes (increases) as the stem matures.

S/G ratio has been negatively correlated with digestibility but there are contradictory reports available as well. Lignin composition changes with advanced maturity towards a progressively higher S/G ratio. Higher G lignin is not good for pulping. For example the softwood gymnosperms essentially lack S lignin units and are less amenable for pulping compared to angiosperm lignin. Observations of pulping efficiency parameters had suggested that an increase in S/G lignin ratio is important for improving chemical degradability of lignin. The present results indicate that the paper pulping model does not apply to digestion of cell wall material by rumen microorganisms, since there was no relationship between S/G ratio and digestibility. In contrast, total lignin content was highly correlated with digestibility, and is shown here to be the forage quality parameter most affecting digestibility.

Antisense constructs for down-regulating each of C3H, PAL, C4H, HCT and F5H were introduced into alfalfa and selected using kanamycin as a selectable marker. Lignin compositional changes were observed in all the down-regulated lines. For example the C3H and HCT down-regulated lines showed similar lignin compositional changes which were basically an increase in the H/Total lignin ratio and decrease in the lignin content. Phenotypic changes were also observed. The results demonstrate the effectiveness of the invention in improving lignin composition in an economically important forage legume.

In accordance with the invention, down-regulation of lignin biosynthesis genes may be used to decrease lignin content and alter lignin composition to improve digestibility and other characteristics. For example, by introducing an antisense, RNAi or other desired coding sequence to down-regulate a lignin biosynthesis gene as described herein, improvements in digestibility may be obtained. In one embodiment of the invention plant transformation constructs are provided encoding one or more lignin biosynthesis coding sequence. Such lignin biosynthesis genes are known and may be from, for example, alfalfa, barley, sunflower, loblolly pine, maize, potato, rice, rye, sugarcane, sorghum, soybean, tomato, wheat and *Medicago truncatula*. One embodiment of the invention' therefore provides a recombinant vector comprising an antisense or RNAi construct comprising sequences homologous to one or more lignin biosynthesis gene selected from C3H, PAL, C4H, HCT and F5H, including all possible combination thereof, as well as plants transformed with these sequences. Also provided by the invention are nucleic acids encoding the polypeptides encoded by these sequences.

Sequences that hybridize to any of these sequences under stringent conditions may be used. An example of such conditions is 5×SSC, 50% formamide and 42° C. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Nucleic acids provided by the invention include those comprising fragments of lignin biosynthesis genes in sense and/or antisense orientation. Those of skill in the art will immediately understand in view of the disclosure that such fragments may readily be prepared by placing fragments of lignin biosynthesis coding sequences in frame in an appropriate expression vector, for example, comprising a plant promoter. Using the methods described in the working examples, lignin biosynthesis activity and down-regulation can be efficiently confirmed for any given fragment. Fragments of nucleic acids may be prepared according to any of the well known techniques including partial or complete restriction digests and manual shearing.

Nucleic acid sequences may be provided operably linked to a heterologous promoter, in sense or antisense orientation. Expression constructs are also provided comprising these sequences, including antisense and RNAi oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with constructs comprising sequences homologous to lignin biosynthesis coding sequences, for example, one or more of C3H, PAL, C4H, HCT and F5H. Nucleic acids encoding C3H, PAL, C4H, HCT and F5H are known in the art and are disclosed in, for example, U.S. Pat. No. 5,850,020, the entire disclosure of which is specifically incorporated herein by reference.

These sequences may be provided with other sequences for efficient expression as is known in the art. One or more selectable marker genes may be co-introduced into a plant with a nucleic acid provided by the invention. The choice of any additional elements used in conjunction with a sequence will often depend on the purpose of the transformation. One of the major purposes of transformation of crop plants is to add commercially desirable, agronomically important traits to the plant, as described above.

I. Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference). In one embodiment of the invention, the native promoter of a lignin biosynthesis coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that lignin biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence is used. Alternatively, a heterologous 3' end may enhance the expression of sense or antisense lignin biosynthesis coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from Klebsiella ozaenae which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from Streptomyces hygroscopicus or the pat gene from Streptomyces viridochromogenes. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Antisense and RNAi Constructs

Antisense and RNAi treatments represent one way of altering lignin biosynthesis activity in accordance with the invention. In particular, constructs comprising a lignin biosynthesis coding sequence, including fragments thereof, in antisense orientation, or combinations of sense and antisense orientation, may be used to decrease or effectively eliminate the expression of a lignin biosynthesis gene in a plant and obtain an improvement in lignin profile as is described herein. Accordingly, this may be used to "knock-out" the function of a lignin biosynthesis coding sequence or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs will include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those, plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

IV. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et at., 1973). Synthetic PPT, the active ingredient in the herbicide LIBERTY also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces* viridochromogenes. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification.

Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Creation of Transgenic Alfalfa Plants with Modified Lignin Composition

Figure 2:
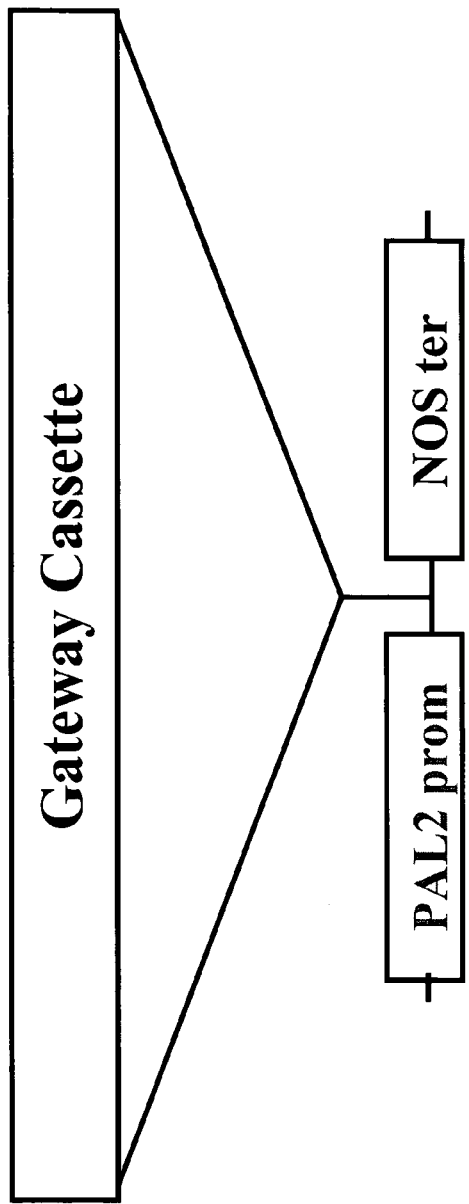
FIG. 2 Shows a vector used for construction of antisense transformation vectors.

Antisense constructs were prepared using the base pCAMBIA2200-GW construct shown in FIG. 2. Constructs were prepared for down-regulation of each of the *Medicago* C3H, PAL, C4H, HCT and F5H coding sequences. The vector was modified by introducing a gene cassette with a pal2 promoter and Nos terminator followed by cloning of the gene of interest in antisense orientation by recombination using the GATEWAY technology.

The *M. truncatula* C3H, C4H and HCT sequences and *Medicago* PAL and F5H sequences were used. The antisense sequence corresponded to the coding portion of the cDNA. The constructs were each transformed into alfalfa (*Medicago sativa*) using the leaf-disk method and selected on kanamycin.

Figure 3:
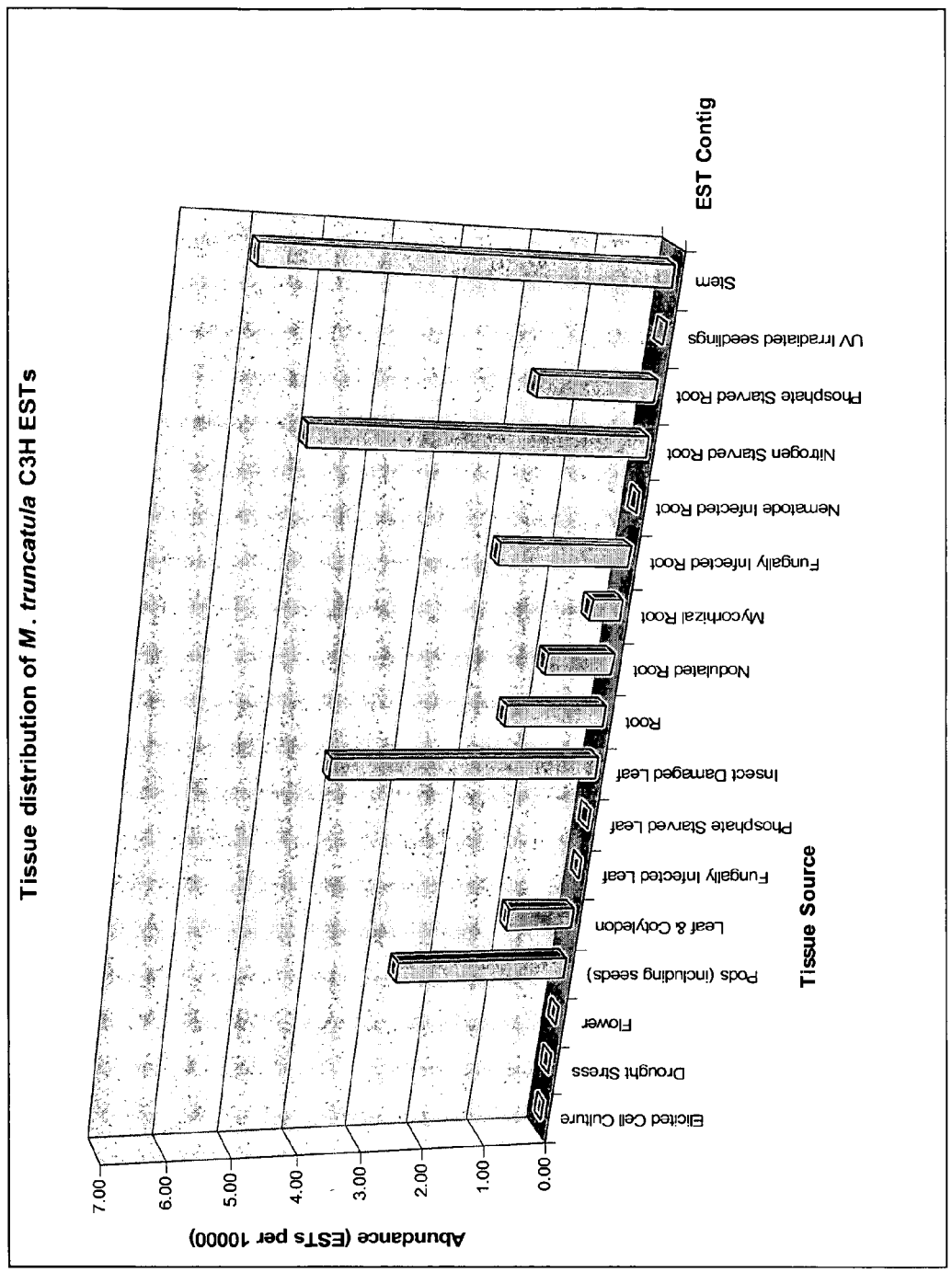
FIG. 3 Shows distribution of C3H ESTs in *M. truncatula*.

As an extensive collection of EST libraries of *Medicago truncatula* are available at the Noble Foundation, and since *M. truncatula* genes are very similar to alfalfa genes in their coding regions, it was chosen to exploit the information available from the *M. truncatula* database for this work (see FIG. 3). C3H had only one tissue contig or TC in *M. truncatula*-TC77383 (SEQ ID NO:1). It was used in the antisense orientation under control of the vascular tissue-specific bean PAL2 promoter to transform alfalfa, and the down-regulated lines were selected.

A. Down-regulation of 4-coumarate 3-hydroxylase (C3H) in Transgenic Alfalfa

Figure 4:
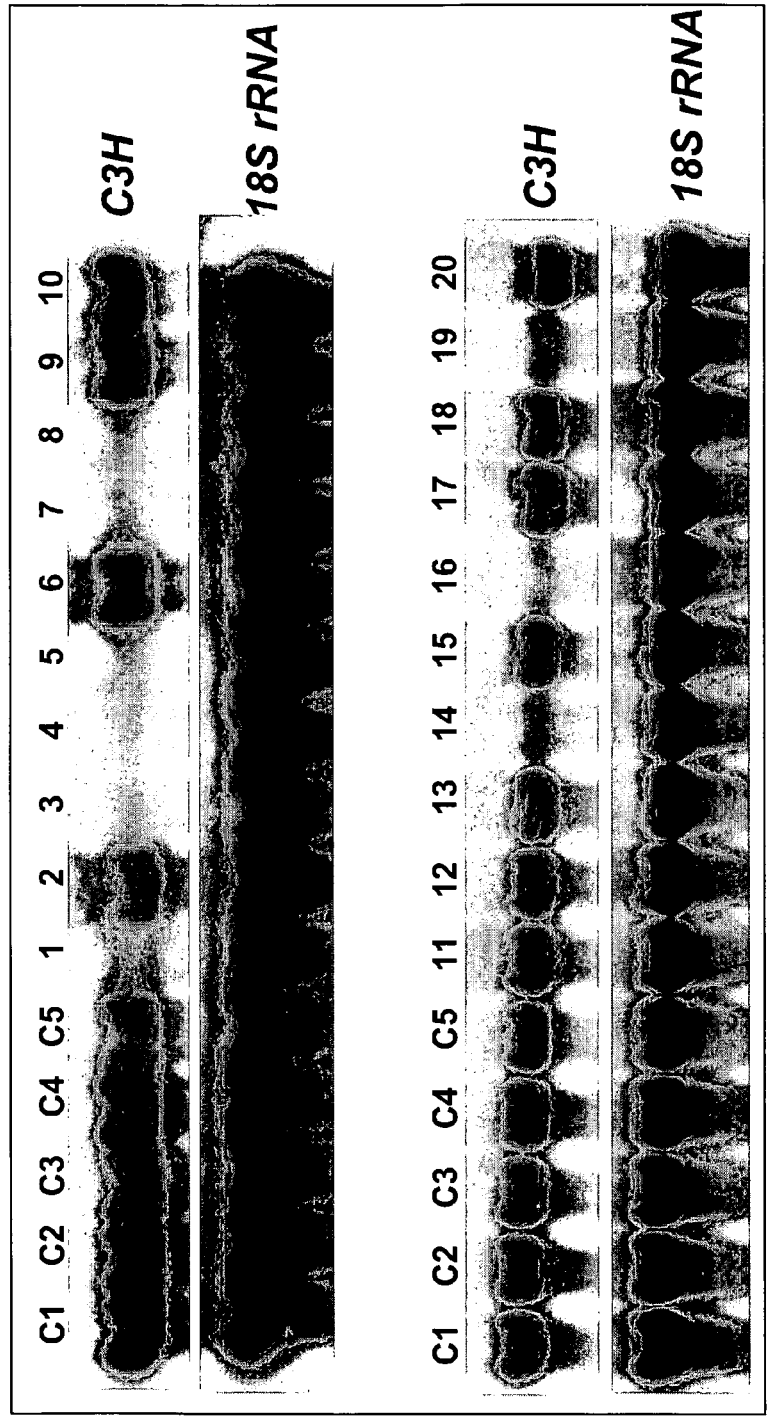
FIG. 4. Shows northern blot of down-regulated C3H in transgenic alfalfa.

Northern blot analysis of transgenic alfalfa transformed with the p-coumarate 3-hydroxylase (C3H) coding region in the antisense orientation (SEQ ID NO:1) was carried out with the C3H coding region and 18S rRNA as probes. The strategy was to get at least 5 down-regulated lines for each construct. About 40 transgenic lines were screened yielding 11 C3H downregulated lines. Some of these lines are shown in FIG. 4. Untransformed or vector transformed alfalfa lines were used as controls.

The lignin composition of the lines was analyzed, showing that C3H downregulated lines had a very high H/T lignin ratio, which went up from 0.03 to as much as 0.55 in some of these lines (FIG. 5). All show higher H/T lignin ratio and also a decrease in the total lignin compared to the total in the control lines. The S/G ratio also tended to increase in these lines. At the beginning of the study itself, it was believed that C3H down-regulation should block the pathway towards the G and S lignin biosynthesis; thus C3H down-regulation would result in a higher H/T lignin ratio.

Figure 12:
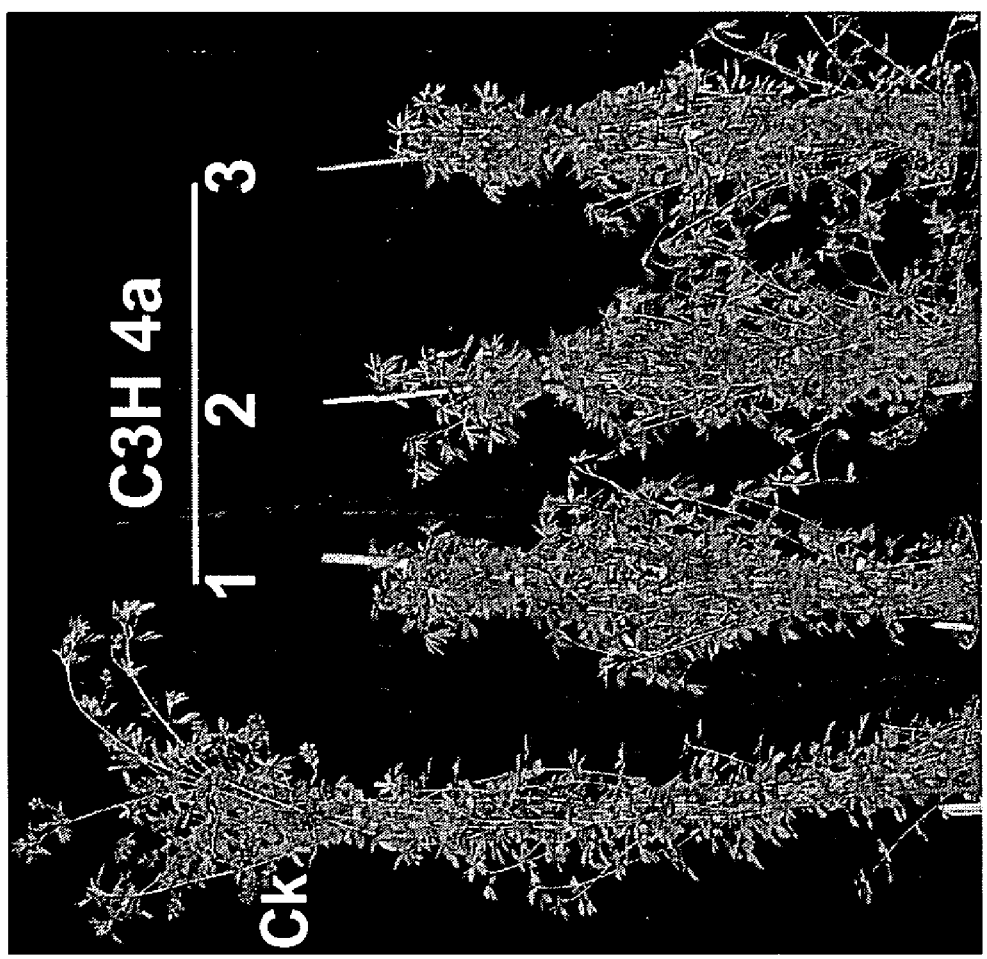
FIG. 12. Shows growth of control line and transgenic alfalfa plant lines expressing an antisense C3H construct.

Phenotypic variations were also seen in a few of the lines, with some, but not all, of the down regulated lines being shorter than the control lines as seen in FIG. 12. Plants with less than approximately 15% of wild-type C3H activity appeared smaller than corresponding vector control lines (FIG. 12).

B. Down-regulation of Phenylalanine Ammonia-lyase (PAL) in Transgenic Alfalfa

Figure 6:
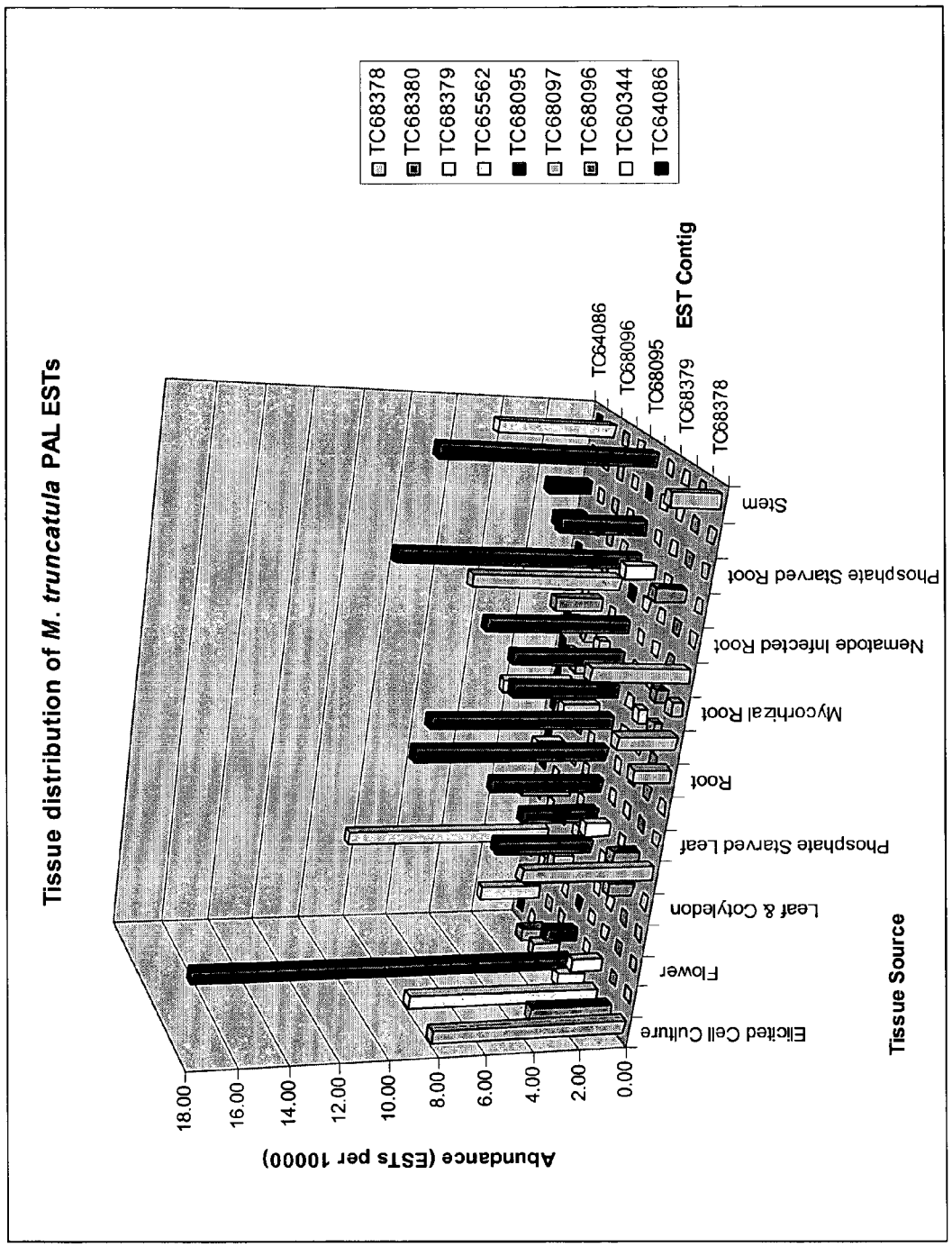
FIG. 6. Shows distribution of PAL ESTs in *M. truncatula*.

PAL is the first enzyme in the lignin biosynthetic pathway. In *M. truncatula*, there are nine TCs corresponding to the PAL gene (FIG. 6). Three of them express in stem. One, TC68095 (SEQ ID NO:8), was selected for antisense mediated downregulation of PAL.

Four PAL downregulated lines representing four independent transgenic events were obtained, of which two showed the dwarf phenotype, which was expected since down-regulation of PAL will affect the entire phenylpropanoid pathway.

Figure 7:
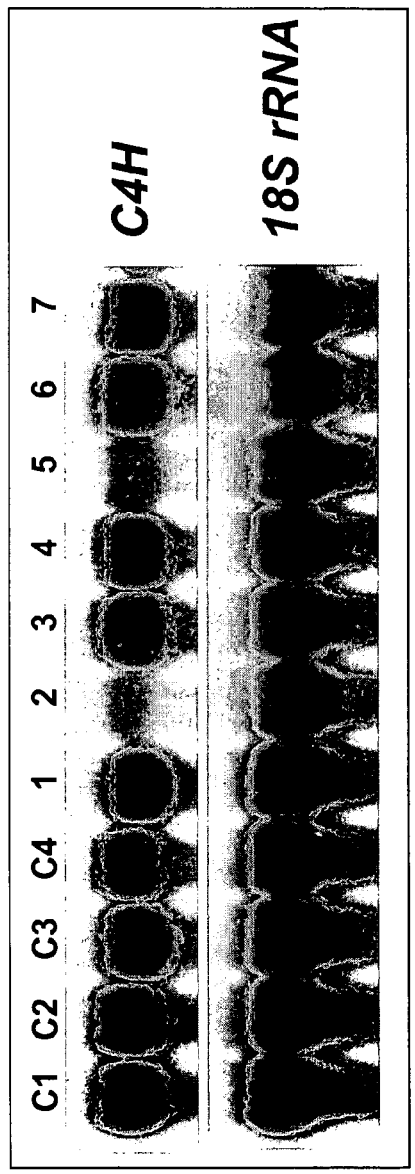
FIG. 7. Shows northern blot and lignin composition for alfalfa transformed with antisense C4H construct.
Figure 13:
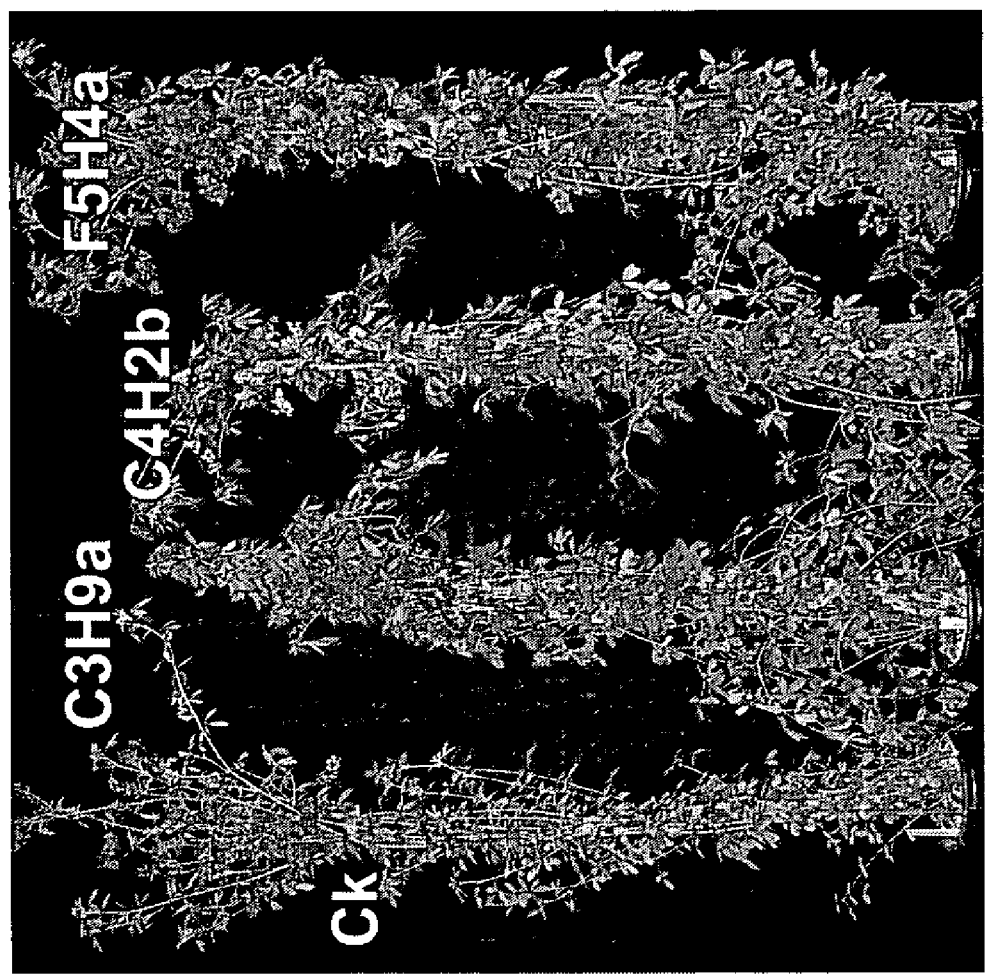
FIG. 13. Shows growth of control line and transgenic alfalfa lines expressing antisense C4H and F5H constructs.

C. Down-regulation of Cinnamate 4-hydroxylase (C4H) in Transgenic Alfalfa 34 transgenic lines have been screened and five independent lines obtained containing TC76780 (SEQ ID NO:25) in the antisense orientation under the control of the vascular-tissue specific bean PAL2 promoter, and down regulated for C4H. The lignin composition of these downregulated lines showed a decrease in the syringyl/guaiacyl monomer ratio, and there was also a decrease in the total lignin compared to control lines (representative data shown in FIG. 7). A representative plant is shown in FIG. 13.

Figure 8:
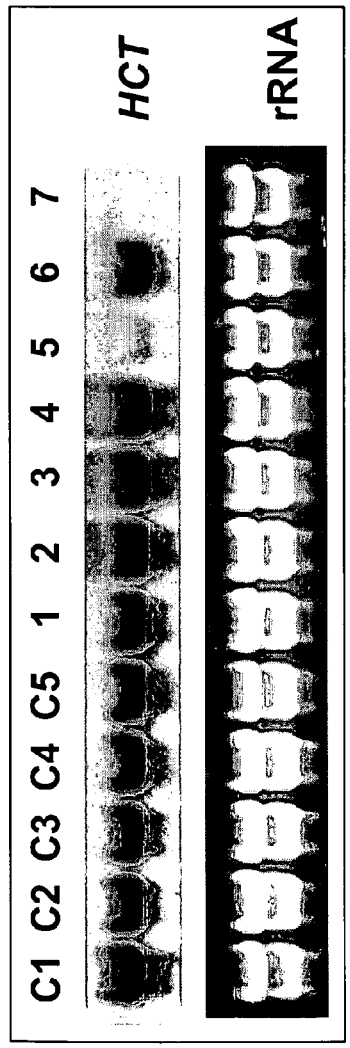
FIG. 8. Shows northern blot and lignin composition for alfalfa transformed with antisense HCT construct.

D. Down-regulation of Hydroxycinnamoyl Transferase (HCT) in Transgenic Alfalfa 7 antisense hydroxycinnamoyl transferase (HCT) transgenic lines were screened, comprising a *Medicago* HCT transgene (e.g. SEQ ID NO:37), yielding two downregulated lines, which are shown in the northern blot in FIG. 8. The ribosomal rRNA shows that the amount of RNA loaded was more or less equal in all the lanes.

Figure 20:
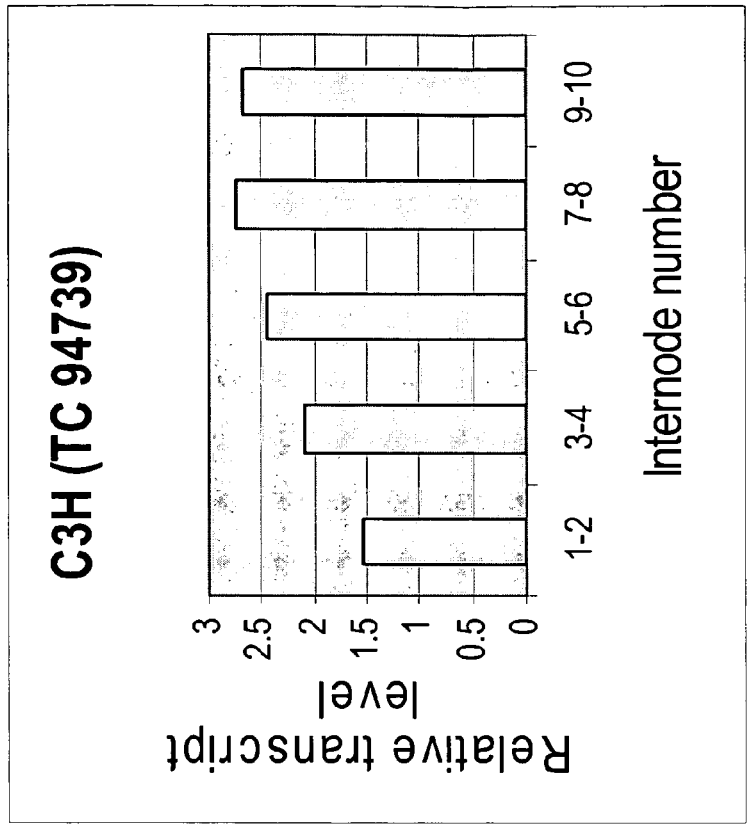
Figure 20:
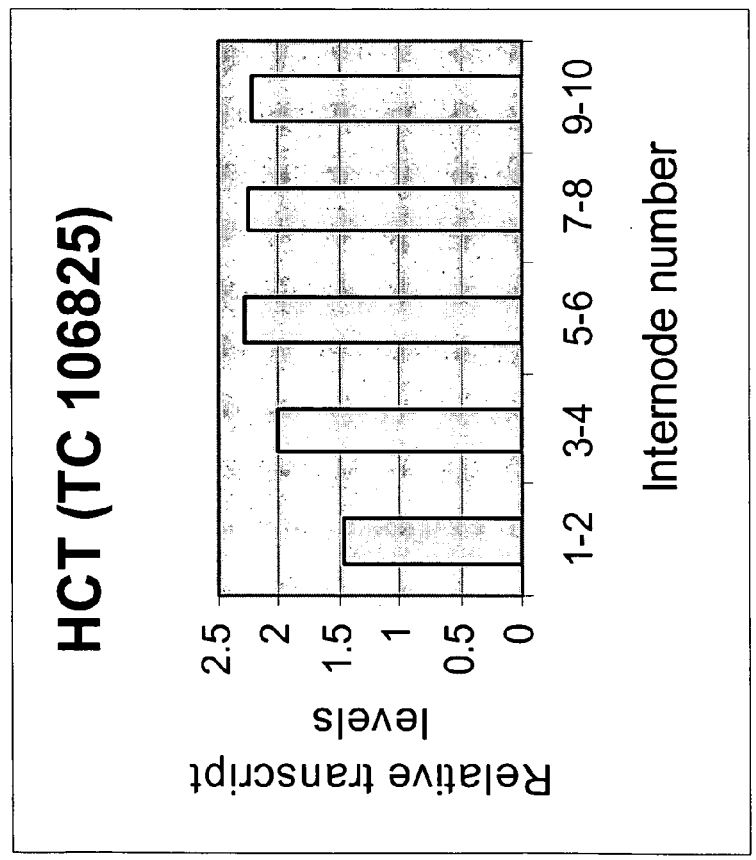

Lignin composition of the HCT lines showed a decrease in total lignin and an increase in the H/T lignin ratio, which was as high as 0.65 in line # 7. S/G lignin ratio increased in these downregulated lines compared to the controls. This was a similar lignin compositional change as that obtained for C3H. That is likely due to the close proximity of the two enzymes in the lignin pathway, in which the product of the C3H reaction is the substrate for HCT. Some of these lines showed a dwarf phenotype, similar to what was observed in C3H downregulated lines. C3H and HCT demonstrate similar expression patterns during different developmental stages of the stem in alfalfa (FIG. 20). Since the down-regulation of C3H and HCT gives similar changes in lignin content and composition, and C3H down-regulation results in increased digestibility, HCT down-regulation also is expected to give a similar if not better increase in digestibility.

E. Down-regulation of Ferulate 5-hydroxylase (F5H) in Transgenic Alfalfa

Figure 9:
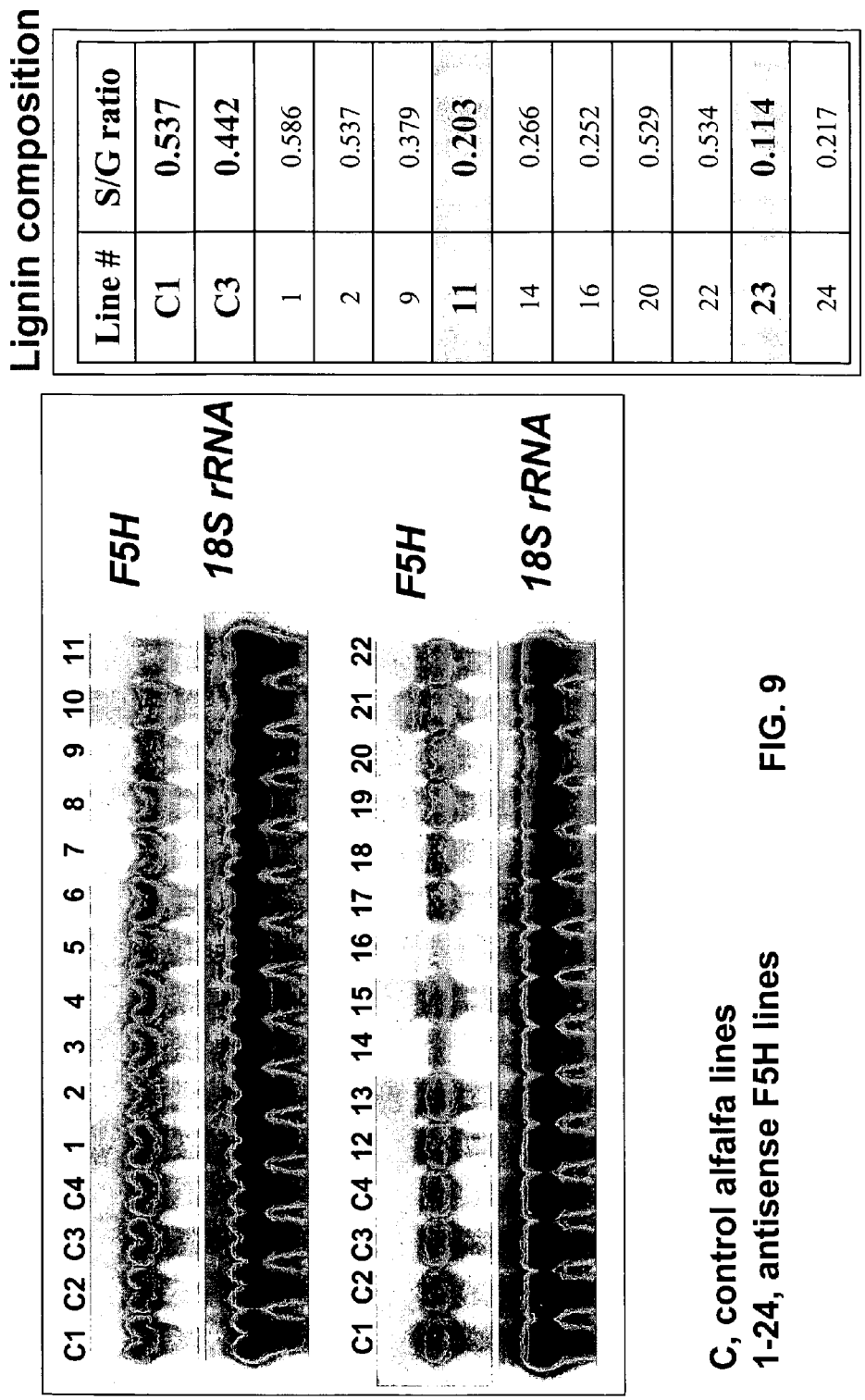
FIG. 9. Shows northern blot and lignin composition for alfalfa transformed with antisense F5H construct.

F5H sequences were isolated by screening an alfalfa stem cDNA library, and cloned in antisense orientation for introduction to alfalfa (e.g. SEQ ID NO:39-41). More than 30 transgenic lines were screened yielding five F5H downregulated lines representing five independent transgenic events. Four of the five lines are shown in the northern blots (FIG. 9). Lignin analysis showed that there was a decreased syringyl/guaiacyl monomer ratio in these F5H downregulated lines. A representative plant is shown in FIG. 13.

Example 2

Phenolic Profiling of Transgenic Plants

Figure 10:
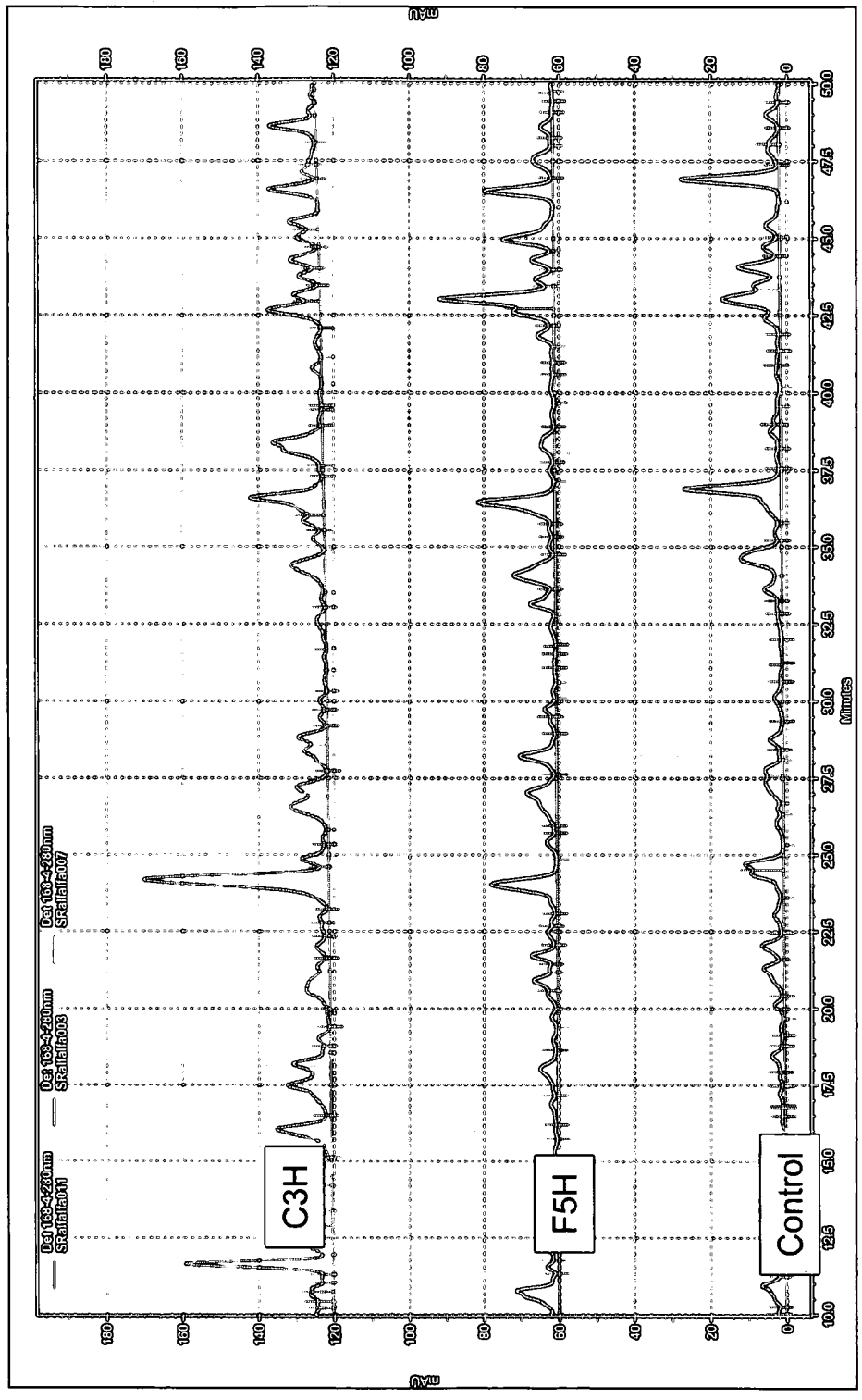
FIG. 10. Shows phenolic profiles of transgenic alfalfa plants.

Once the transgenic lines were screened for change in lignin composition, an analysis was carried out of phenolic profiles. FIG. 10 shows the soluble phenolic profiles of C3H and F5H downregulated lines compared to control. Even though there seemed to be several changes in the quality and size of the peaks, so far they have not been qualitatively identified.

Figure 11:
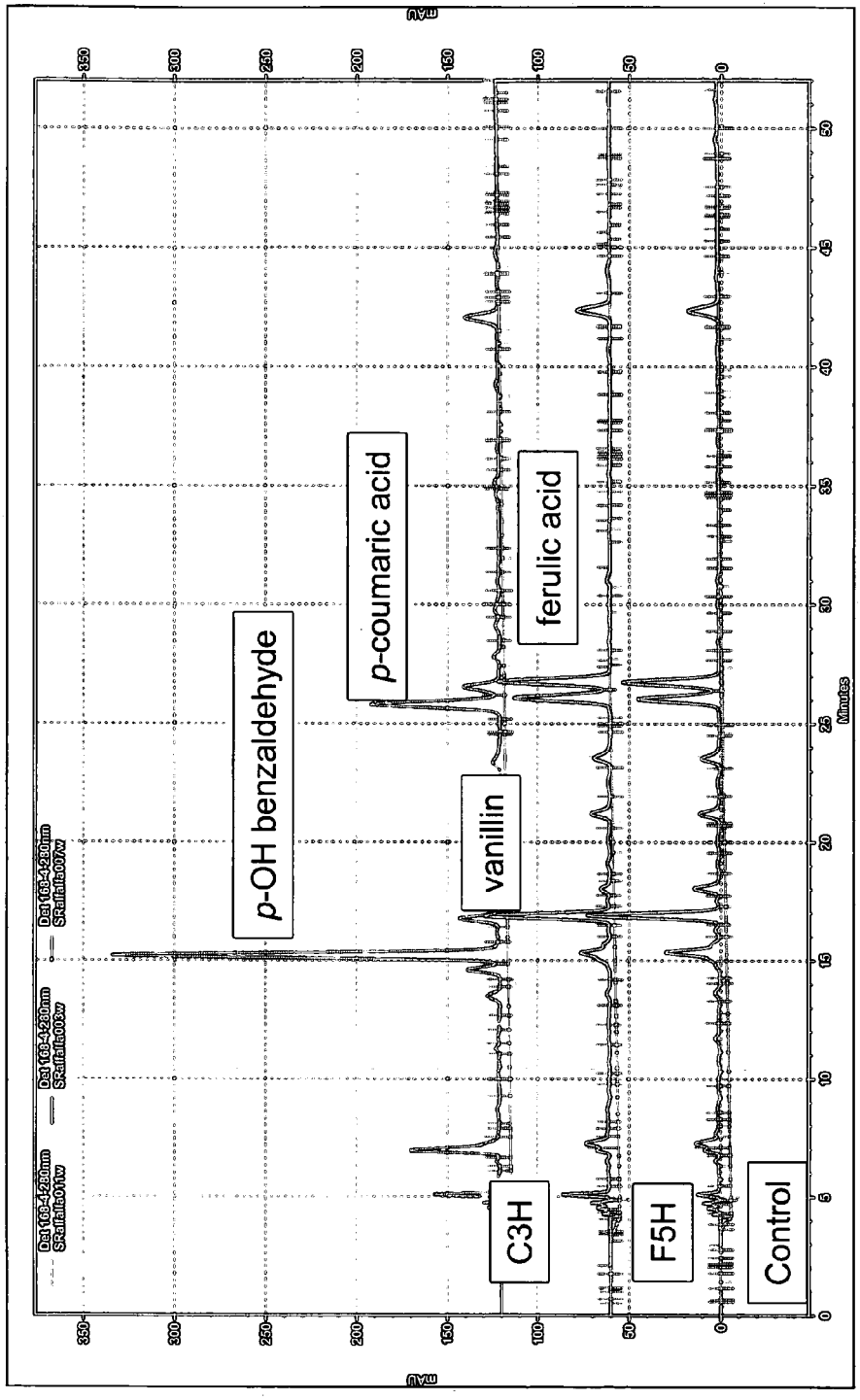
FIG. 11. Shows wall bound phenolic profiles of transgenic alfalfa plants.

FIG. 11 shows the profile of the wall bound phenolics of C3H and F5H downregulated lines compared to the control. As can be seen there is an increase in p-OH benzaldehyde and a decrease in vanillin in C3H downregulated line. There is little change in p-coumaric acid between the control and transgenic lines, but wall-bound ferulic acid levels are reduced in C3H transgenic lines. This may play an important role in increasing digestibility of forage grasses, where ferulate cross-linking of lignin to cell wall polysaccharides may inhibit digestibility. The F5H downregulated line changed little in the profile of wall bound phenolics.

Example 3

Phenotypes of Lignin-modified Alfalfa

In addition to the dwarf phenotype noted above, additional phenotypes seen in some lines included change in flower color, delayed flowering; change in floral scent (in C4H down-regulated lines), and, in some lines such as a C3H line and a F5H line, increase in biomass at the flowering stage. In general, only those lines with the highest level of C3H down-regulation showed delayed growth. Thus, it is possible to produce alfalfa plants with strongly down-regulated C3H activity that develop normally but still show striking changes in lignification, a conclusion not apparent from the phenotype of the previously reported *Arabidopsis* ref8 mutant which lacks C3H activity and exhibits extreme dwarfism (Franke et al. 2002).

Example 4

Forage Quality of Lignin-modified Alfalfa

In vitro and in situ studies were performed to assess changes in digestibility of forage derived from transgenic lines exhibiting down-regulation of lignin biosynthetic enzymes. Total forage samples (leaf plus stem) from internodes 1-5 were harvested from each down-regulated line at the first bud stage. Lignin content was estimated by the acetyl bromide procedure and by total thioacidolysis yield. Thioacidolysis also provided estimates of monomer abundance, expressed as H/T(total), G/T, S/T and S/G ratios. Acetyl bromide lignin levels of forage samples were significantly reduced in C4H and C3H down-regulated lines, but not in F5H down-regulated lines (Table 1).

TABLE 1

Lignin content and composition of control and transgenic alfalfa (leaf plus stem) down-regulated in C4H, C3H or F5H.

| Plant line | Acetyl bromide lignin (g/g dry wt) | Thioacidolysis yield (μmol/g dry wt) | H/T | G/T | S/T | S/G |
|---|---|---|---|---|---|---|
| C4H (n = 2) | 0.06 ± 0.01 | 20.32 ± 21.96 | 0.04 ± 0.01 | 0.80 ± 0.02 | 0.16 ± 0.02 | 0.20 ± 0.03 |
| C3H (n = 6) | 0.07 ± 0.01 | 54.05 ± 35.63 | 0.48 ± 0.06 | 0.32 ± 0.04 | 0.20 ± 0.02 | 0.62 ± 0.05 |
| F5H (n = 2) | 0.10 ± 0.02 | 169.81 ± 24.20 | 0.03 ± 0.00 | 0.80 ± 0.04 | 0.17 ± 0.04 | 0.21 ± 0.05 |
| Control (n = 6) | 0.10 ± 0.01 | 149.32 ± 16.74 | 0.03 ± 0.01 | 0.63 ± 0.02 | 0.30 ± 0.05 | 0.47 ± 0.07 |

These results were reflected in the corresponding total thioacidolysis yields, although much greater effects were seen on total thioacidolysis yield than on acetyl bromide lignin, and striking differences were observed in the thioacidolysis yields of the individual H, G and S monomers. Thus, down-regulation of C4H resulted in a relative increase in the ratio of G to total units at the expense of S units, with a resultant drop in S/G ratio. A very similar pattern was seen for the F5H down-regulated lines, although total thioacidolysis yield was considerably higher. C4H and F5H down-regulation therefore have different effects on lignin content but cause similar changes in overall lignin composition in alfalfa. In contrast, down-regulation of C3H resulted in a massive increase in the proportion of H units in the lignin, and a significant decrease in the ratio of G to total units.

The same samples were analyzed for cell wall polysaccharide composition (Table 2). The levels of hemicellulose were somewhat reduced in the C3H lines, but α-cellulose (cellulose plus lignin) was relatively constant in control and transgenic lines. Pectin levels were reduced in all transgenic lines, although this was not significant at the sample size used. The constant α-cellulose level in plants with reduced lignin levels suggests compensatory cellulose accumulation, as reported previously in poplar plants down-regulated in 4CL (Hu et al., 1999).

TABLE 2

Cell wall polysaccharide composition of control and transgenic alfalfa (leaf plus stem) down-regulated in C4H, C3H or F5H.

| Plant line | Pectin (% dry wt) | Hemicellulose (% dry wt) | α-Cellulose (% dry wt) |
|---|---|---|---|
| C4H (n = 2) | 19.84 ± 3.79 | 39.08 ± 5.28 | 55.68 ± 4.02 |
| C3H (n = 6) | 19.21 ± 4.99 | 31.36 ± 1.93 | 56.17 ± 3.14 |
| F5H (n = 2) | 20.71 ± 5.77 | 36.38 ± 2.20 | 60.09 ± 7.18 |
| Control (n = 6) | 25.47 ± 4.32 | 35.28 ± 3.60 | 55.87 ± 2.39 |

Forage quality analysis was performed on stem material from the most highly down-regulated lines (Table 3), and on previously generated lines down-regulated in caffeic acid 3-O-methyltransferase (COMT), caffeoyl CoA 3-O-methyltransferase (CCoAOMT), or both enzymes. Vegetatively propagated cuttings of transgenic alfalfa (15 plants per line) were grown in one gallon pots in the greenhouse. Aerial portions were harvested at the early bud stage, and dried in a 50° oven for at least 72 hours. The samples were then ground in a Thomas-Wiley model 4 Laboratory Mill (Lehman Scientific, Wrightsville, Pa.) with 1 mm sieves. Acid detergent fiber (ADF) and neutral detergent fiber (NDF) were estimated with a few modifications to standard protocols (Goering et al. (1970). For NDF analysis, 0.35 g of ground samples were transferred to a F57 ANKOM filter bag (ANKOM Technology Corporation, Fairport, N.Y.) and heated at 100° C. for 1 h in an ANKOM Fiber Analyzer, according to the manufacturer's instructions. The samples were washed in near boiling water, dried at 105° C. for 6 h, and weighed to determine fiber loss. ADF was estimated sequentially on the material remaining after NDF analysis. The left-over residue was then used for determination of acid detergent lignin (ADL) by incubation in 72% (v/v) sulfuric acid for 3 h, washing thoroughly and drying at 105° C. for 6 h, prior to weighing.

TABLE 3

Forage quality analysis of individual plants. In addition to lines down-regulated in C3H, C4H and F5H, additional lines down-regulated in COMT (C1-4) or CCoAOMT (CC2-305) were included. The lower set of 3 independent C3H lines and empty vector control were grown together at a different time from the set of six lines above.

| Plant line | IVDMD[a] | ADF[a] | NDF[a] | ADL[a] |
|---|---|---|---|---|
| C3H 4a | 84.10 | 49.62 | 60.52 | 6.52 |
| C4 H 2b | 78.0 | 52.99 | 65.42 | 7.28 |
| F5 H 4a | 54.80 | 57.77 | 68.70 | 13.34 |
| C1-4 | 66.94 | 49.42 | 59.61 | 9.84 |
| CC2-305 | 66.62 | 52.48 | 64.71 | 8.67 |
| CK 48 | 56.26 | 59.07 | 69.60 | 11.92 |
| C3H 4a | 82.13 | 52.90 | 64.46 | 7.49 |
| C3H 5a | 77.98 | 55.39 | 67.82 | 8.70 |
| C3H 9a | 75.93 | 56.72 | 68.93 | 8.70 |
| CK 48 | 49.18 | 61.31 | 72.58 | 13.42 |

[a]All parameters are expressed per g dry weight.

Down-regulation of COMT results in a strikingly reduced S/G ratio, whereas down-regulation of CCoAOMT reduces G lignin but not S lignin in alfalfa (Guo et al., 2000). Acid detergent fiber (ADF) and neutral detergent fiber (NDF) were slightly reduced in all transgenic as compared to control lines. More striking differences were observed for acid detergent lignin (ADL) levels, which mirrored the lignin values obtained by the acetyl bromide and thioacidolysis approaches. ADL was not reduced in the F5H down-regulated line #4a. The COMT (C1-4) and CCoAOMT (CC2-305) lines showed increased digestibility relative to controls as described previously (Guo 2001).

Example 5

Forage Digestibility and the Relationship with Lignin Content and Composition For in vitro digestibility studies, ground alfalfa tissue samples were dried at 105° C. for 6 h prior to weighing to obtain pre-extraction dry weights (0.5 g). The same procedure was also used to obtain post-extraction dry weights. Digestibility analysis was performed using F57 filter bags and the DAISY II incubator (ANKOM Technology Corporation, Fairport, N.Y.) (Vogel et al., 1999), following the manufacturer's instructions.

Analysis of in vitro dry matter digestibility revealed a striking increase in the C4H and C3H lines, an intermediate increase in the COMT and CCoAOMT lines, but no increase in the F5H line (Table 3). To better pursue the lignin-digestibility relationship, replicate cuttings of individual C4H, C3H, COMT, CCoAOMT and F5H lines, plus corresponding controls, were grown in the greenhouse to maturity (first bud stage) in order to generate sufficient forage material for in situ digestibility measurements using fistulated steers. In these studies, Five grams of ground, dried alfalfa tissue was put into each pre-weighed ANKOM rumen in situ filter bag (10×20 cm, pore size=50 um). These bags were then placed in a Mainstays mesh utility bag (60.96×91.44 cm; Pro-Mart Industries, Inc., Rancho Cucamonga, Calif.) and then placed into the rumens of fistulated steers for 12 h, 24 h, 36 h and 72 h of digestion. The five steers were placed on ad libitum alfalfa hay while pastured in small traps with a low volume forage base of volunteer winter annuals and dormant bermuda grass for two weeks prior to the trials. During the trials, they were fed only alfalfa. Each sample was in duplicate for each time point in each of the steers. The bags were removed from the rumen, thoroughly washed in a commercial washing machine, and freeze dried. Digestibility was calculated based on the sample dry weight difference before and after digestion.

Figure 14:
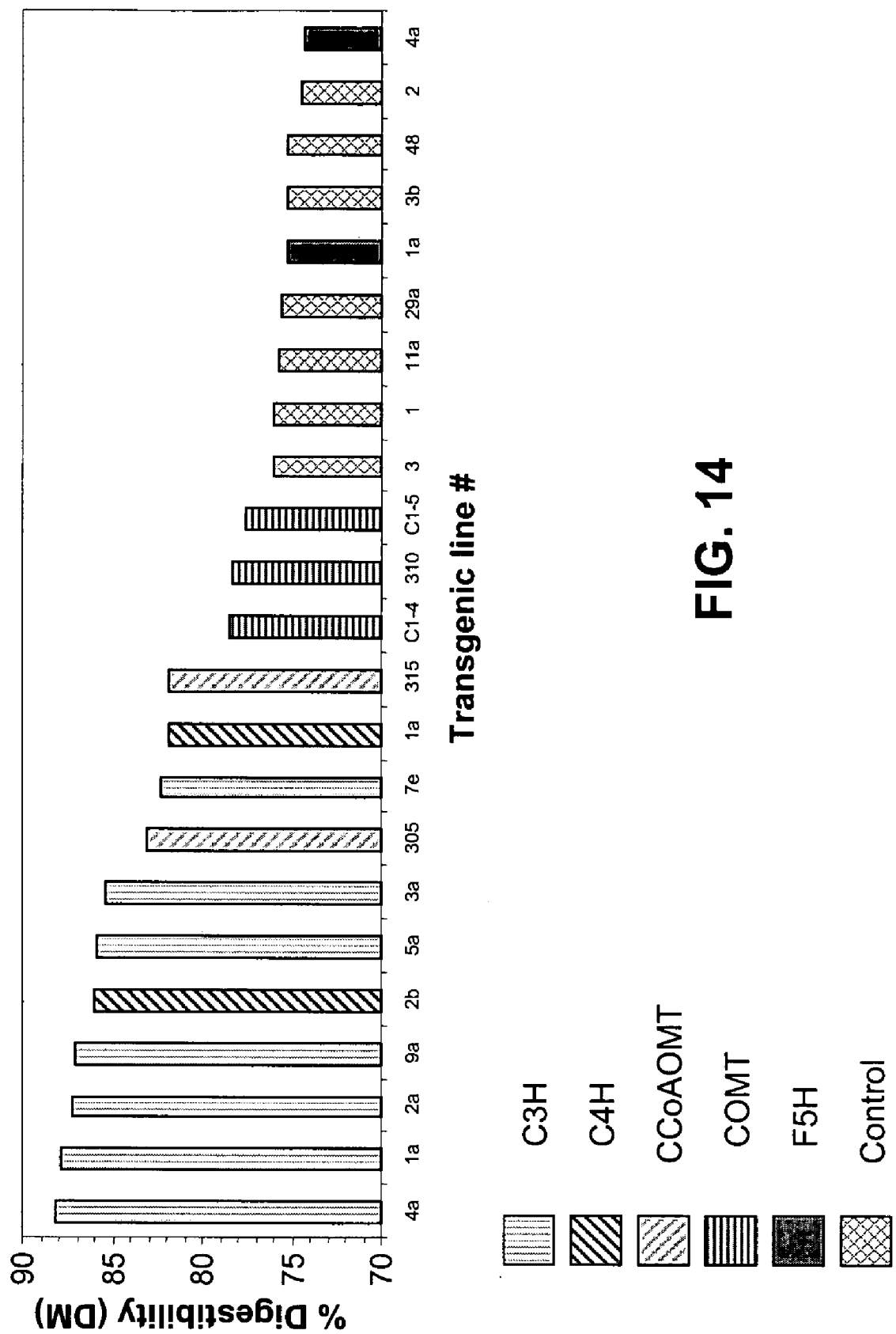
FIG. 14. Shows relative digestibility of control lines and transgenic alfalfa lines expressing antisense C3H, C4H, CCoAOMT, COMT, and F5H constructs.

For each of the 23 different lines used in the study, duplicate forage samples were analyzed in situ in five separate steers. The experiment was performed with stem samples, and then repeated with stems plus leaves. The results (FIG. 14) confirm a striking increase in in situ digestibility end points of stem material from the C3H and C4H lines, greater than observed previously (Guo et al., 2001) or in the present trial for COMT or CCoAOMT down-regulated material. The various empty vector control lines exhibited very similar end point digestibility, which could not be distinguished from that of the F5H lines.

Figure 15:
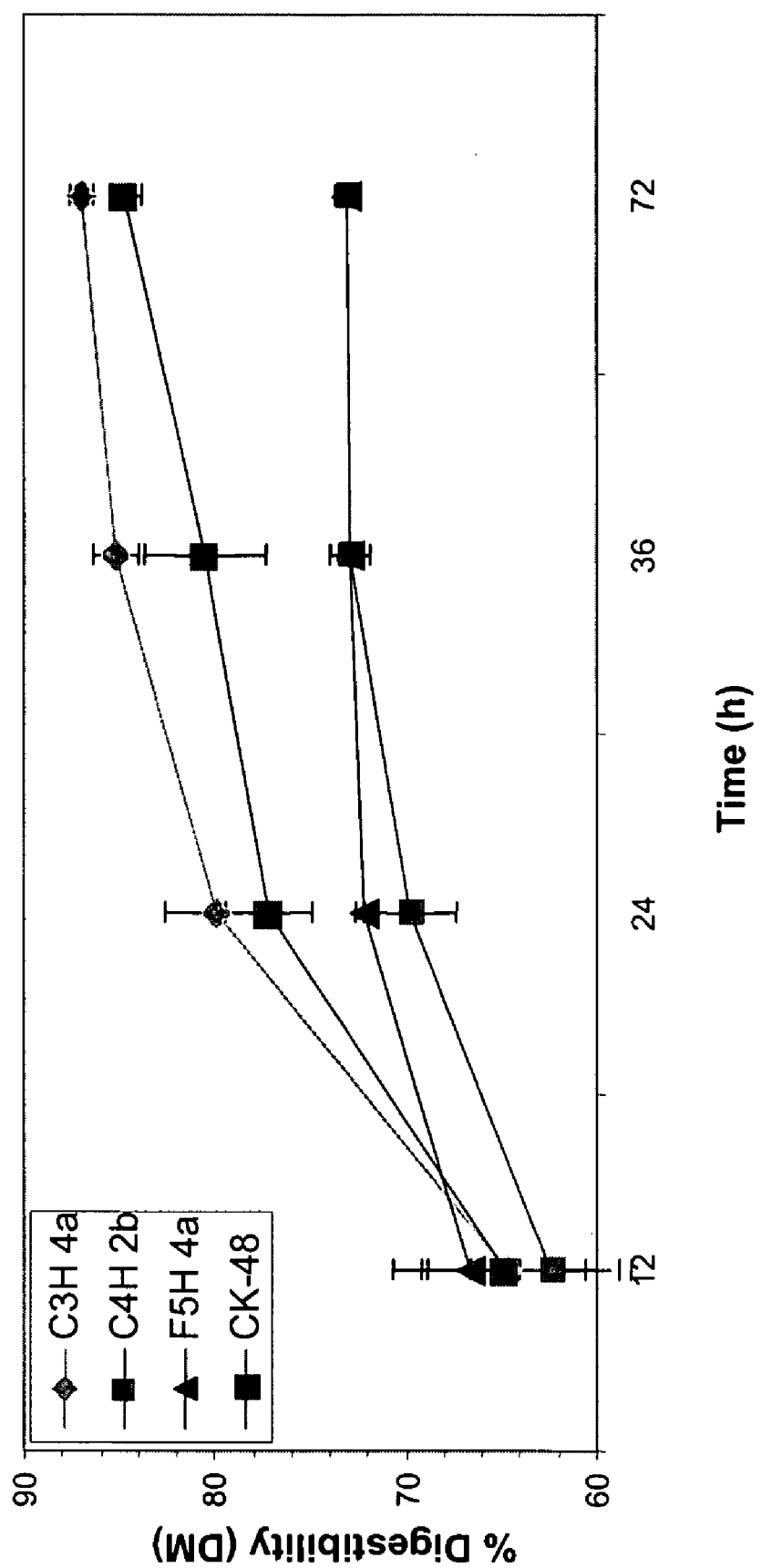
FIG. 15. Shows a time course of percent digestibility of control lines and transgenic alfalfa lines expressing antisense C3H, C4H, and F5H constructs.

Digestibility kinetics for the most digestible line representative of each targeted transcript (FIG. 15) indicated that differences in digestibility for the different lines were apparent within 24 h of incubation in the rumen. Interestingly, F5H line 4a was more digestible than the control line at early time points, but attained the same end-point digestibility value after 36 h.

Figure 16:
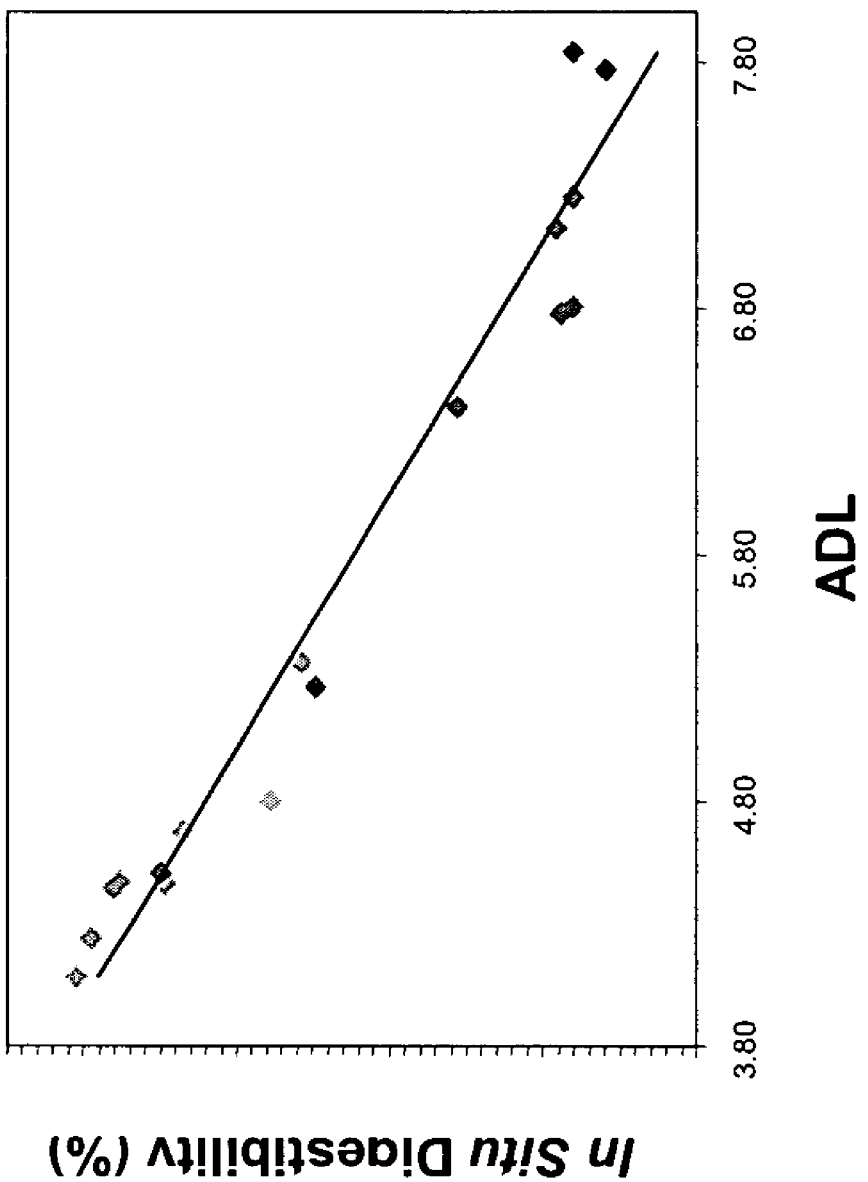
FIG. 16. Shows the correlation between in situ digestibility and ADL content for various control and transgenic alfalfa lines FIG. 17. Shows the correlation between in situ digestibility and H+G+S lignin content for various control and transgenic alfalfa lines FIG. 18. Shows the correlation between in situ digestibility and S/G lignin ratio for various control and transgenic alfalfa lines FIG. 19. Shows the correlation between in situ digestibility and H/T lignin ratio for various control and transgenic alfalfa lines FIG. 20 Shows transcript levels of C3H and HCT during alfalfa stem development.
Figure 17:
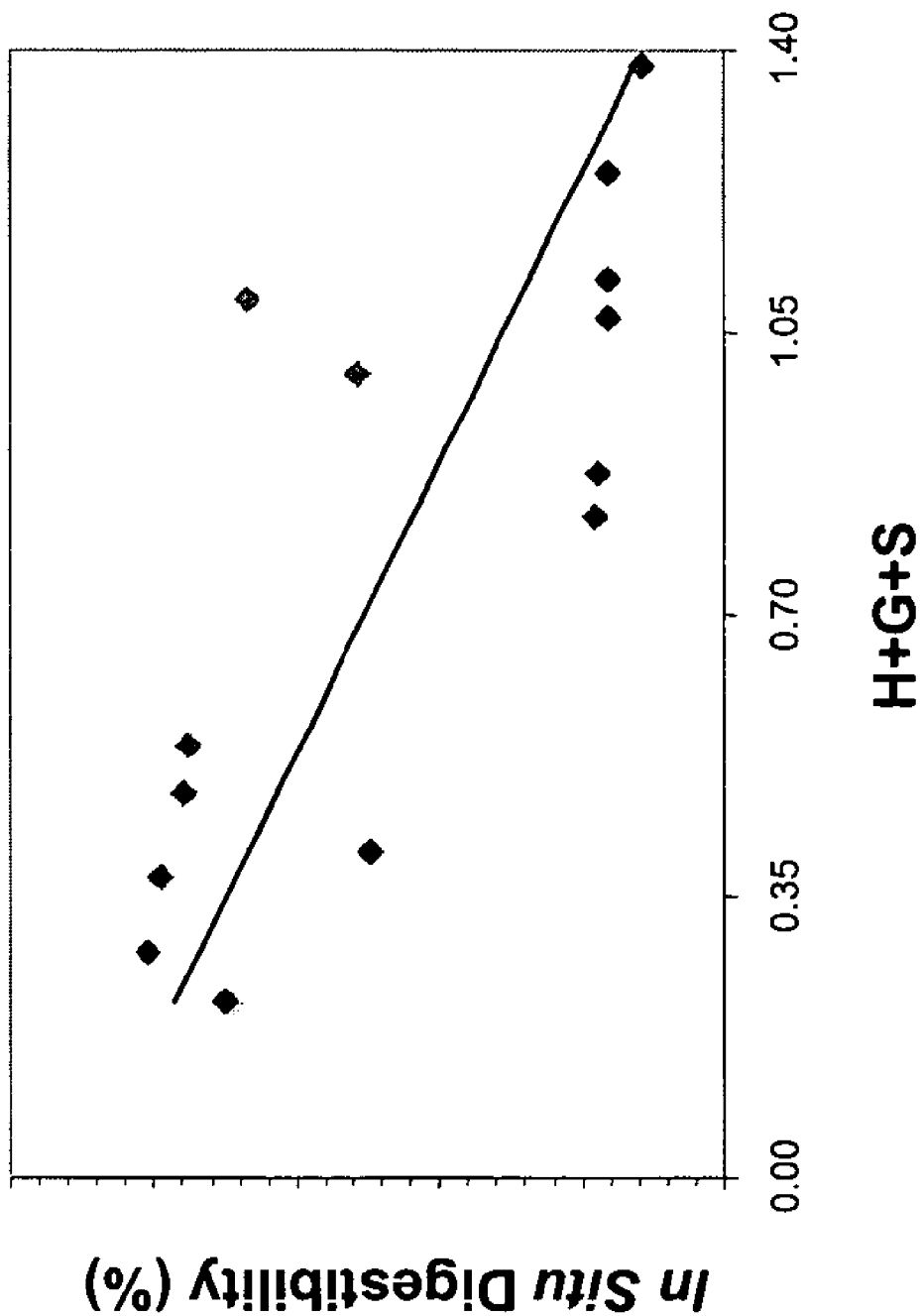
Figure 18:
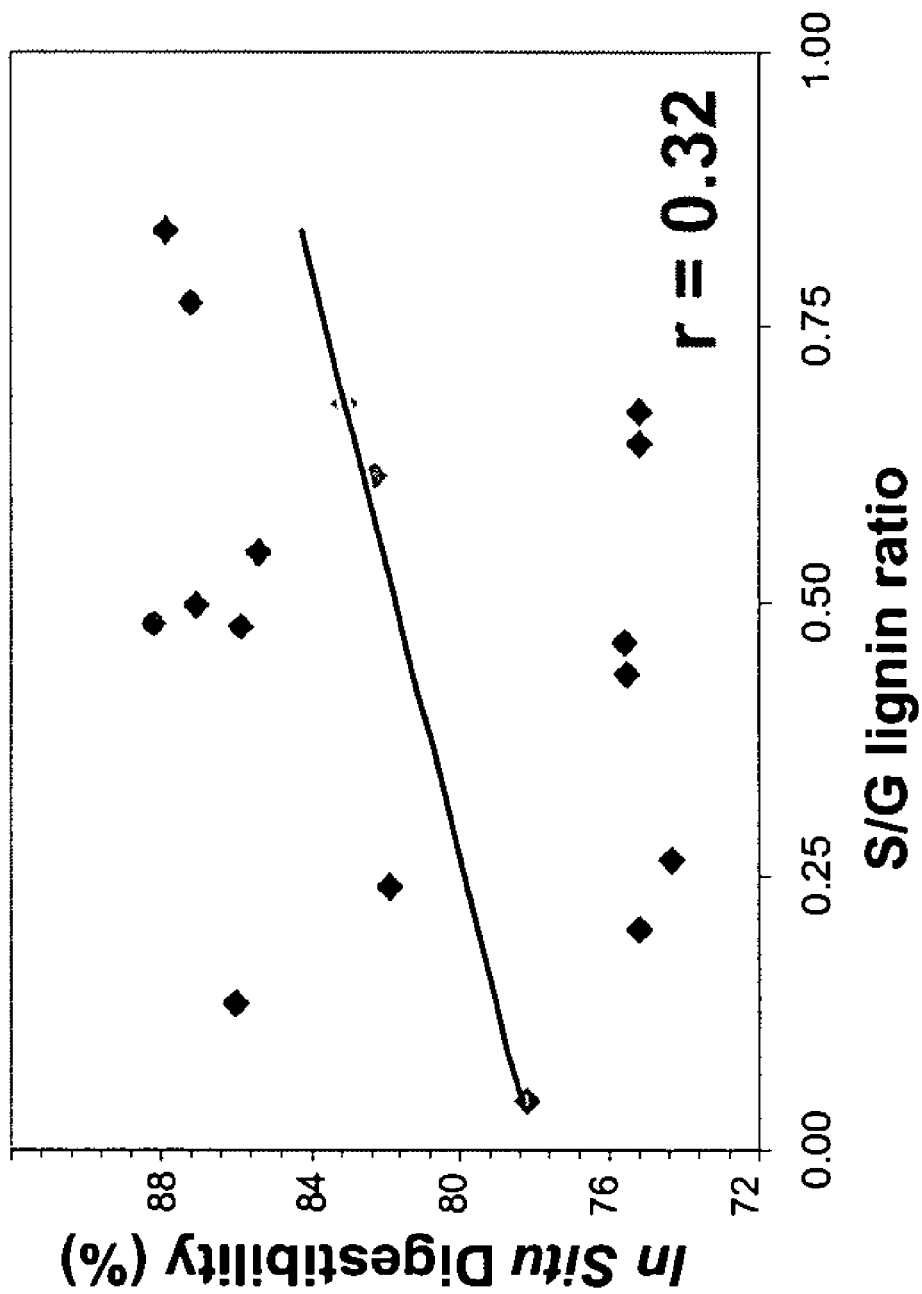
Figure 19:
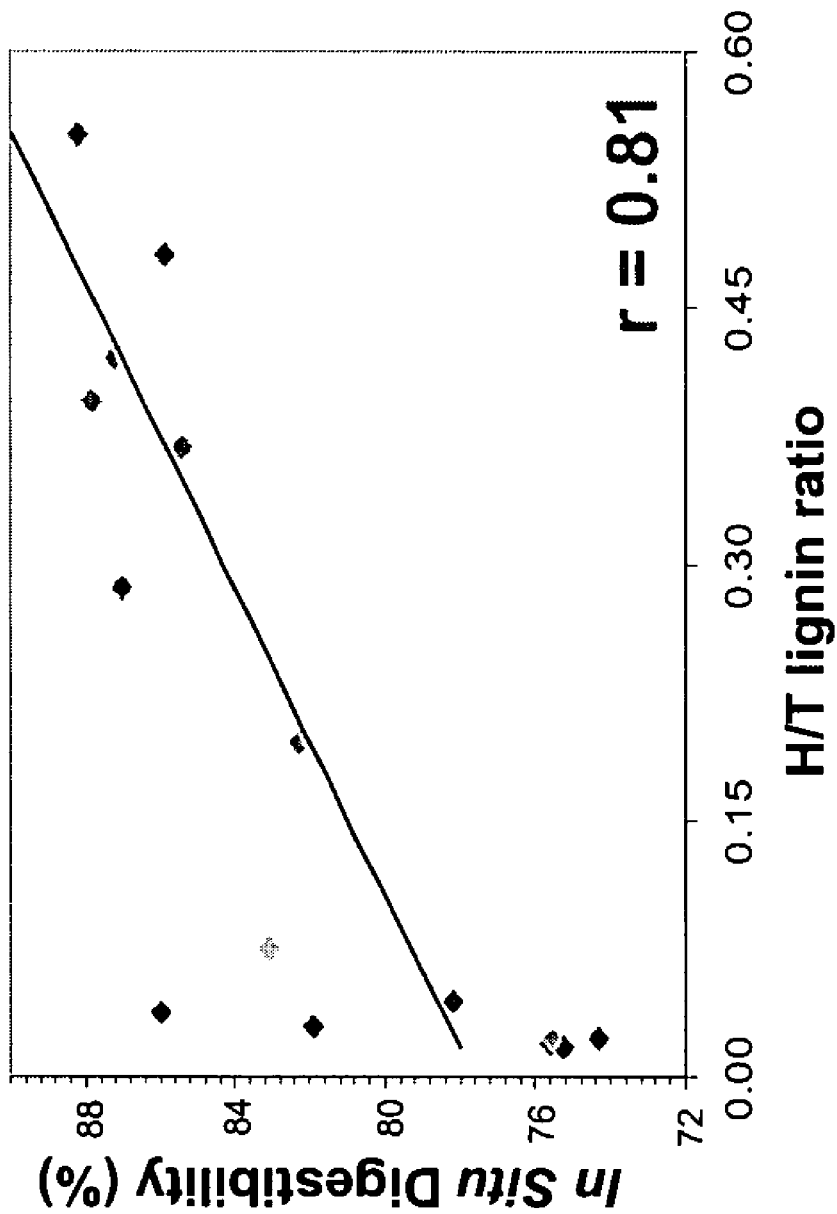

In situ digestibility of total forage from individual lines is plotted as a function of ADL, total thioacidolysis yield, S/G ratio and H/T ratio in (FIGS. 16-19). There was a very strong, negative, linear relationship (r=−0.98) between in situ digestibility and ADL level (FIG. 16). A negative relationship was also seen between in situ digestibility and total thioacidolysis yield (FIG. 17), although the r value was lower, consistent with the fact that thioacidolysis yield is a function of both lignin content and composition (Lapierre et al., 1985). There was no clear relationship between S/G ratio and in situ digestibility (FIG. 18), and the positive relationship (r=0.81) between H/T ratio and digestibility (FIG. 19) can be explained by the contribution of the seven C3H lines, in which H/T ratio was related to reduced lignin and therefore increased digestibility; digestibility in the other lines varied greatly at a relatively constant, low H/T ratio.

Additional analysis of in vitro dry matter digestibility (with rumen fluid) of the various transgenic lines above revealed a strong positive correlation between in vitro and in situ digestibility, suggesting that future studies on digestibility of transgenic alfalfa forage will not require the expensive and time consuming use of fistulated animals. In situ digestibility correlated poorly, if at all, with NDF, ADF, or pectin content. Taken together, the results demonstrate, for the isogenic material analyzed and the parameters that were measured, that only lignin content significantly impacts forage digestibility in alfalfa.

Example 6

Conclusions

Down-regulation was achieved for five genes involved in the lignin pathway in alfalfa. Lignin compositional changes were observed in all the down-regulated lines. For example, the C3H and HCT downregulated lines showed similar lignin compositional changes, which consisted of an increase in the H/Total lignin ratio and decrease in the lignin content. Phenotypic changes were also observed.

Reducing the activity of the early pathway enzymes has a much greater effect on lignin content than does down-regulating F5H, which is only involved in S lignin synthesis. The present C3H lines, which have lost up to 95% of their wild-type enzyme activity, exhibited H/total ratios similar to that of the *Arabidopsis* ref8 mutant, and approximately 25-fold higher than those of control plants, however only those lines with the highest level of down-regulation showed delayed growth. C4H down regulated lines under control of the bean PAL2 promoter showed a decrease in the lignin content and F5H downregulated lines showed a decrease in the S/G lignin ratio. Changes were also found in the phenolic profiles among different transgenic lines. An increase in wall-bound p-hydroxybenzaldehyde and a decrease in vanillin was found in the C3H down-regulated lines, whereas soluble caffeic acid 3-O-glucoside accumulates in CCoAOMT down-regulated lines. The changes in lignin content were not accompanied by significant changes in pectin, hemicellulose, or α-cellulose levels. Since α-cellulose comprises both lignin and cellulose, the large decrease in lignin determined by the acetyl bromide and thioacidolysis methods imply that loss of lignin was counterbalanced by an apparent increase in cellulose.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
U.S. Pat. No. 5,850,020
U.S. Pat. No. 6,610,908
Abdullah et al., *Biotechnology*, 4:1087, 1986.
Bailey and Elkan, In: *Proceedings of the Second International Conference on Intelligent Systems for Molecular Biology*, pp. 28-36, AAAI Press, Menlo Park, Calif., 1994.
Bailey and Gribskov, *Bioinformatics*, Vol. 14, pp. 48-54, 1998.
Bates, *Mol. Biotechnol.*, 2(2):135-145, 1994.
Battraw and Hall, *Theor. App. Genet.*, 82(2):161-168, 1991.
Bevan et al., *Nucleic Acids Research*, 11(2):369-385, 1983.
Bhattacharjee et al., *J. Plant Bioch. and Biotech.* 6, (2):69-73. 1997.
Blancaflor et al., *Planta*, 217(2):206-17, 2003.
Bouchez et al., *EMBO Journal*, 8(13):4197-4204, 1989.
Bower et al., *Plant Journal*, 2:409-416. 1992.
Buckley et al., *Eur. J. Pharmacol.*, 396:141-149, 2000.
Buising and Benbow, *Mol Gen Genet*, 243(1):71-81. 1994.
Callis et al., *Genes Dev.*, 1:1183-1200, 1987.
Casa et al., *Proc. Natl. Acad. Sci. USA*, 90(23):11212-11216, 1993.
Chandler et al., *The Plant Cell*, 1:1175-1183, 1989.
Chapman et al., *Plant Physiol.*, 120:1157-1164, 1999.
Chapman et al., *Plant. Physiol* 116: 1163-1168, 1998.
Chapman, *Chem. Phys. Lipids*, 108:221-230, 2000.
Christou; et al., *Proc. Natl. Acad. Sci. USA*, 84(12):3962-3966, 1987.
Chu et al., *Scientia Sinica*, 18:659-668, 1975.
Conkling et al., *Plant Physiol.*, 93:1203-1211, 1990.
DE App. 3642,829
De Block et al., *EMBO Journal*, 6(9):2513-2518, 1987.
De Block et al., *Plant Physiol.*, 91:694-701, 1989.
De Petrocellis et al., *Chemistry and Physics of Lipids* 108: 191-209, 2000
Dellaporta et al., In: *Chromosome Structure and Function: Impact of New Concepts*, 18th Stadler Genetics Symposium, 11:263-282, 1988.
Devane et al., *Science* 258: 1946-1949, 1992
D'Halluin et al., *Plant Cell*, 4(12):1495-1505, 1992.
Di Marzo et al., *Nature* 372: 686-691, 1994
Downward, *BMJ*, 328(7450): 1245-1248, 2004.
EPA 154,204
Ebert et al., 84:5745-5749, *Proc. Natl. Acad. Sci. USA*, 1987.
Ellis et al., *EMBO Journal*, 6(11):3203-3208, 1987.
Fire et al., *Nature*, 391: 806-11, 1998.

Fraley et al., *Bio/Technology*, 3:629-635, 1985.
Franke et al., *Plant J.* 30:33-45 (2002).
Fromm et al., *Nature*, 319:791-793, 1986.
Gallie et al., *The Plant Cell*, 1:301-311, 1989.
Gelvin et al., In: *Plant Molecular Biology Manual*, 1990.
Ghosh-Biswas et al., *J. Biotechnol.*, 32(1):1-10, 1994.
Goering et al., *Forage Fiber Analysis, Vol.* 379. U.S. Government Printing Office, Washington, D.C. 1970.
Guo et al., *Plant Cell* 13:73-88 (2000).
Guo et al., *Transgenic Res.* 10:457-464 (2001).
Hagio et al., *Plant Cell Rep.*, 10(5):260-264, 1991.
Hamilton et al., *Proc. Natl. Acad. Sci. USA*, 93(18):9975-9979, 1996.
Hansen et al., *Chem. Phys. Lipids.*, 108:135-150, 2000.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35 (1-2):205-218, 1997.
Hillard et al., *J. Neurochem.*, 64:677-683, 1995.
Hinchee et al., *Bio/technol.*, 6:915-922, 1988.
Hoffmann et al., Plant Cell 16:1446-1465, 2004.
Hou and Lin, *Plant Physiology*, 111: 166, 1996.
Hu et al., *Nat. Biotechnol.* 17:808-812 (1999)
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Kaeppler et al., *Plant Cell Reports* 9: 415-418, 1990.
Kaeppler et al., *Theor. Appl. Genet.*, 84 (5-6):560-566, 1992.
Katz et al., *J. Gen. Microbiol.*, 129:2703-2714, 1983.
Khanolkar et al., *Chemistry and Physics of Lipid* 108:37-52, 2000.
Klee et al., *Bio-Technology*, 3(7):637-642, 1985.
Knittel et al., *Plant Cell Reports*, 14 (2-3):81-86, 1994.
Krogh et al., *J. Mol. Biol.*, 305:567-580, 2001.
Lambert and Di Marzo, *Current Med. Chem.*, 6:663-674, 1999.
Lambert et al., *Current Med. Chem.*, 9:739-755, 2002.
Lapierre et al., *J. Wood Chem. Technol.* 5:277-292 (1985)
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.
Lehner et al., *Brief Funct Genomic Proteomic*, Apr; 3(1):68-83, 2004.
Lorz et al., *Mol Gen Genet*, 199:178-182, 1985.
Marcotte et al., *Nature*, 335:454, 1988.
McCabe, Martinell, *Bio-Technology*, 11(5):596-598, 1993.
McCormac et al., *Euphytica*, v. 99 (1) p. 17-25, 1998.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Odell et al., *Nature*, 313:810-812, 1985.
Ogawa et al., *Sci. Rep.*, 13:42-48, 1973.
Omirulleh et al., *Plant Mol. Biol.*, 21(3):415-428, 1993.
Ow et al., *Science*, 234:856-859, 1986.
Paria and Dey, *Chem. Phys. Lipids*, 108:211-220, 2000.
PCT App. WO 94/09699
PCT App. WO 95/06128
PCT App. WO 97/41228
PCT App. WO 97/4103
PCT App. WO 92/17598
Pertwee et al., *Eur. J. Pharmacol.*, 272:73-78, 1995.
Pertwee, *Prog. Neurobiol.*, 63:569-611, 2001.
Potrykus et al., *Mol. Gen. Genet.*, 199:183-188, 1985.
Prasher et al., *Biochem. Biophys. Res. Commun.*, 126(3): 1259-1268, 1985.
Reggio P H, *Tocris Reviews* 10: 1-5, 1999.
Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Sambrook et al., In: *Molecular Cloning-A Laboratory Manual* (second edition), Cold Spring Harbour Laboratory Press, 1989.
Sarker et al., *FEBS Lett.*, 472:39-44, 2000.
Schmid and Berdyshev, *Prostag. Leukotr. Essent. Fatty Acids*, 66:363-376, 2002.
Schmid et al., *Chem. Phys. Lipids*, 121:111-134, 2002.
Schmid et al., *Prog. Lipid Res.*, 29:1-43, 1990.
Sheen et al., *Plant Journal*, 8(5):777-784, 1995.
Shrestha et al., *J. Biol. Chem.* 278: 34990-34997, 2003.
Shrestha et al., *Plant Physiol.*, 130:391-401, 2002.
Singsit et al., *Transgenic Res.*, 6(2):169-176, 1997.
Stalker et al., *Science*, 242:419-422, 1988.
Straus S E, *Proc Natl Acad Sci USA* 97: 9363-9364, 2000.
Sullivan et al., *Mol. Gen. Genet.*, 215(3):431-440, 1989.
Sutcliffe, *Proc. Natl. Acad. Sci. USA*, 75:3737-3741, 1978.
Thillet et al., *J. Biol. Chem.*, 263:12500-12508, 1988.
Thomas et al., *Plant Sci.* 69:189-198, 1990.
Thompson et al., *Euphytica*, 85 (1-3):75-80, 1995.
Thompson et al., *The EMBO Journal*, 6(9):2519-2523, 1987.
Tian, Sequin, Charest, *Plant Cell Rep.*, 16:267-271, 1997.
Tingay et al., *The Plant Journal* v. 11 (6) p. 1369-1376. 1997.
Tomes et al., *Plant. Mol. Biol.* 14(2):261-268, 1990.
Torbet, Rines, Somers, *Crop Science*, 38(1):226-231, 1998.
Torbet, Rines, Somers, *Plant Cell Reports*, 14(10):635-640, 1995.
Toriyama et al., *Theor Appl. Genet.*, 73:16, 1986.
Triparthy et al., *Plant Physiol* 131: 1781-1791, 2003a
Tripathy et al., *In Advanced Research on Plant Lipids*, 2002: 315-318, N. Murata et al., (eds), 2003b
Tripathy et al., *Plant Physiol.*, 121:1299-1308, 1999.
Tsukada; Kusano; Kitagawa, *Plant Cell Physiol.*, 30 (4) 599-604, 1989.
Tusnady and Simon, *J. Mol. Biol.* 283, 489-506, 1998.
Tusnady and Simon, *Bioinformatics* 17, 849-850, 2001.
Twell et al., *Plant Physiol* 91:1270-1274, 1989.
Uchimiya et al., *Mol. Gen. Genet.*, 204:204, 1986.
Van der Stelt et al., *J. Neurosci*, 21:765-8771, 2001.
Van Eck; Blowers; Earle, *Plant Cell Reports*, 14 (5):299-304, 1995.
Vasil et al., *Plant Physiol.*, 91:1575-1579, 1989.
Vogel et al., *Crop Sci.* 39:276-279 (1999)
Walker et al., *Proc. Natl. Acad. Sci. USA*, 84:6624-6628, 1987.
Wang et al., *Molecular and Cellular Biology*, 12 (8):3399-3406, 1992.
Wilson and Nicoll, *Science*, 296:678-682, 2002.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zhou et al., *Plant Cell Reports*, 12 (11). 612-616, 1993.
Zukowsky et al., *Proc. Natl. Acad. Sci. USA*, 80:1101-1105, 1983.

What is claimed is:

1. A method of modifying lignin biosynthesis in a dicot plant comprising down-regulating a hydroxycinnamoyl transferase (HCT) gene in the plant sufficient to modify lignin biosynthesis in the plant, wherein the down-regulating is accomplished by introduction of an isolated nucleic acid sequence that comprises at least 18 contiguous nucleotides of the HCT gene, or its complement, into the plant.

2. The method of claim 1, wherein the plant exhibits improved digestibility relative to a plant in which the down-regulating has not been carried out.

3. The method of claim 1, wherein the isolated nucleic acid sequence is in sense orientation.

4. The method of claim 1, wherein lignin content is decreased in the plant.

5. The method of claim 1, wherein the ratio of syringyl monomers to guaiacyl monomers is decreased.

6. The method of claim 1, further comprising down-regulating a second lignin biosynthesis gene comprising mutating the second lignin biosynthesis gene.

7. The method of claim 1, wherein the isolated nucleic acid sequence is in antisense orientation.

8. The method of claim 1, wherein the isolated nucleic acid is in sense and antisense orientation.

9. The method of claim 1, wherein introducing the isolated nucleic acid comprises plant breeding.

10. The method of claim 1, wherein introducing the isolated nucleic acid comprises genetic transformation.

11. The method of claim 1, wherein the isolated nucleic acid sequence is an antisense or RNAi construct.

12. The method of claim 1, wherein the isolated nucleic acid sequence encodes a ribozyme.

13. The method of claim 1, wherein the plant is selected from the group consisting of: alfalfa (*Medicago sativa*), *Medicago* sp., including *Medicago truncatula, Arabidopsis thaliana*, cotton, sunflower, clover, potato, soybean, tomato, and white or red clover.

14. The method of claim 1, wherein the plant is further defined as a legume.

15. The method of claim 1, wherein the plant is further defined as a forage legume.

16. The method of claim 1, wherein the plant is further defined as alfalfa.

17. The method of claim 1, wherein the down-regulating is accomplished by introduction of an isolated nucleic acid sequence that comprises at least 30 contiguous nucleotides of the HCT gene, or its complement, in the plant.

18. The method of claim 1, wherein the down-regulating is accomplished by introduction of an isolated nucleic acid sequence that comprises at least 50 contiguous nucleotides of the HCT gene, or its complement, in the plant.

* * * * *

UNITED STATES PATENT AND TRADEMARK OFFICE
CERTIFICATE OF CORRECTION

| | | |
|---|---|---|
| PATENT NO. | : 7,663,023 B2 | Page 1 of 1 |
| APPLICATION NO. | : 11/189109 | |
| DATED | : February 16, 2010 | |
| INVENTOR(S) | : Dixon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 290 days.

Signed and Sealed this

Thirtieth Day of November, 2010

David J. Kappos
*Director of the United States Patent and Trademark Office*

SEQUENCE LISTING

<160> NUMBER OF SEQ ID NOS: 45

<210> SEQ ID NO 1
<211> LENGTH: 1782
<212> TYPE: DNA
<213> ORGANISM: Medicago truncatula

<400> SEQUENCE: 1

```
ctctatattc aatatcaacc tgtttccaac cttctctctg ttcaaacaca caattcatca      60
caatggctct gtttctcaca ataccccttt cattcatagc catttttcctc ttttacacac     120
tcttccaaag actgagattc aagcttccac ccggtccacg accgtggccg gtggttggaa     180
acctctacga cataaaacct gtccggttca ggtgttttgc cgaatgggcc caatcctatg     240
ggcccattat atcggtttgg tttggttcga ctctgaacgt gatcgtttca aattcaaagt     300
tggctaaaga agtttaaaag gagaatgatc agcagttggc tgaccggcac agaagtcggt     360
cagcggcaaa gtttagtaga gatgggcagg atttaatttg ggctgattat ggaccccatt     420
atgtgaaggt taggaaggtt tgtacgttag agcttttttc acctaagaga attgaagctt     480
tgaggcctat tagagaagat gaggttactg ctatggttga atccattttc aatgattcta     540
ccaattctga aaatttgggg aaaggtatac tgatgaggaa gtatataggg gcagttgcat     600
tcaacaacat caccaggttg gcatttggga aaagatttgt gaactcagaa ggtgtaatgg     660
atgagcaagg agtagaattc aaggctatag tggcaaatgg attaaagcta ggagcatctc     720
tagctatggc agagcacatc ccttggttgc gctggatgtt tccacttgaa gaggaggctt     780
ttgctaagca cggtgctcgt agggaccggc tcaacagagc catcatggaa gagcatacgc     840
aggcacgtca gaaatccggt ggtgccaaac aacattttgt agatgcactt ctcactttgc     900
aagagaaata tgaccttagt gaagacacca tcattggtct cctttgggac atgattacag     960
ctgggatgga cacaactgca atatcagttg agtgggccat ggcagagctg ataaagaatc    1020
caagagtgca acagaaggca caagaggagc tagacaaggt cattggtttt gaaagagtca    1080
tgactgaaac tgacttctca agcctccctt atttacaatg tgtagccaag gaggctctaa    1140
ggctgcaccc cccaacacca ttaatgctcc cacatcgtgc taacaccaat gtcaaaatcg    1200
ggggctatga tattcccaaa gggtcaaatg tccacgtaaa tgtatgggct gttgcgcgtg    1260
atccagctgt ttggaaagac gcaacagagt ttagacccga gaggtttctt gaggaggatg    1320
tagacatgaa gggtcatgac tttaggctac ttccatttgg agcaggtcgt cgagtatgtc    1380
caggggcaca acttgggatc aatatggtga catccatgtt gggtcatcta ttgcaccatt    1440
tctgctgggc accacccgag ggagtgaacc cagcggagat tgacatggca gagaaccctg    1500
gaatggttac atacatgagg actccattac aggttgtggc ctctcctagg cttccgtcgg    1560
agttgtacaa acgtgtgaca gctgatatct aatcttttc tcatactgca atgttgctgt    1620
ttttcaaaat gttgagtcaa ttttcttatg ggatttattt ctaccattgt gtctatgtaa    1680
ctataattgg aatacaatgt aaggaactat gttaagactc atgacaaatg taagactcgt    1740
gacaaatttg actttgttgc acccttcaga ttttggattg aa                       1782
```

<210> SEQ ID NO 2
<211> LENGTH: 1885
<212> TYPE: DNA
<213> ORGANISM: Arabidopsis thaliana

<400> SEQUENCE: 2

-continued

```
atcaaagtct ccaccacata tatctagaag aattctacaa gtgaattcga tttacacttt      60
tttttgtcct tttttattaa taaatcactg acccgaaaat aaaaatagaa gcaaaacttc     120
atgtcgtggt ttctaatagc ggtggcgaca atcgccgccg tcgtatccta caagctaatc     180
caacggctaa gatacaagtt cccaccaggc ccaagcccca agccgatcgt cggtaaccte     240
tacgacataa aaccggtccg gttcagatgt tactacgagt gggctcaatc ttatggacca     300
atcatatcgg tctggatcgg ttcaattcta acgtggtcg tatctagcgc cgagctagca      360
aaagaagttc tgaaagaaca cgaccagaaa ctcgccgacc ggcaccggaa cagatcgacg     420
gaagcattta gccgcaacgg tcaggatctt atatgggccg attatgggcc tcattacgtg     480
aaggtgagaa agtttgcac gcttgagctc ttcacaccga aacgactcga gtctctcaga      540
cctatccgtg aagatgaagt caccgccatg gttgaatccg tcttcagaga ctgtaacctt     600
cctgaaaaca gagcaaaagg tttacaactg aggaagtact taggagcggt tgcgttcaac     660
aacataacgc ggctagcctt tgggaagcgt tttatgaacg ctgaaggtgt tgtggacgag     720
caagggcttg agttcaaggc catagtatcc aacggtctga agctaggtgc ttcactgtca     780
atagctgaac acatcccgtg gctcaggtgg atgtttccgg ctgatgagaa ggcgtttgct     840
gagcacgggg ctcgtcgtga ccgcctcact cgagctatca tggaggagca tactttggcc     900
cgtcaaaagt ctagtggagc gaaacagcat ttcgttgatg cgttgctaac gttgaaggat     960
cagtatgatc ttagtgagga tactatcatt ggtcttctat gggatatgat cacggcaggg    1020
atggacacga cagcgataac agcggaatgg gcgatggcgg aaatgatcaa gaatccaaga    1080
gtgcaacaaa aagtgcaaga agagttcgac agagtggttg gacttgaccg gatcttaacc    1140
gaggcagatt tctcccgctt accttacttg caatgcgtgg tgaaagagtc attcaggctg    1200
catcctccaa cgcctctaat gctacctcac cgaagcaacg cagatgtcaa gatcggaggc    1260
tatgatattc ccaaaggatc aaacgttcat gtgaatgtgt gggctgtggc tagagacccg    1320
gctgtatgga aaaatccatt tgagtttaga ccagagagat tcttggaaga agatgttgac    1380
atgaagggtc atgattttag gctgcttccg tttggagctg gaagacgggt ttgtcccggt    1440
gcacaacttg gtatcaattt ggtaacttcg atgatgagtc atttgcttca ccattttgtt    1500
tggacaccte ctcaagggac taaaccggag gagattgaca tgtctgaaaa ccctggactc    1560
gttacttaca tgcgtacccc tgtgcaagcg gttgcaacgc ctcggttgcc ttcggatctg    1620
tacaaacgcg tgccttacga tatgtaaatg tcactctgat ctaccttttg ttgctgctgc    1680
tcatgctctt gttgttgttt gtagacatgt ttcttgtggt ttatcatcga aaaacttttg    1740
atgagatttg ttgtatcaat tctctcaagg agaagtaaag aagccatctt ctttgtcatt    1800
gggtttacga tctttcaatc agtgcaatgt tgtaacttga acataagaa taaacaggaa     1860
acaaacatac aaagatattt gcagg                                         1885
```

<210> SEQ ID NO 3
<211> LENGTH: 2409
<212> TYPE: DNA
<213> ORGANISM: Medicago sativa

<400> SEQUENCE: 3

```
cttctttctt tcataatcat tagaatttcc attctatcaa aattctaggt accaccacac      60
aacatattaa ggaacattaa tcaatactat taagatatgg aaacaatatc agcagctatc     120
acaaaaaaca atgccaatga atcattctgc ttgattcatg caaagaataa taataacatg     180
```

| | |
|---|---|
| aaagtgaatg aagctgatcc tttgaattgg ggggtggcag ctgaggcaat gaaaggcagt | 240 |
| caccttgatg aggtgaagcg tatggtggca gagtaccgga aaccggtggt ccgtcttggt | 300 |
| ggcgagacac tgacgatttc tcaggtggct gccattgctg cacatgacca tggtgtgcag | 360 |
| gtggacctgt ctgaatctgc tagggatgga gttaaggcca gcagtgaatg ggtgatggag | 420 |
| agtatgaaca aaggcacgga cagttacggt gtcaccaccg ggtcggcgc cacctcgcac | 480 |
| agccgtacca acaaggtgg tgctttgcag aaagaactca tcaggttttt gaatgcagga | 540 |
| atattcggaa atggaacaga gtcaaatcac acactaccaa aaacagcaac aagagcagcc | 600 |
| atgctagtga ggatcaacac actcctccaa ggttattcag aatagattt tgaaatcttg | 660 |
| gaagccatca ctaagcccct aacaaaacc gtcactccat gtttaccgct tcgtggtaca | 720 |
| atcacagctt caggtgattt agttcctctt tcatacattg ctggtttact caccggaaga | 780 |
| ccaaattcaa aagctcatgg accatctgga gaagtactta atgcaaaaga agcttttaat | 840 |
| ttggctggaa tcaatgctga gttctttgaa ttacaaccaa aagaaggtct tgcccttgtt | 900 |
| aacggaacag ctgttggttc cggtttagct tctattgttc tctttgaggc taacattttg | 960 |
| gctgtgttgt ctgaagttct atcagctatt tttgctgaag ttatgcaagg gaaacctgaa | 1020 |
| tttaccgatc atttgacaca caagttgaaa caccaccctg gtcaaattga ggctgctgcg | 1080 |
| attatggaac acattttgga cggcagctct tatgtcaaag cagctaagaa gttgcatgag | 1140 |
| atagatcctt tgcagaagcc aaaacaagat agatatgcac ttagaacttc accacaatgg | 1200 |
| cttggtcctt tggttgaagt gattagattc tctaccaagt caattgagag agagatcaac | 1260 |
| tctgtcaatg acaacccttt gattgatgtt tcaagaaaca aagctttgca cggcggaaac | 1320 |
| tttcaaggaa cacctattgg agtatccatg gataatacac gtttggctct cgcatcaatt | 1380 |
| ggcaaactta tgtttgctca attctctgag cttgttaatg acttttacaa caatggattg | 1440 |
| ccttcaaatc tttctgctag tagaaatcct agcttggatt atggtttcaa gggagctgaa | 1500 |
| attgccatgg cttcctattg ttctgagttg caatatcttg caaatccggt tacaacccac | 1560 |
| gtccaaagtg ctgagcagca caaccaagat gtgaactctt tgggtttgat ttctgctaga | 1620 |
| aaaacaaatg aagccattga gatccttcag ctcatgtctt ccaccttctt gattgcacta | 1680 |
| tgccaagcaa ttgatttaag acatttggag gagaacttga aaaactcagt caagaacacc | 1740 |
| gtaagtcaag ttgccaaaaa gactcttacc atgggtgtca atggagaact tcacccttca | 1800 |
| agattctgcg aaaagacttt gttgaaagtg gttgacaggg agcatgtatt tgcttatatt | 1860 |
| gatgatcctt gtagcgctac ataccgttg agtcaaaaac taaggcaagt gttggtagat | 1920 |
| catgcactag taaatggaga gagtgagaag aattttaaca cttcaatctt tcaaaagatt | 1980 |
| gctacttttg aggaagagtt gaagaccctc ttgccaaaag aggttgaaag tgcaaggacc | 2040 |
| gcatatgaga gtggaaaccc aacaatccca aacaagatca atggatgcag atcttatcca | 2100 |
| ctttacaagt ttgtgagaga ggagctagga actggtttac taaccggaga aaatgtcatt | 2160 |
| tcaccaggag aagagtgtga caaactattt tcagctatgt gtcagggaaa aatcatcgat | 2220 |
| cctcttcttg aatgtttggg agagtggaac ggtgctcccc ttcctatttg ttaactttgt | 2280 |
| tggttacttt tgaaaatgct ttatttgtat tttatacaag tgtatcaaaa atcatatagg | 2340 |
| tttttcatgc tttaacaaat taatatggaa agctaaaaag ctccagttca gtttcctcca | 2400 |
| aaaaaaaaa | 2409 |

```
<210> SEQ ID NO 4
<211> LENGTH: 2445
```

<212> TYPE: DNA
<213> ORGANISM: Medicago truncatula

<400> SEQUENCE: 4

| | | | | | |
|---|---|---|---|---|---|
| cttccttctc | atctcaggaa | atttacaact | ctaatattca | tctttcacaa | tcatttggat | 60 |
| ttccattctc | tcaaaattaa | ttctaggtac | caccacacaa | caaaattaag | gaacattaat | 120 |
| tattatcaat | taagatatgg | aaacaatatc | agcagctatc | acaaaaaaca | gtgccaatga | 180 |
| atcattctgt | ttgattcatg | ctaagaataa | taacatgaaa | gtgaatgaag | ctgatccttt | 240 |
| gaattggggt | gtggcagctg | aagcaatgaa | aggcagtcac | ttggatgaag | tgaaacgtat | 300 |
| ggtggaggag | taccggaagc | cggtggtccg | tcttggtggc | gaaacactga | ccatttctca | 360 |
| ggtggctgcc | attgctgcac | atgaccatgg | tgtgcaggtg | gagctgtcag | aatctgctag | 420 |
| ggctggtgtt | gaggccagca | gtgattgggt | gatggagagt | atgaacaaag | gaacagacag | 480 |
| ttacggtgtc | accaccggat | cggcgccac | ctcacaccgc | cgtaccaaac | aaggtggtgc | 540 |
| tttgcagaaa | gaactcatca | gattttttgaa | tgctggaata | tttggaaacg | gaactgagtc | 600 |
| aagccacaca | cttccacaca | cagcaacaag | agctgccatg | ctagtgagaa | tcaacacact | 660 |
| cctccaaggt | tattcaggaa | tcagatttga | aatcttggaa | gccatcacca | atctccttaa | 720 |
| caacaacgtc | actccatgtt | taccacttcg | cggtacaatc | acagcttcag | gagatttggt | 780 |
| ccctctatct | tacattgctg | gtttactaac | tggaagacca | aattccaaag | ctcatggacc | 840 |
| atctggagaa | atacttaatg | caaaagaagc | ttttgcattg | gctggaatca | atgctgaatt | 900 |
| cttcgaatta | caaccaaaag | aaggccttgc | acttgttaac | ggaacagctg | ttggttccgg | 960 |
| tttagcttca | attgttctct | tcgaggctaa | cattttggct | gtgttgtctg | aagttctatc | 1020 |
| agctattttt | gctgaagtta | tgcaagggaa | acctgagttt | accgatcatt | tgacacacaa | 1080 |
| gttgaaacac | caccctggtc | aaattgaggc | tgctgctatt | atggaacaca | ttttggatgg | 1140 |
| aagtgcttat | gtcaaagcag | ataaaaagtt | gcatgagatg | gatccattgc | agaaaccaaa | 1200 |
| acaagataga | tatgcgctta | gaacttcacc | acaatggctt | ggtcctttgg | ttgaagtgat | 1260 |
| tagattctct | accaagtcaa | ttgagagaga | gatcaactct | gtcaacgaca | ccccttgat | 1320 |
| tgatgtttca | agaaacaaag | ctttgcatgg | tggaaacttt | caaggaacgc | ctattggagt | 1380 |
| atccatggat | aatacgcgtt | tggctctcgc | atcaattggc | aaacttatgt | ttgctcaatt | 1440 |
| ctctgagctt | gtcaatgatt | tttacaacaa | tggattgcct | tcaaatcttt | ctgcgagtag | 1500 |
| aaatcctagt | ttggattatg | gtttcaaggg | agctgaaatt | gccatggctt | cctattgttc | 1560 |
| tgagttgcaa | tatcttgcaa | atccggttac | aacccacgtc | caaagtgccg | agcagcacaa | 1620 |
| ccaagatgtg | aactctttgg | gtttgatttc | atcgagaaaa | acatatgaag | ccattgagat | 1680 |
| ccttcagctc | atgtcttcca | cattcttgat | tgctctttgc | caagcaattg | atttaagaca | 1740 |
| tttggaggag | aacttgaaaa | actcagtcaa | gaacaccgta | agtcaagtcg | ccaaaaagac | 1800 |
| ccttaccata | ggcgtgaatg | gagaacttca | tccttcaaga | ttttgtgaaa | aagacttatt | 1860 |
| gaaagtggtt | gatagagagc | atgtatttgc | ttatattgat | gatccttgta | gtgctacata | 1920 |
| cccattgagt | caaaaactca | ggcaagtgtt | ggtagatcat | gcattagtta | atggagagag | 1980 |
| tgagaagaat | ttgaacactt | caatctttca | aaagattgca | acttttgagg | aagagttgaa | 2040 |
| gagcctcttg | ccaaaagagg | ttgaaagtgc | aaggaccgca | tatgagagtg | gaaacccaac | 2100 |
| aattccaaac | aagatcaatg | gatgcagatc | ttatccactt | tacaagtttg | ttagagagga | 2160 |
| gttgggaact | ggtttactaa | ctggagaaaa | tgtcatttca | cccggtgaag | tgtgtgacaa | 2220 |

-continued

```
attattcaca gctatgtgtc agggaaaaat cattgatcct cttcttgaat gcttgggaga    2280
gtggaacggt gctcctcttc caatttgtta actttgttgg ttaattctga aaatgtttta    2340
tttgtatcta tacaagtgta acaataatca ttaggttttt catgccttta attaatattg    2400
aaaatttcat ttaaattttc tgcaatatta atgtcaaact tctaa                    2445
```

<210> SEQ ID NO 5
<211> LENGTH: 1946
<212> TYPE: DNA
<213> ORGANISM: Medicago truncatula

<400> SEQUENCE: 5

```
gaaagacacg aagacacgac atcacacatg caatactcaa actgaagaac aaaacaatct      60
ctgcatttta gattcttcac attcacattt tcatcacctc ttcagttcag atcagatcca     120
caaaatcttc gcaccccatt acactatagg aattgaattt tgaagatttt gacaatggcg     180
gcgaattcgt ctaatggaga tcaacataat ggagatcaac agacaacaac aaagcagcct     240
cccctgccat ctccattgcg atttcccaaa ttctttcagt ccaatatgag aattttggtg     300
accggaggag ctggttttat tggttctcac cttgttgaca gattgatgga aaatgagaaa     360
aacgaggtaa ttgtagctga taattacttc actggatgta agacaaccct taaaaaatgg     420
attggtcatc cgagatttga gctaattcgc acgatgtga cagagacact gttggttgag      480
gttgatcgga tctaccatct tgcctgccct gcttctccaa tcttctacaa atacaatcct     540
gtaaagacaa taaagactaa tgtaattgga acactgaaca tgcttgggct tgcaaagcga     600
gttggagcaa ggattttgct tacatctact tcagaagtat atggagaccc tcttatccat     660
ccacaaccag aaacttattg gggaaatgtc aatcctattg gagttcggag ttgctatgat     720
gagggcaagc gtgtggcaga aactttgatg tttgattatc ataggcagca tggactagaa     780
atacgcattg ccagaatctt caacacatat ggaccacgca tgaatatcga tgatgggcgt     840
gtcgtcagca actttattgc tcaggcaatt cgtggtgaac ccttaacagt ccaacttcca     900
ggaacacaaa ctcgcagttt ctgctatgtc tctgacatgg ttgatggcct tattcgtctc     960
atggaaggag aaaacactgg tccaatcaac attgggaacc caggcgagtt tactatgact    1020
gaacttgctg agaatgtgaa ggagcttatt aatccagctg tggagataaa gatggtagag    1080
aacacccctg atgatcctcg gcaaagaaaa cctgatataa caaaagcaac agaattgctt    1140
ggatgggaac caaggtcaa gttgcgggat ggccttcctc ttatggaaga ggatttccgt     1200
ctaaggcttg gggttcctag aaaaaactaa acaaagttgg ttttgcactt tcacctcata    1260
tcatgatgga tattttgata atacttgaga cgtggttgtc actattagat atttcacatt    1320
gagcaattgt ggtaaggaag gttggaggtt gcttgaagtt tgttgcatcg ttttttccttc    1380 ttttttttat ttactattgg tcatataatg gcggagagca atggataaaa aatgtgtagg     1440
accaggaagg gtcacttggc catgttctgt aattgataca gtatgagtgt tttctcttat    1500
ttttctatcc aatttctcct attggaaatg ttacattgag ttgaaatatc ttattatagc    1560
agtaattcga aatctctttt gtgcttgttt ggaaattgga attaccacac acggtgaaac    1620
cgtgcaatca attgaagctc caaggtatat atatcttcat gtggtggttg ctatgtgtag    1680
gtccgtagta atgctattcc aaacatttct ttgtatacta agcgttaggt tagtgagtaa    1740
agtaaataag tgatgaacct cgcacaaaga aatggttgta tcattgagtt cccaacttta    1800
gattgttagg ttcactttta cgaaaagtta tgcatgtaat ggaacggcag cttcacaatt    1860
ctagtatgtg agtaagaaaa tgggtatctt tagagttgat ctacccatat aaatactact    1920
```

-continued

```
tgtcgtattg tttgaggaga tttatc                                  1946

<210> SEQ ID NO 6
<211> LENGTH: 718
<212> TYPE: DNA
<213> ORGANISM: Medicago truncatula
<220> FEATURE:
<221> NAME/KEY: modified_base
<222> LOCATION: (658)..(659)
<223> OTHER INFORMATION: N = A, C, G, and/or T/U

<400> SEQUENCE: 6
ctctaatatt attcctcata attatttgaa tttccattct ctctaaattc tagctaccac    60
cactcaacaa attaagcaac attaattact attagtatca atataagatc atggaaacaa   120
tatcagcagc tatcacaaaa aacagtgcca atgaatcatt ctgtttgatt catgctaaga   180
ataataacat gaaagtgaat gaagctgatc ctttgaattg gggtgtggca gctgaggcaa   240
tgaaaggcag tcaccttgat gaggtgaagc gtatggtgga ggagtaccgg aagccggtgg   300
tccgtcttgg tggcgaaaca ctgaccattt ctcaggtggc tgccattgct gcacatgacc   360
atggtgtgca ggtggagctg tcagaatctg ctagggctgg tgttgaggcc agcagtgatt   420
gggtgatgga gagtatgaac aaaggaacag acagttacgg tgtcaccacc ggattcggcg   480
ccacctcaca ccgccgtacc aaacaaggtg gtgctttgca gaaagaactc ataaggtttt   540
tgaatgctgg aatatttgga aaggaagtg agtcaagcca cacttcca cacacagcaa     600 caagagctgc catgctagtg agaatcaaca cactcctcca agggtattca ggaatcanat   660
ttgaaatctt ggaagccatc accaatctcc taacaacaac gtcacttcat gtttacc      718

<210> SEQ ID NO 7
<211> LENGTH: 652
<212> TYPE: DNA
<213> ORGANISM: Medicago truncatula
<220> FEATURE:
<221> NAME/KEY: modified_base
<222> LOCATION: (645)
<223> OTHER INFORMATION: N = A, C, G and/or T/U

<400> SEQUENCE: 7
tccaaacatg gcaaccatta atccacaaaa tgttagctca aacttgatca ttgactcaga    60
ccctttgaac tggaattcag ctgctaattc actcaagggt agccaccttg atgaagtaaa   120
acgtatgtta gcagagtaca agaagccagt catatgtctt ggtggggtgg ggacactaac   180
tatatctcag gtggctgctg tttctaacag tagctcacat gttaaggttg aactctcaga   240
gtctgcaagg gccggtgttg aagctagctg cgactggatc tccgaaaaca ttgtcaaagg   300
tactccaatt tatggtgtta ccactggctt tggtgctgcc tcacatagaa gaactgaaca   360
aggctttgct cttcagaaag agatggttag gtttctaaac tgcgcaatat ttgggcgtga   420
aagtgagttg tctcatacac tgccttcgtc ggcaacaaga gcagctatgc ttgtgagggt   480
taataccctt ctacaaggct attcaggcat tagatttgaa atcttagaag ctatcaccaa   540
gctcctcaac cataatgtca caccaatctt gccattgcgc ggcacagtta ccgcttccgg   600
tgatctaatt cctctgtcct acatcgctgc attgctaacc ggtangcgaa at           652

<210> SEQ ID NO 8
<211> LENGTH: 2567
<212> TYPE: DNA
<213> ORGANISM: Medicago truncatula
```

<400> SEQUENCE: 8

| | | | | | |
|---|---|---|---|---|---|
| catcattgtt | cattatttcc | cacccaacac | tacgtaacat | ttcctctcct | cttatcattt | 60 |
| catcatcata | gttattactt | tcaacacccc | ctcttccttc | cttttggtaa | aatattcgtg | 120 |
| cattcgtaat | tatggaggga | attaccaatg | gccatgttga | agcaaccttt | tgtttgagca | 180 |
| aaaatggtgg | tgatccactc | aactggggcg | cggcggcgga | gtcattgaca | gggagtcatt | 240 |
| tggatgaggt | gaagcgtatg | gtggaggagt | atcgtaaccc | gttggttaaa | atcggcggtg | 300 |
| agacacttac | cattgctcag | gtggctggaa | ttgcttccca | tgatagtggt | gttagggtgg | 360 |
| agctttcgga | gtcggcaagg | gccggtgtta | aggcaagtag | tgactgggtg | atggatagta | 420 |
| tgaataaagg | tacggacagt | tatggtgtta | ccaccggttt | tggtgctact | tctcaccgga | 480 |
| gaactaaaca | aggtggtgcc | ttgcagaagg | agctaattag | gttttttgaat | gccgaatat | 540 |
| ttggcaatgg | tacagaatca | aattgtacac | taccacatac | agcaacaaga | gctgcaatgc | 600 |
| ttgtgaggat | caacactctt | cttcaagggt | attctggtat | tagatttgaa | atcttggaag | 660 |
| ctatcacaaa | gctcttgaac | aacaatatta | ccccatgttt | accacttcgc | ggtacaatca | 720 |
| cagcttccgg | tgatcttgtt | ccactctctt | acattgccgg | tttattaacg | ggcagaccca | 780 |
| actctaaagc | cgttggaccg | tctggagaaa | ttctcaatgc | caaggaagct | tttcaacttg | 840 |
| ctggcattgg | ttctgatttc | tttgaattgc | aacctaagga | aggtcttgct | cttgttaatg | 900 |
| gaactgctgt | tggttctggt | ttagcttcta | ttgttctgtt | cgaagcaaat | gtactagcgg | 960 |
| ttttgtctga | agttatgtcg | gcaattttcg | ctgaagttat | gcaagggaaa | cctgaattta | 1020 |
| ctgatcattt | gactcataag | ttgaagcatc | accctggtca | aattgaagct | gctgctatta | 1080 |
| tggagcatat | tttggatgga | agcgcttatg | ttaaagccgc | taagaagtta | cacgagactg | 1140 |
| atcctttgca | aaagcctaaa | caagatcgtt | atgcacttag | aacttcacct | caatggcttg | 1200 |
| gtcctttgat | tgaagtgata | agattttcga | ccaagtctat | tgaaagagag | attaactcgg | 1260 |
| tcaacgacaa | cccctttgatc | gatgtttcaa | ggaacaaggc | catacatggt | ggtaactttc | 1320 |
| aaggaacacc | tatcggagtt | tcaatggaca | cactcgtttt | agctcttgct | tcgatcggta | 1380 |
| aactcatgtt | tgctcaattc | tctgagcttg | ttaatgattt | ttacaacaat | ggtttgcctt | 1440 |
| cgaatcttac | tgcaagtaga | aacccaagtt | tggattatgg | tttcaaggga | tctgaaattg | 1500 |
| ctatggcttc | ttattgctcc | gagttacaat | atcttgctaa | ccctgtcacc | acccatgtgc | 1560 |
| aaagtgctga | gcaacacaac | caagacgtta | actctttggg | tttgatttct | tctagaaaaa | 1620 |
| caaacgaggc | tattgagatc | ttaaagctca | tgtcttccac | tttcttgatc | gcgctttgcc | 1680 |
| aagcaattga | cttgaggcat | ttggaagaga | atttgaggaa | cactgtcaag | aacactgtaa | 1740 |
| gccaagttgc | taagagaaca | ctcacaaccg | gtgtcaatgg | agaacttcat | ccttcaagat | 1800 |
| tttgcgagaa | agatttgctc | aaagttgtcg | acagggagta | tgtgtttgcc | tatgctgatg | 1860 |
| atccttgcct | agctacatac | ccttttgatgc | aaaagttgag | acaagtgctt | gtggatcatg | 1920 |
| cattagtgaa | taccgaagga | gagaagaatt | cgaacacatc | aatcttccaa | aagattgcaa | 1980 |
| catttgagga | tgaattgaag | gctatcttgc | caaggaagt | tgaaagtgca | aggacagcat | 2040 |
| atgaaaatgg | acaaagtgga | atttcaaaca | agattaagga | atgtaggtct | tatccattgt | 2100 |
| acaagtttgt | tagagaggag | ttgggaacag | cgttgctaac | cggtgaaaaa | gtgatatcgc | 2160 |
| caggagaaga | gtgcgacaaa | ttgttcacag | ctatgtgcca | aggtaaaatt | gttgatcctc | 2220 |
| ttatggaatg | tctcggagag | tggaacggcg | ctcctcttcc | aatttgttaa | tttactcaat | 2280 |
| ctgtttcttg | gagaaatgat | ttctttatat | atttgtagca | gactagtagt | tgctttgaga | 2340 |

-continued

```
agcaatattg gttctataag cctatggtaa atgacaaacc aatatccttc tgatagcatc      2400
gtttattaag ttttccttg atgttcagga acttttaatt gttttgtaa tagaatttca       2460 tttgtttgcc aaaactttgg gtgcaaatat catatgatac gtgatctttg atgtaaatgg      2520 tgttttttt ccatgaataa atagtgttta ctttcaacca tgaaaaa                    2567
```

<210> SEQ ID NO 9
<211> LENGTH: 1025
<212> TYPE: DNA
<213> ORGANISM: Medicago truncatula

<400> SEQUENCE: 9

```
agggttgaag cacctttgt ttgagcaaaa atggtggtga tccactcaac tggggcgcgg        60
cggcggagtc attgacaggg agtcatttgg atgaggtgaa gcgtatggtg gaggagtatc      120
gtaacccgtt ggttaaaatc ggcggtgaga cacttaccat tgctcaggtg gctggaattg      180
cttcccatga tagtggtgtt agggtggagc tttcggagtc ggcaagggcc ggtgttaagg      240
caagtagtga ctgggtgatg gatagtatga ataaaggtac ggacagttat ggtgttacca      300
ccggttttgg tgctacttct caccggagaa ctaaacaagg tggtgccttg cagaaggagc      360
taattaggta attaactact actaattaat actattttaa tattttaata actttatgtg      420
catttcacgt ctatagcatg tgttgcattt cgtattaaca tgtcatgtca tgaattctcc      480
aatatcgtca acatgttgat taggagttcc ttagatttt gtaaaaaat aaaataaatc       540 tttgatgaat tcttaatttt taacaaatga atgtgttgat aaattttttt taaaactcga      600
tatccaatcc aattaattaa aaatatcgat tgtctaaaac tttttggttg tttaaaataa      660
tgttttgtga ttgagagatg tttatatttc atgtatgata gaatctcgaa tatgatttca      720
atagaatctt gaatataatt agctatctaa ttagaggaaa ctaatggtag aaaacaaact      780
ttttccatat ttggtgttgc tatatctttt ttatttattt tatgaattta ccaaatttaa      840
gctccctttt ttgtcaccta agaaaaagc tctctctttt gagttttgac caaatacgaa      900
aattgataat ttttaggggg aaatacgaaa atttataatt aattagccaa acccttaat     960 atatgttagg gaaaaccctt taaaatataa ttcgtgctta taaaactatt ttataaggat    1020
ctctc                                                                1025
```

<210> SEQ ID NO 10
<211> LENGTH: 2445
<212> TYPE: DNA
<213> ORGANISM: Medicago truncatula

<400> SEQUENCE: 10

```
cttccttctc atctcaggaa atttacaact ctaatattca tctttcacaa tcatttggat       60
ttccattctc tcaaaattaa ttctaggtac caccacacaa caaattaag gaacattaat       120 tattatcaat taagatatgg aaacaatatc agcagctatc acaaaaaaca gtgccaatga      180
atcattctgt ttgattcatg ctaagaataa taacatgaaa gtgaatgaag ctgatccttt      240
gaattggggt gtggcagctg aagcaatgaa aggcagtcac ttggatgaag tgaaacgtat      300
ggtggaggag taccggaagc cggtggtccg tcttggtggc gaaacactga ccatttctca      360
ggtggctgcc attgctgcac atgaccatgg tgtgcaggtg gagctgtcag aatctgctag      420
ggctggtgtt gaggccagca gtgattgggg gatggagagt atgaacaaag gaacagacag      480
ttacggtgtc accaccggat tcggcgccac ctcacaccgc cgtaccaaac aaggtggtgc      540
```

-continued

```
tttgcagaaa gaactcatca gatttttgaa tgctggaata tttggaaacg gaactgagtc      600
aagccacaca cttccacaca cagcaacaag agctgccatg ctagtgagaa tcaacacact      660
cctccaaggt tattcaggaa tcagatttga atcttggaa  gccatcacca atctccttaa      720
caacaacgtc actccatgtt taccacttcg cggtacaatc acagcttcag gagatttggt      780
ccctctatct tacattgctg gtttactaac tggaagacca aattccaaag ctcatggacc      840
atctggagaa atacttaatg caaaagaagc ttttgcattg gctggaatca atgctgaatt      900
cttcgaatta caaccaaaag aaggccttgc acttgttaac ggaacagctg ttggttccgg      960
tttagcttca attgttctct tcgaggctaa catttttggct gtgttgtctg aagttctatc     1020 agctatttt  gctgaagtta tgcaagggaa acctgagttt accgatcatt tgacacacaa     1080
gttgaaacac caccctggtc aaattgaggc tgctgctatt atggaacaca ttttggatgg     1140
aagtgcttat gtcaaagcag ataaaaagtt gcatgagatg gatccattgc agaaaccaaa     1200
acaagataga tatgcgctta gaacttcacc acaatggctt ggtcctttgg ttgaagtgat     1260
tagattctct accaagtcaa ttgagagaga gatcaactct gtcaacgaca accccttgat     1320
tgatgtttca agaaacaaag cttttgcatgg tggaaacttt caaggaacgc ctattggagt     1380
atccatggat aatacacgtt tggctctcgc atcaattggc aaacttatgt ttgctcaatt     1440
ctctgagctt gtcaatgatt tttacaacaa tggattgcct tcaaatcttt ctgcgagtag     1500
aaatcctagt ttggattatg gtttcaaggg agctgaaatt gccatggctt cctattgttc     1560
tgagttgcaa tatcttgcaa atccggttac aacccacgtc caaagtgccg agcagcacaa     1620
ccaagatgtg aactctttgg gtttgatttc atcgagaaaa acatatgaag ccattgagat     1680
ccttcagctc atgtcttcca cattcttgat tgctctttgc caagcaattg atttaagaca     1740
tttggaggag aacttgaaaa actcagtcaa gaacaccgta agtcaagtcg ccaaaaagac     1800
ccttaccata ggcgtgaatg gagaacttca tccttcaaga ttttgtgaaa aagacttatt     1860
gaaagtggtt gatagagagc atgtatttgc ttatattgat gatccttgta gtgctacata     1920
cccattgagt caaaaactca ggcaagtgtt ggtagatcat gcattagtta atggagagag     1980
tgagaagaat ttgaacactt caatctttca aaagattgca acttttgagg aagagttgaa     2040
gagcctcttg ccaaaagagg ttgaaagtgc aaggaccgca tatgagagtg aaacccaac      2100 aattccaaac aagatcaatg gatgcagatc ttatccactt tacaagtttg ttagagagga     2160
gttgggaact ggtttactaa ctggagaaaa tgtcatttca cccggtgaag tgtgtgacaa     2220
attattcaca gctatgtgtc agggaaaaat cattgatcct cttcttgaat gcttgggaga     2280
gtggaacggt gctcctcttc aatttgttaa actttgttgg ttaattctga aaatgtttta     2340
tttgtatcta tacaagtgta acaataatca ttaggttttt catgccttta attaatattg     2400
aaaatttcat ttaaattttc tgcaatatta atgtcaaact tctaa                    2445
```

<210> SEQ ID NO 11
<211> LENGTH: 2406
<212> TYPE: DNA
<213> ORGANISM: Medicago truncatula

<400> SEQUENCE: 11

```
caatctatct atctcttgaa acacaacaat atatataatt aaccttaatc aacctcaatt       60
tcttcatcat ggagttttca aatggagata atagcaatgg tagtaacggt tcttccatga      120
atcttcgcaa tggtggaaca aaaactagta acaacaatga cccctttgaat tggggtatag     180 ctgcagattc tatgaagggt agtcaccctag atgaggtgaa gcgtatggta gaggaatacc     240
```

```
ggaaaccggt tgtgcccttta ggtggaaaag gtttaacaat agcacaagtg gctgcggttg    300
caacttatag taccggtgtg gcggttgaac tagcggaaga ggcacgctcc ggcgttaaag    360
ctagtagtga ttgggtggtt gatagtatga ataaagggac tgatagctat ggtgtgacca    420
ctgggtttgg tgcaacctca cacagaagaa caaataaagg tagtgcccctt caaagtgaac    480 tcatcagatt tctgaatgct ggaattttcg gcaatggaac agaagcatct cagacattac    540
ctcccacagc cacaagagca ggcatgttgg ttagaatcaa cacattgctt caaggatatt    600
caggaatcag atttgaaatc atggaagcta tagcaaaatt tctgaaccat aacataacac    660
catgtcttcc attaagaggt acaatcactg catcaggtga tttaattcct ttatcatatg    720
ttgctggcct tttaattgga aggccaaatt caaaatctat tggacctaat ggacaagttc    780
tgaatgctca agaggctttt caactagctg gaattgaaac tggtttcttt gagttgcaac    840
ctaaagaagg tttagcacta gtgaatggta ctgcagttgg atcaggtttg gcttcattgg    900 ttcttttttga tacaaattta ctagttgttc tctcggaaat tttgtctgcg attttcgcgg    960
aagttatgct aggaaaacct caattcactg accatttaat tcataaagtg aaacttcatc    1020
ctggtcaaat tgaggctgct gctattatgg aacatatttt agatggaagt tattatggta    1080
aggctgcaca aaaagtacat gagattaatc cacttcagaa gcccaaacaa gatagatacg    1140
cgattcgaac atcaccgcag tggcttggac cgcagattga agtgattcga tacgcaacaa    1200
agatgattga gagggagata aattccgtga atgacaatcc acttattgat gtttcaaggg    1260
ataaggcact tcatggagga aatttccaag gtacaccgat tggtgtatcg atggataaca    1320
ctcgtttagc cattgctgcc attggtaaac ttatgtttgc tcaattcact gagcttgtga    1380
atgacatcta taacaacgga ttgccttcaa gtctcactgc tagccgcaat ccaagtttgg    1440
attacggctt caaaggagca gaagttgcaa tggcatccta ttgttcagaa cttcaatacc    1500
ttgctagtcc tgtcaccact catgtccaaa gtgctgaaca acataaccaa gatgttaact    1560
ctttaggctt gatctcagca agaaaaacag ctgaagcagt tgaaatatgg aagctgatgt    1620
catccacttt cttagttgca ttgtgccaag ccattgatct aaggcacatt gaggaaaact    1680
tcaaaagtgt tgtcaagaac actgtaagtc aagtagccaa gagaattcta acagttggtg    1740
tcaatggtga gttgcatcca tcaaggtttt gtgagaagga tttactcaat gttgttgaag    1800
gtgagtatgt tttcacttac attgatgacc cttgcagtcc tatatatcct ctaatgcaga    1860
agctgagata tgtactagtt gatcatgcat tgcaaaatgg tgataaggag gcaaattcaa    1920
gcacctcgat tttccaaaag attggagctt ttgaggaaga gcttaaggcc ttttgccta    1980 aagaggtgga aaatgctagg gttgaaattg aaaatggaaa ccctgcagtt cctaatatga    2040
tcaaggaatg tagatcatat ccattgtaca agttcatgag agaaactta gggacaagtt    2100 tgcctgacag gtgagaaaat taagtcacct ggtgaggact gtgataaggt tttcacagca    2160
atgtgtgatg gaaggtttat tgatcccatg ttggattgtc taaaggagtg gaatggtgtt    2220
cctctaccta tctgctagga ttgtgctact ctaatgtaat ttttttctttt ctttctttct    2280 atttcaaaga ctttgttttt ccttttttcat gtaatgttta tttttatgatg ttgggcatgt    2340 attttaaact acgataacaa tctgtatgat ttgatgttat attatatgaa tacgttcttt    2400
gtgtgc                                                                2406

<210> SEQ ID NO 12
<211> LENGTH: 1237
<212> TYPE: DNA
```

<213> ORGANISM: Medicago truncatula

<400> SEQUENCE: 12

```
ggcacgaggc gacaatcctc tgattgatgt ggcaacggat aaggctctaa atggtggtaa      60
tttccaaggc accccaattg gagtttcaat ggataatgta cgtttagctg ttacttcaat     120
tggaaaactc gtctttgcgc aatttactga gttagtcaat gacttgtata acaatgggct     180
gccgtcaaat ctttctgctg gtagaaaccc aagtctggat tatggtttta aggcctctga     240
agttgccatg gctgcttatt gttctgaact tcaatattta gcaaatcctg tgacaagtca     300
tgtgcaaagt gctgagcagc acaaccaaga tgtgaactct ttggggttga tttctgctat     360
gaaaacagtg gaagccattg agatattgaa gctcatgtct ccacatatt tggttgcact      420
ctgccaagct attgacttga ggcatttgga ggaaattttc aagaactctg tcaagaaaac     480
tgtaagcaga gtttttaaga agacattaat catagatgac agagaagaaa tcgatccatt     540
tagacattgt gaggaaaatt tgctcaaagt ggttgataga gaatatgtat tctcctacat     600
agatgatccc tttaatgtta cgtacccgtt gatgccaaaa ctaaagcaag tactttatga     660
gcatgcgcac atcagtgcca taataataa ggatgcgaaa tcttcaacat ttgagaaaat      720
tggagctttt gaggatgaat tgaagtctct tttgccaaag gaagttgaaa gtgcaagggt     780
tgcatttgag aagggaaatt ctgaaattcc aaacagaatt aaggaatgta ggtcataccc     840
actatacaag tttgtgaggg aagaactaaa gatagggttg ctgacaggag aaaaggatgt     900
cacaccagat gaggaatttg aaaaagtatt tacagcaatg tgtcaagcaa agattgttga     960
tccaattctg gaatgccttg gtgattggaa aggagttccc atcccaatat gatctgcaaa    1020
tgtttaacca taatcagcag gcatatgttt tttcttgtgt tacccatgtt tggcttctat    1080
atgaataact tgttgagaga aacttgtgta tatttctctt gatgtaataa tagtcacaaa    1140
ttttacacaa ttatttgcta ttagataaat ataatcatgt gtggaaaaga tggctttcct    1200
tcggtaatga tattattaat gacgtattta agtcctc                             1237
```

<210> SEQ ID NO 13
<211> LENGTH: 2178
<212> TYPE: DNA
<213> ORGANISM: Arabidopsis thaliana

<400> SEQUENCE: 13

```
atggagatta cggggcaca caagagcaac ggaggaggag tggacgctat gttatgcggc       60
ggagacatca agacaaagaa catggtgatc aacgcggagg atcctctcaa ctggggagct     120
gcagcggagc aaatgaaagg tagccatttg gatgaagtga agagaatggt tgctgagttt     180
aggaagccag ttgtgaatct tggtggtgag actctgacca ttggacaagt ggctgcgatc     240
tcaactattg gtaacagtgt gaaggtggag ctatcggaga cagctagagc cggtgtgaat     300
gctagtagtg attgggttat ggagagtatg aacaaaggca ctgatagtta tggtgttact     360
actggttttg gtgctacttc tcatcggaga accaaaaacg tgtcgcact  tcagaaggaa     420
cttattagat tccttaacgc cggaatattc ggaagcacga agaaacaag ccacacattg      480
ccacactccg ccacaagagc cgccatgctt gtacgaatca acactctcct ccaaggattt     540
tccggtatcc gatttgagat tctcgaagca attaccagtt tcctcaacaa caacatcact     600
ccatctctcc ccctccgtgg tacaatcacc gcctccggag atctcgttcc tctctcctac    660
atcgccggac ttctcaccgg tcgtcccaat tccaaagcta ctggtcccaa cggtgaagct     720
ttaacagcag aggaagcttt caaattagca ggaatcagct ccggattctt tgatctccag    780
```

```
cctaaggaag gtctcgcgct agtcaatggc acggcggttg gatctggaat ggcgtcaatg      840
gtgttattcg aaacgaatgt tctctctgtt ttggctgaga ttttgtcggc ggttttcgca      900
gaggtgatga gtggtaagcc tgagttcacc gatcatctca ctcacagact taaacatcat      960
cccggtcaaa tcgaagcggc ggcgataatg gagcatatcc tcgacggaag ctcgtacatg     1020
aaattagctc agaagcttca cgagatggat ccgttacaga aacctaaaca agatcgttac     1080
gctcttcgta cttctcctca atggttaggt cctcaaatcg aagtgatccg ttacgcaacg     1140
aaatcgatcg agcgtgagat taactccgtc aacgataatc cgttgatcga tgtttcgagg     1200
aacaaggcga ttcacggtgg taacttccaa ggaacaccaa tcggagtttc aatggataac     1260
acgagattgg cgatagcagc gattggtaaa ctcatgtttg ctcaattctc agagcttgtg     1320
aatgatttct acaacaatgg tttaccctcg aatctaaccg cttcgaggaa tccaagtttg     1380
gattatggat tcaagggagc tgagattgca atggcttctt attgttcaga gcttcaatac     1440
ttagctaatc ctgtgactag ccatgttcaa tcagcagagc aacataacca agatgtcaac     1500
tctttgggac taatctcgtc tcgcaaaact tctgaagctg ttgatattct caagcttatg     1560
tcaacaacgt tcctcgttgc gatttgtcaa gctgtggatt tgagacattt ggaggagaat     1620
ttgagacaga ctgtgaagaa cactgtctct caagtggcga agaaagttct tactactgga     1680
gtcaatggtg agcttcatcc ttctcgcttc tgcgaaaagg atttactcaa agttgtagac     1740
cgtgaacaag tctacacata cgcggatgat ccttgtagcg caacgtaccc gttgattcag     1800
aagctgagac aagttattgt tgaccatgct ttgatcaatg gtgagagtga agaatgca     1860 gtgacttcaa tcttccataa gattggagct ttcgaggagg agcttaaggc agtgctaccg     1920
aaagaagtgg aagcagcaag agcagcctac gataacggaa catcggctat cccgaacagg     1980
atcaaggaat gtaggtcgta tccattgtat agattcgtga gggaagagct tggaacagag     2040
cttttgaccg gagagaaagt gacgtcgcct ggagaagagt tcgacaaggt tttcacggcg     2100
atttgtgaag gtaaaatcat tgatccgatg atggaatgtc tcaacgagtg gaacggagct     2160
cccattccaa tatgttaa                                                   2178

<210> SEQ ID NO 14
<211> LENGTH: 2153
<212> TYPE: DNA
<213> ORGANISM: Arabidopsis thaliana

<400> SEQUENCE: 14
atggatcaaa tcgaagcaat gttgtgcggc ggaggagaga agacaaaagt ggcggttact       60
acgaagactt tggcagatcc attgaattgg ggtttagcag cggatcaaat gaaaggaagt      120
catttagatg aagtgaagaa gatggtcgaa gagtatcgta gaccagtcgt gaacttggcg      180
gagaaacact gacgatcgga caagttgctg ccatctccac cgtaggaggc agcgttaagg      240
ttgagttagc ggagacttca agagccggtg tgaaagctag cagtgattgg ttatggaga       300 gcatgaacaa aggtactgac agttacgagt caccaccggc ttttggtgct acttctcacc      360
ggagaaccaa aaacggcacc gcattacaaa cagaactcat tagattttga aacgccggaa      420
tattcggaaa cacgaaggag acatgtcaca cactgccgca atccgccaca agagccgcca      480
tgctcgtcag agtcaacact cttctccaag gatactccgg gatccgattc gagatcctcg      540
aagcgattac aagtctcctc aaccacaaca tctctccgtc actacctctc cgtggaacca      600
ttaccgcctc cggcgatctc gttcctctct cttacatcgc cggacttctc accggccgtc      660
```

```
ctaattccaa agccaccggt cccgacggtg aatcgctaac cgcgaaagaa gcttttgaga      720
aagccggaat cagtactgga ttcttcgatt tacaacctaa ggaaggttta gctctcgtta      780
atggcacggc ggttggatct ggaatggcgt cgatggttct attcgaagcg aatgtccaag      840
cggtgttagc ggaggtttta tcagcgatct tcgcggaggt tatgagcggg aaacctgagt      900
ttaccgatca tctgactcat cgtttaaaac atcatcccgg acaaatcgaa gcggcggcga      960
taatggagca catactcgac ggaagctcat acatgaaatt agctcaaaag gttcacgaga     1020
tggatccatt gcagaaacca aaacaagatc gttacgctct tcgtacatct cctcaatggc     1080
taggtcctca aattgaagta atccgtcaag ctacgaaatc gatagagcgt gaaatcaact     1140
ccgttaacga taatccgttg atcgatgttt cgaggaacaa ggcgattcac ggtggtaact     1200
tccaaggaac accaatcgga gtttctatgg ataacacgag attggcgatt gctgcgattg     1260
ggaagctaat gtttgctcaa ttctctgagc ttgttaatga tttctacaac aatggacttc     1320
cttcgaatct aactgcttcg agtaatccaa gtttggatta tggattcaaa ggagcagaga     1380
ttgctatggc ttcttattgt tctgagcttc aatacttggc taatccagtc acaagccatg     1440
ttcaatcagc tgagcaacat aatcaagatg tgaactctct tggtttgatc tcgtctcgta     1500
aaacatctga agctgtggat attcttaagc taatgtcaac aacgttcctt gtgggatat     1560
gtcaagctgt tgatttgaga catttggagg agaatctgag acaaactgtg aagaacacag     1620
tttctcaagt tgctaagaaa gtgttaacca ctggaatcaa cggtgagtta catccgtcaa     1680
ggttttgcga aaggacttg cttaaggttg ttgatcgtga gcaagtgttc acgtatgtgg     1740
atgatccttg tagcgctacg tacccgttga tgcagagact aagacaagtt attgttgatc     1800
acgctttgtc caacggtgag actgagaaga atgcagtgac ttcgatcttt caaaagattg     1860
gagcttttga agaggagctt aaggctgtgc ttccaaagga agttgaagcg ctagagcgg      1920
cttatgggaa tggaactgcg ccgattccta accggattaa ggaatgtagg tcgtatccgt     1980
tgtataggtt cgtgagggaa gagcttggaa cgaagttgtt gactggagaa aaggttgtgt     2040
ctccgggaga ggagtttgat aaggtcttca ctgctatgtg tgaaggtaaa cttattgatc     2100
cgttgatgga ttgtctcaag gaatggaacg gagctccgat tccgatttgc taa            2153
```

<210> SEQ ID NO 15
<211> LENGTH: 2085
<212> TYPE: DNA
<213> ORGANISM: Arabidopsis thaliana

<400> SEQUENCE: 15

```
atggagtttc gtcaaccaaa cgcaacagca ttgagcgacc cacttaactg gaatgtagcg       60
gcggaggctt taaagggag ccacctggag gaggtgaaga agatggtgaa ggattatagg      120
aaaggaacgg tgcagctagg cggagagacg ctgaccatcg gtcaggttgc ggcagtagcg      180
agtggaggac cgacagtgga gctttctgag gaggctcggg gcggtgtgaa ggcgagtagt      240
gactgggtga tggagagcat gaaccgtgat acggacacat atgggatcac cactggattt      300
ggttcatctt ctcgtaggag gactgaccaa ggtgctgctc ttcaaaaaga gcttattagg      360
tatttgaacg ccgggatatt cgctaccggc aacgaagatg acgacaggtc aaacacgctt      420
ccccggccgg ctactagagc agcgatgctc atccgtgtaa acaccctcct caaggctac       480
tctggtatac gctttgagat cctcgaagcc atcacaacac tcctcaactg caaaattaca      540
ccgctccttc ctctccgagg caccattacc gcctccgggg atctcgttcc gttatcctat      600
atcgctggat tcctcatcgg gcgccccaac tcccgatccg tgggcccctc tggcgagatc      660
```

-continued

| | |
|---|---|
| ctcactgcct tggaggcctt caagctcgct ggagtatcgt cttttttcga actcaggcct | 720 |
| aaagaagggc ttgcgctcgt gaatgggact gcggtggggt ctgctttagc ctctacggta | 780 |
| ctgtacgatg ccaacatttt ggtggttttc tccgaagttg cttccgccat gtttgcagag | 840 |
| gttatgcagg ggaaaccaga gtttaccgat catcttacgc ataaactcaa gcaccatcct | 900 |
| ggtcagatcg aagccgccgc tatcatggag catattctag acggaagctc ttatgtaaaa | 960 |
| gaagctctac atctccacaa gattgatccg cttcagaaac ctaaacaaga tcgttacgct | 1020 |
| ctgcgaacat ctccgcaatg gcttggaccg cagattgagg tgataagagc agcgactaag | 1080 |
| atgatcgaac gtgagataaa ctcagtaaac gataacccctt tgatcgatgt ttcaagaaac | 1140 |
| aaagctatcc atggtgggaa cttccagggg acaccaattg tgtcgccat ggataacact | 1200 |
| cgtctagcac ttgcttctat cgggaagcta atgttcgctc agttcactga actcgtaaat | 1260 |
| gatttctaca caacgggtt accctctaat ctatctggtg gtagaaaccc tagtcttgat | 1320 |
| tacgggttaa aaggcgcaga agtcgccatg gcttcttatt gctcagagct tcagttccta | 1380 |
| gcaaatcctg tgacgaacca tgtcgaaagc gcttctcaac acaatcaaga tgttaactct | 1440 |
| cttgggctga tctcgagccg aacgacagca gaagctgtgg ttatcctcaa gctcatgtca | 1500 |
| acgacttact tggtagcttt gtgccaagcc tttgatctga cacaccttga agaaattctc | 1560 |
| aagaaagcgg ttaatgaggt tgtgagccac actgccaaaa gcgttctagc aatcgaacca | 1620 |
| ttccgcaaac acgacgatat tcttggagtt gtcaaccgcg aatacgtctt ctcctatgtt | 1680 |
| gatgacccaa gcagcctcac taaccccttta atgcagaagc tgagacatgt cctcttcgac | 1740 |
| aaagctttag ctgaaccgga aggcgagacc gacacggttt tcggaaaaat cggagcgttc | 1800 |
| gaggccgagc tgaaatttct cctccctaaa gaagtggaac gagtcaggac agagtacgag | 1860 |
| aacggtacat ttaatgtggc taaccgaatc aagaagtgtc gatcgtatcc gctgtaccgg | 1920 |
| tttgtgcgga tgaactcga gacgaggttg ctaaccggag aggatgttcg gtcaccggga | 1980 |
| gaggattttg acaaagtctt cagggctata tctcaaggaa aactcataga tcctctgttt | 2040 |
| gaatgtctga aagagtggaa cggtgctccg atttctatct gctaa | 2085 |

<210> SEQ ID NO 16
<211> LENGTH: 2124
<212> TYPE: DNA
<213> ORGANISM: Arabidopsis thaliana

<400> SEQUENCE: 16

| | |
|---|---|
| atggagctat gcaatcaaaa caatcacatc accgccgtct cggcgatcc gttgaactgg | 60 |
| aacgcgacgg ccgaagcttt gaagggagc cacctggatg aggtgaaacg aatggtgaaa | 120 |
| gagtatagga agaggcggt gaagttagga ggtgagactt tgacgattgg tcaagtagcc | 180 |
| gccgtggcta aggaggagg aggatctacg gtggagctag cggaggaggc tcgtgccgga | 240 |
| gtcaaggcga gtagcgaatg ggtgatggag agcatgaacc gaggaacgga cagttatgga | 300 |
| gttaccacag ggtttggtgc aacttcccat agaagaacca aacaaggcgg tgcacttcaa | 360 |
| aatgagctta ttaggttctt gaatgccgga atatttggcc ccggcgccgg ggacacgtca | 420 |
| cacacgttgc caaagccgac aacaagagcg gcaatgctcg tccgtgtcaa cactctcctc | 480 |
| caaggctact ccggtatacg cttcgagatt ctcgaagcaa ttacaaagct tctcaaccac | 540 |
| gaaatcactc cgtgcctccc ctcccgtggc accatcaccg cctccggtga ccttgttcct | 600 |
| ctctcttaca tcgccggact tctcactggc cgtcccaact ccaaagccgt gggtccctct | 660 |

```
ggtgagactc tcactgcctc tgaggccttt aagctcgccg gagtatcgtc cttttcgag    720
ctgcagccta aggaaggact agcacttgtg aacgggacag cggttggatc gggtttggcc    780
tcaacggttt tgttcgatgc aaatattttg gctgttttat cggaagttat gtctgccatg    840
ttcgcagagg ttatgcaagg gaaaccggag tttacagatc atcttacgca taagctcaag    900
caccatcccg gtcagatcga agccgccgca attatgaaac atatattaga cggaagctct    960
tacgttaaag aagctcaact tctccacgaa atggatcctc ttcaaaaacc taaacaagat   1020
cggtacgctt tacgtacgtc accacaatgg cttgggccgc agattgaagt gatcagagcg   1080
gctactaaaa tgattgagcg tgagatcaac tctgttaatg ataacccttt gatagatgtg   1140
tcgaggaaca aggcgttgca cggtggaaat ttccaaggga caccgatcgg tgttgccatg   1200
gataattccc gtctagccat tgcttccatt gggaaactca tgtttgcgca gttttctgaa   1260
ctagtgaacg atttctacaa caatggtttg ccttctaatc tatctggtgg gagaaaccct   1320
agtcttgatt acgggtttaa aggcgcggaa atagccatgg cttcttattg ctccgagctt   1380
cagttcctgg ctaatcccgt gaccaaccat gtccaaagcg cagagcagca taaccaagac   1440
gttaattccc tagggctaat tctctagcagg aaaactgcag aagcagtgga tatcctcaag   1500
ctaatgtcca aacctactt agtcgcgctt tgccaagccg ttgatctaag acatcttgaa   1560
gagaatctga agaaggcggt taaatcagca gtgagtcagg tggcgaaacg ggtcttaacc   1620
gttggtgcca acggggagct acatccgtca aggttcacag aacgtgatgt cctccaagtg   1680
gttgaccgag agtacgtgtt ctcatacgca gacgatccct gcagcctcac ttacccgcta   1740
atgcagaaac ttagacacat tcttgtagac cacgctttag cggatccaga acgcgaggcc   1800
aattccgcga catcggtttt ccacaaaatc ggagcttttg aagccgagct gaaactgctt   1860
ctccctaaag aagtagaacg cgtccgggtt gaatacgagg aaggaacatc ggctatagct   1920
aaccggatta aggaatgtcg gtcttatcca ttgtatcggt ttgtccgcga tgagctaaat   1980
actgaactgc ttactggaga gaatgttcgg tcgccaggag aggagtttga taaagtgttc   2040
ttagcgattt ctgatggaaa acttattgat ccgttgttgg aatgtctcaa ggagtggaac   2100
ggagctccgg tttcaatctg ttga                                         2124
```

<210> SEQ ID NO 17
<211> LENGTH: 2145
<212> TYPE: DNA
<213> ORGANISM: Camellia sinensis

<400> SEQUENCE: 17

```
atggatagta ccaccgccat tggaaacggt gtcgggagtg gcggttcacc gggttttgt      60
ctgaaagacc ctttgaattg ggagtggcg gcggaggcaa tgaaggggag tcatttggag    120
gaagtgaagg gcatggtgga ggagtttcgg aagccagtgg tgaggctggg agggagact    180
ttgacgatat cgcaggtggc ggcgatcgcg gtgaggggta gtgaggtggc ggtggagctg    240
tcggagtctg cgagggaggg agtgaaggcc agtagtgatt gggttatgga gagtatgaat    300
aaagggacag atagttatgg tgttactact ggttttggtg ctacttcaca taggaggacc    360
aaagaaggtg gtgctcttca aaaggagctt attaggttct tgaatgctgg aatatttggc    420
aatgaacag agtcatgtca cacattgcca caatcagcca caaggcagc tatgcttgta    480
aggatcaaca ccctcctcca aggatactcc ggcattaggt tcgaaatttt ggaagccatt    540
tccaaattcc tcaacaacaa catcactcca tgcctgccgt tacgcggcac tatcaccgcc    600
tccggtgacc tagtccccct atcttacatt gccgggcttt tgacaggccg gcacaattcg    660
```

```
aaggcggtcg ggcctactgg agaaatcctc cacccccaagg aagccttccg tctagctgga    720
gttgagggcg ggttttttga gttgcaaccc aaggaaggcc ttgcgcttgt caacggcaca    780
gctgttggtt ccggcttggc ttctatggtt cttttcgagg ctaacatact cgccgtgtta    840
tcagaagttt tgtcagcgat tttcgctgaa gttatgcaag gcaagcccga gttcaccgac    900
catttgacac acaaattgaa gcaccaccct ggccaaattg aagctgctgc cattatggaa    960
cacattttgg atggtagctc ttatgtcaag gcagcccaaa aactacatga aatggatcca   1020
ttgcaaaaac caaaacagga cagatatgcc cttagaacat ctcctcaatg ctaggaccac   1080
ctaattgaag tcatccgatc atcgacaaaa tcaattgaga gggagataaa ctcggtgaat   1140 gacaacccctt tgatcaatgt tcaaggaac aaggccttac atggtggaaa tttccaaggt   1200
accccaatcg gagtctccat ggacaataca cgtctagctg ttgcctcaat agggaagctc   1260
atgtttgccc aattctctga gcttgttaat gacttctaca caatgggtt accatcaaat   1320 cttttccgggg gacgaaatcc aagtttggat tatggtttca agggagccga gattgccatg   1380
gctgcttatt gctcagaact ccaattcctt gccaatcctg taaccaacca tgtccaaagc   1440
gccgagcaac ataaccaaga tgtgaactct ttaggcctaa tctcttcaag aaagacagcc   1500
gaggcagttg atatcttgaa gctcatgtcc tctacatatc tagtagcact ctgccaagcc   1560
gtagatttga ggcattttga ggagaatttg aggaacactg tcaagagcac ggtgagccaa   1620
gtagcgaagc gcgttctaac tatgggcgtt aacggagagc ttcacccttc aaggttttgt   1680
gaaaaggact tgctcagagt ggtagaccgt gaatacatct ttgcctacat tgatgaccct   1740
tgcagtgcaa cctacccatt gatgcaaaaa ctaaggcaag tacttgttga gcatgcattg   1800
aaaaatggtg aaagtgagaa gaatttgagc acttcaatct tccaaaagat tagggctttt   1860
gaggaggaaa taaagaccct tttgcctaaa gaggtagaga gtacaagagc agcaattgag   1920
aacgggaatt cggctattcc gaaccggatt aaggaatgcc ggtcttatcc actatacaag   1980
tttgtgaggg aagaattggg aactgaattg ttgaccggag agaaggtccg gtcaccggga   2040
gaggagtttg acaaggtgtt caccgctctg tgcaaggga gatgattga tccattgatg   2100 gattgtctca aggagtggaa tggtgctcct cttcctatct gttag              2145

<210> SEQ ID NO 18
<211> LENGTH: 2062
<212> TYPE: DNA
<213> ORGANISM: Glycine max

<400> SEQUENCE: 18
atggaagcaa ctaatggcca ccaaaacggt tcattttgct tgtccactgc caagggaaat     60
aatgatccct tgaactgggg agcggcggcg gaggcgatga aggggagtca cctggacgag    120
gtgaagcgca tggtggccga gtaccgcaag ccggtggtcc ggctcggcgg agagactctc    180
accatcgctc aggtggccgc cgtggccgga cacgaccacg gcgtggcggt ggagctctca    240
gagtcagcga gagaaggagt aaaggcgagc agtgagtggg tgatgaacag catgaacaac    300
ggcactgaca gttacggcgt caccaccggc ttcggtgcca cgtcacaccg ccgaaccaaa    360
cagggtggtg ctctgcagaa ggaactcatc agattcttaa atcaacactc ttcttcaggg    420
gtactcaggc attagatttg aaatcttaga agccataccc aagctcctga caacaacgt    480 taccccatgt ttggaccttc gtggtacaat cacagcttct ggagatcttg ttccactttc    540
ttacattgct ggtttgctaa ctggcagacc caactccaaa gctgttggac cttctggaga    600
```

```
agtacttaac gcaaaagaag cttttgaatt ggctagcatc aactctgagt tctttgaatt      660
gcaacccaag gaaggtcttg cccttgttaa tggcactgct gttggttctg gattagcttc      720
tatggtactc tttgaggcta atatactagc tgtgttgtct gaagttctat cagctatttt      780
tgctgaagtg atgcagggga aacctgaatt cactgaccat ttgacacaca agctaaagca      840
ccatcctggt caaattgagg ctgctgctat tatggagcat atcttggatg aagttccta       900 catgaaagct gctaagaagt tgcatgagat tgatcccttg caaaagccaa aacaagatag      960
atatgccctt agaacttcac cacagtggct tggtcctctt attgaagtga ttcgtttctc     1020
aaccaagtca attgagagag agatcaactc tgtgaatgac aaccctttga ttgatgtttc     1080
aaggaacaag gcattgcatg gtggcaattt ccaaggaacc cctattggag tctctatgga     1140
caacacacgt ttggcacttg catctattgg caaactcatg tttgctcaat tctctgagct     1200
tgtcaatgac ttttacaaca atggattgcc ttcaaatctc actgctagca gaaatccaag     1260
cttggactat ggtttcaagg agctgaaatt gccatggctt ccttactgct ctgaactcca     1320
atatcttgca aatccagtaa ctacccatgt ccaaagtgct gagcaacaca accaggatgt     1380
caactctttg ggcttgatct catctagaaa gacaaatgaa gccatcgaga tccttaagct     1440
catgtcttcc acattcttga ttgcactttg ccaagcaatt gacttgaggc atttagagga     1500
gaatttgaaa aactcggtca agaacaccgt gagccaagtt tccaaaagga ttcttaccac     1560
aggtgtcaat ggagaactcc atccttcaag attttgtgag aaggatctgc taaaagtggt     1620 tgataggggag tatatatttt cctacattga tgacccctgc agtgctacat acccattgat     1680
gcaaaaactt aggcaagtgc ttgtagatca tgcattggta aatgcagagt gtgagaagga     1740
tgtgaactcg tccatctttc aaaagatagc aatctttgag gaagagttga gaatctctt     1800 gccaaaagag gttgaaggtg caagggctgc ttatgagagt ggcaaagctg caattccaaa     1860
caagatccaa gaatgcagat cttacccact gtacaagttt gtgagagagg aattagggac     1920
tgggttgcta actggagaaa aggtgaggtc accgggtgaa gagtttgaca aattattcac     1980
agcaatgtgc caagggaaaa ttattgatcc tcttatggag tgccttgggg agtggaatgg     2040
agctcctctt ccaatctctt aa                                               2062
```

<210> SEQ ID NO 19
<211> LENGTH: 2488
<212> TYPE: DNA
<213> ORGANISM: Zea mays

<400> SEQUENCE: 19

```
aggaattcgg cacgaggccc actcctccgg ctcttcttct ccaccggcac cagtccacca       60
cctcccacct cctgccaccg cgcggccccca accaaccaca ccgcagcgca gcaatggcgg     120
gcaacggcgc catcgtggag agcgacccgc tgaactgggg cgcggcggcg gcggagctgg     180
ccgggagcca cctggacgag gtgaagcgca tggtggcgca ggcccggcag cccgtggtca     240
agatcgaggg ctccaccctc cgcgtcggcc aggtggccgc cgtcgcctcc gccaaggacg     300
cgtccggcgt cgccgtcgag ctcgacgagg aggcccgccc ccgcgtcaag gccagcagcg     360
agtggatcct cgactgcatc gcccacggcg gcgacatcta cggcgtcacc accggcttcg     420
gcggcacctc ccaccgccgc accaaggacg ggcccgcgct ccaggtcgag ctgctcaggc     480
atctcaacgc cggaatcttc ggcaccggca gcgacgggca cacgctgccg tcggaggtca     540
cccgcgcggc gatgctggtg cgcatcaaca ccctcctcca gggctactcc ggcatccgct     600
tcgagatcct cgaggccatc acgaagctgc tcaacaccgg tgtcagcccc tgcctgccgc     660
```

-continued

```
tccggggcac catcaccgcg tcgggcgacc tggtcccgct ctcctacatc gccggcctca    720
tcacgggccg ccccaacgcg caggccgtca ccgtcgacgg aaggaaggtg gacgccgccg    780
aggcgttcaa gatcgccggc atcgaggcg gcttcttcaa gctcaacccc aaggagggcc    840
tcgccatcgt caacggcacg tccgtgggct ccgcgctcgc ggccaccgtg atgtacgacg    900
ccaacgtcct ggccgtcctg tcggaggtcc tgtccgccgt cttctgcgag gtcatgaacg    960
gcaagcccga gtacacggac cacctgaccc acaagctgaa gcaccacccg ggtccatcg    1020
aggccgcggc catcatggag cacatcctgg atggcagctc cttcatgaag caggccaaga   1080
aggtgaacga gctggacccg ctgctgaagc ccaagcagga caggtacgcg ctccgcacgt   1140
cgccgcagtg gctgggcccc cagatcgagg tcatccgcgc cgccaccaag tccatcgagc   1200
gcgaggtcaa ctccgtgaac gacaacccgg tcatcgacgt ccaccgcggc aaggcgctgc   1260
acggcggcaa cttccagggc accccatcg gcgtgtccat ggacaacgcc cgcctcgcca   1320
tcgccaacat cggcaagctc atgttcgcgc agttctccga gctcgtcaac gagttctaca   1380
acaacgggct cacctccaac ctggccggca ccgcaacccc cagcctggac tacggcttca   1440
agggcaccga gatcgccatg gcctcctact gctccgagct ccagtacctg ggcaacccca   1500
tcaccaacca cgtgcagagc gcggacgagc acaaccagga cgtgaactcc ctgggcctcg   1560
tctcggccag gaagaccgcc gaggcgatcg acatcctgaa gctcatgtcg tccacctaca   1620
tcgtggcgct gtgccaggcc gtggacctgc gccacctcga ggagaacatc aaggcgtcgg   1680
tgaagaacac cgtgacccag gtggccaaga aggtgctgac catgaacccc tcgggcgagc   1740
tctccagcgc ccgcttcagc gagaaggagc tgatcagcgc catcgaccgc gaggccgtgt   1800
tcacgtacgc ggaggacgcg gccagcgcca gcctgccgct gatgcagaag ctgcgcgccg   1860
tgctggtgga ccacgccctc agcagcggcg agcgcggagc gggagccctc cgtgttctcc   1920
aagatcacca ggttcgagga ggagctccgc gcggtgctgc cccaggaggt ggaggccgcc   1980
cgcgtggcgt cgccgagggc accgccccg tggcgaaccg gatcgcggac agccggtcgt   2040
tcccgctgta ccgcttcgtg cgcgaggagc tcggctgcgt gttcctgacc ggcgagaggc   2100
tcaagtcccc cggcgaggag tgcaacaagg tgttcgtcgg catcagccag ggcaagctcg   2160
tggaccccat gctcgagtgc ctcaaggagt gggacggcaa gccgctgccc atcaacatca   2220
agtaaaagaa cgccaaggag aagaggaggg aggggaggaa atacgtgaaa aaaaataaaa   2280
cctgtacacg tgtctgtcca gatcgtgccg tcgatcgctc ttcgttgttg attttttggtt   2340
gtattgatcg atccgtatgt gtgcgtgcgt gtgtggcgtt gctctttctt cttttgtgta   2400
gctgtgccct gccaccggcc gacgtgcgtg catgccatgg tggcgggcag cgttttctaa   2460
ggtcatatac tgttgttgtg tttaagta                                      2488
```

<210> SEQ ID NO 20
<211> LENGTH: 2435
<212> TYPE: DNA
<213> ORGANISM: Pinus taeda

<400> SEQUENCE: 20

```
atggtagcag cagcagaaat aacgcaggcg aatgaagttc aagttaaaag cactgggctg     60
tgcacggact tcggctcgtc tggcagcgat ccactgaact gggttcgagc agccaaggcc    120
atggaaggaa gtcactttga agaagtgaaa gcgatggtgg attcgtattt cggagccaag    180
gagatttcca ttgaagggaa atctctgaca atctcagacg ttgctgccgt tgctcgaaga    240
```

-continued

```
tcgcaagtga aagtgaaatt ggatgctgcg gctgccaaat ctagggtcga ggagagttca      300
aactgggttc tcacccagat gaccaagggg acgatacct atggtgtcac tactggtttc       360
ggagccactt ctcacaggag aacaaaccag ggagccgagc ttcagaagga gctgatccgc      420
ttcttgaatg ccggagttct tggcaaatgc ccagaaaatg ttttgtccga agatactacc      480
cgggctgcca tgctggttcg gacgaatact ctgctgcagg gctactcggg cgtaaggtgg      540
gacattcttg aaactgtgga gaagctgttg aatgcgtggc tgaccccaaa gctgcccttta     600 agaggaacca taactgcttc tggtgatctg gttcccctgt cttatattgc tgggctcttg      660
accgggaggc ctaattccag agtcagatcc agagatggaa ttgaaatgag cggagccgaa      720
gcgctcaaga agtgggcct ggaaaagccc tttgaattgc agcctaaaga aggtctagcc       780
attgtcaatg gcacttcagt gggagcagca ctggcttcca ttgtgtgttt cgatgccaat      840
gttcttgctc tgctctctga agtaatctct gccatgttct gcgaggttat gaatgggaag     900
cctgagttta cagatccatt aactcacaag ctgaagcacc atcctgggca aatggaagct     960
gcagcgatca tggagtatgt cttggacggg agttcttata tgaaacacgc tgctaagctc     1020
catgagatga atcctctgca gaagccaaag caggatcgct atggccttcg cacttcgcct     1080
cagtggctcg gccctcaggt ggagattatc agatctgcaa ctcacatgat tgagcgggaa     1140
atcaattctg tgaatgacaa tccagtaatt gatgttgcca gagacaaagc tctacatgga     1200
gggaatttcc agggcacacc tattggtgtt ccatggata atcttcgtct gtcaatttca      1260
gcaattggga aattgatgtt cgctcaattc tcagagcttg tgaatgatta ctacaatgga     1320
ggcttgcctt cgaatctaag tggcgggcct aatcccagcc tggattatgg actgaaaggg     1380
gccgagatcg ctatggcttc ttacacttct gagcttcttt acctggcaaa tcctgtcacc     1440
agccatgtac agagcgccga acagcataac caggatgtca attctctggg tctcgtttca     1500
gctagaaaat ctgccgaggc catcgatatt ctgaagctga tgctctccac atacctgaca     1560
gctctgtgcc aggctgtgga tttaaggcat ctggaggaaa acatgctggc cactgtgaag     1620
cagattgttt ctcaggtagc caagaaaacc ctgagcacag gctcaacgg ggagcttttg      1680 ccaggccgtt tctgcgaaaa ggatttgctc caggtagtgg ataacgagca tgttttctct     1740
tacattgacg atccgtgcaa tgccagctac ccattgactc agaaactgag aaacatcctg     1800
gtggaacatg ccttcaagaa cgcagaaggt gagaaggatc ccaacacttc cattttcaat     1860
aagattcctg tgtttgaagc cgagctgaag gcacagcttg aaccgcaagt tagtctggcc     1920
agagaaagtt atgacaaagg gaccagccct ctgcccgaca ggatccagga atgcaggtct     1980
tatcctctct atgaatttgt gagaaaccag ctcggtacca agcttctgtc tggaactcgt     2040
accatttccc ctggtgaagt gattgaagtg gtttacgacg ctatcagtga ggacaaggtc     2100
atagtccctc tcttcaaatg cttggatggg tggaaaggaa ctctggccca ttctgaaata     2160
aataatcttc caagatcgcc tttatacaac gactgctatg atttgagtcc tcggatgctt     2220
ttgttgatgc tgttgttttc cgatccggaa tttgattggt cataaagctt gattttgttt     2280
ttctttcttt tgttttatac tgctggatct gcatcccatt ggatttgccg gtgccagaaa     2340
tatgtaaggg tggcagatca tttgggtgat ctgaaacatg taaaagtggc ggatcatttg     2400
ggtagcatgc agatcagttg ggtgatcgtg tactg                                2435
```

<210> SEQ ID NO 21
<211> LENGTH: 2044
<212> TYPE: DNA
<213> ORGANISM: Persea americana

<400> SEQUENCE: 21

```
gaattcggca cgagctaatc aggcttggcg gcgcatcgct gacaatatct caggtggccg      60
ccgtcgccta tgagccggag gtcagggtgg agttgtctga gtcggcgcgc gccggggtca     120
aggcaagcag tgattgggtg atggagagca tggacaaggg gacagacagc tatggagtca     180
ctacagggtt tggtgcaact tcccacagga gaaccaagca aggaggagcc ctccacaagg     240
agcttataag attcctcaac gctggaatct ttggcaccaa tggagaatcc ggccacacat     300
tggcaccctc tgccaccagg gccgccatgc tggtgcgaat caacactctc ctccaaggct     360
actctggaat ccgattcgaa atcttggaag caatcacaag cctcctcaat cacagcatca     420
ccccatgttt gccactcagg ggaacaataa ctgcatctgg tgatctagtc cccttatcct     480
acattgctgg aatgttgacc ggtcggccta atagcaaagg cgattggcct gatgggaaag     540
agattgatgc aggagaggcc ttccgtctag caggaattcc cagtggattc tttgaattgc     600
agcctaaaga aggccttgca cttgtcaacg gcactgcagt cgggtctggg ctagcttcga     660
tggtgttgtt cgaagcgaat gttctctcag tcctatcgga agttatccg gccatcttct      720
gtgaggtaat gcagggaag ccagagttca cagaccatct tactcacaag ttgaagcatc      780
atccgggcca aattgaggct gcagccatca tggaacacat cttagatggg agctcttaca     840
tgaaggttgc aaagaagctt catgagcttg acccgctcca aaagccaaag caagacccgt     900
acgccgccct ccgaacttct ccccagtggc ttggtcccca aatagaggtg atcaggaatg     960
ccacactctc aattgagagg gagatcaact cagtcaatga caacccattg atagacgttt    1020
cgaggaacaa ggcgctccat gggcggaact tccaagggac cccaattggg gtgtcaatgg    1080
acaacaccag attagcgatc gctgcgattg ggaagcttat gtttgcacag ttctctgagc    1140
ttgtcaatga tttctacaac aatgggttgc cttcaaatct ctcaggggga cggaacccga    1200
gcttggatta tgggttcaag ggagctgaga ttgcaatggc agcctattgc tcagagctcc    1260
aattcctggc taatccagtg accaatcatg ttcaaagcgc agagcagcac aaccaagatg    1320
tgaactccct ggggttgatc tcttcaagga aaacagctga agctgttgag atcttgaagc    1380
tcatgtcatc tactttctctt gttgggcttt gccaggcaat tgatttgagg catttggagg    1440
agaatttgaa aagcacagtc aagaacactg tgagtcaagt ggccaagaga gttctaacaa    1500
ttggtgtaaa cggagagctc cacccatcga ggttctgcga aaggacttg atcaaggttg     1560
ttgatggtga gcatctattt gcttacattg atgacccatg cagctgtacc taccctctga    1620
tgcagaagct aaggcaagtg ctggtcgaac acgcgctgat caatggagag aaggagaagg    1680
attcaagcac atcaatcttc caaaagatag gtgcttttga agaggagctg aagacccatc    1740
tgccgaaaga agtagaaagc gcaaggattg agcttgagag aggtaattca gctatcccaa    1800
ataggatcaa ggaatgtagg tcctatcctt tgtacaagtt tgtgagggag gagctcaaga    1860
cgagcctgct gacgggtgag aaagtccggt cgccgggtga ggagttcgac aaggtgttct    1920
cagcgatttg ccaagggaag gtaattgacc cccttctaga gtgtctgaga gagtggaatg    1980
gtgctcctat tcccatttgc tagaaccagc gagtaaaatc aaataatctt ctatgtttgc    2040
ttca                                                                 2044
```

<210> SEQ ID NO 22
<211> LENGTH: 2335
<212> TYPE: DNA
<213> ORGANISM: Ipomoea batatas

<400> SEQUENCE: 22

```
acgcagtgaa ggtgcaagaa taatggccaa ccaaaatggc ttctgtatca agaagcagca      60
ggttgatcct ttgaactggg agatggctgc cgagtcattg aggggagcc acttggatga     120
agtgaaacgc atggtggccg agtttaggaa gccggcggtg aagctcggcg agagacgct     180
cacggtggct caagtggcac gtatcgcctc ccgtgacaat gccgtcgcgg tggagctctc     240
cgaggaggcc cgggccggcg ttaaggccag cagtgattgg gtgatggata gcatgaacaa     300
agggactgat agctacggcg tcaccaccgg cttcggtgcc acctctcacc gtagaaccaa     360
acaaggtggc gctcttcaga aggagctcat taggttttg aatgctggaa tattcggcaa      420
tgcaacagaa tcgtgtcaca ctcttcccca ttcagcaaca agagctgcca tgcttgtgag     480
aatcaacact cttcttcaag gatactctgg cattagattt gaaatcttgg aagcaatcac     540
taaattgctg aaccacaaca ttacccctg cctgccctc cgtggcacca tcaccgcctc       600
cggtgacctt gtcccgttat cctacattgc tggcttgatc accggccgcc ctaactccaa     660
ggccgtcgga cccaacgggg agaccctcaa cgcagaggaa gctctgcggt taagccggag     720
tggacggagt attttcgag ttgcaagccc aaggaagggc ttgccctcgt taatggcacc      780
gccgttggtt ctaggcatgg cctctatggt tcttttcgag gctaatgttc ttgcagttct     840
gtctgaggtt ttatccgcta tttttgctga agtcatgaat gggaaaccag aatttaccga     900
ccatttgacg cataagttga agcatcaccc cggccagatt gaagctgctg ctattatgga     960
acatattttg gacggcagct cttacgtgaa ggcggctcag aagttgcacg aaatggatcc    1020
tctgcagaaa cccaaacagg atcgctatgc tctccgcact tcgccccaat ggctcggccc    1080
tcagattgaa gtcattcgtg ctgcaaccaa aatgattgag agggagatca actctgtcaa    1140
cgacaaccct ctcattgatg ttgccagaag caaggccttg cacggtggca acttccaggg    1200
tacaccaatt ggtgtgtcta tggacaactc aagattagcc cttgcatcta tcggcaagtt    1260
gttgttttgcc caattctctg agcttgtcaa tgactattac aacaatgggt tgccttctaa    1320
tctcacagca gggaggaatc caagcttgga ttatggtttc aagggcgctg aaattgccat    1380
ggcttcttac tgctccgagc tgcaattttt ggctaatccg gttactaacc atgtccagag    1440
tgctgagcag cacaaccagg atgttaactc cttgggtttg atctcagcta ggaagactgc    1500
tgaagctgtg gacgtgttga aactcatgtc atccacatat ctcgttgcgc tttgccaagc    1560
tattgacttg aggttcttgg aggagaactt gaggaatgct gtgaagaatg cagttacaca    1620
ggtagctaag aggactctca ctgtgggtgc taatggagaa cttcatcccg caaggttttg    1680
cgagaaagac ttgctccgag tggtggaccg cgaatatgtc ttcgcatatg cggatgatcc    1740
ctgcagtgct aactacccgc tgatgcagaa actccgccaa gcccttgttg atcacgcctt    1800
gcagaatggg gagaatgaga agaacaccgg cacttcaatt ttcctaaagg ttgcagcttt    1860
tgaagatgaa ttgaaagctg ttctgccaaa agaagttgag gctgcaagga tcgctgtaga    1920
gagtgggaac ccggctattc aaacaggat taaggagtgc aggtcttacc cattgtacaa      1980
gtttgttcgt gaaggcctgg gcactgagtt gctgaccgga gagaaggtcc ggtcaccggg    2040
cgaagagtgt gacaaggtgt tcacagctat gtgtgaggga agtatcattg atcctttgtt    2100
ggaatgcctt aagagctggg atggggctcc tcttcctatc tgttaattta tttcaattca    2160
ttgcttattt tcaatgtaat atatacattt tttcctcgg ttatgctact tgaacattgt      2220
tttggctttt ggtaaaatcc agttgtaatc ttttctggaa tgcttctctc tgtagggatg    2280
tagctacatg tgcttttctg ttcagtaaaa gatgaatgag taggcactgt tgtgg          2335
```

<210> SEQ ID NO 23
<211> LENGTH: 6306
<212> TYPE: DNA
<213> ORGANISM: Nicotiana tabacum

<400> SEQUENCE: 23

```
gatccggaca agaatgcaaa gtttatcaaa tttatagaat agcctttctt tctcttaaca     60
atttaaaatt agggaccaat aaagaaaaat cacaatagga aatatgtaca ttagaattat    120
ttcctttcac ttcgctccaa ctagaattca ttcattcata ctgaaaaaaa tttaaattta    180
aaatttcaat atcaataaaa aatttcgctg tcaataataa tatgaatctt aacacttgtt    240
tatggaacaa caaactaggg tcttataaag agagaacgat atctacttat atttggaaag    300
ttatggtgat agttttaatt tgaaatttat cgtgctcttt tattcaaact aaataacgat    360
atatttagct cggttgtacg gatattttaa aatttatcct tacgagaaat taaatcgtaa    420
aatacaaaaa aatacaaaca tatattgaag tagattttat atttctacgg aaagattata    480
tttttgctag ttcattaatt acagattgag tcaaaataaa ttcttggata atccttcatt    540
tattgaaaca cattaaaaac aactccattt taaaagagga aaagagttga atttacaatc    600
ttaacccctc aattttctcc caacaaccca aacaactcta accttctccc aaatccacca    660
accaacccaa acattttttt tttcatttta ttttttaaca aataaataaa taaataaacc    720
catgttgcat gaagtaccca cgtcagtctc aaatctcaac cgttaattac acctaaaatc    780
aagggctaaa attaatctac caacaaccac catttagtct tctttgttac aaccccctcac    840
tatattttct ttacctacca acatttgagt tccattcccc tctatttata caccacatct    900
cctatctacc actcctcaaa aaaacaagaa aaaacaattt caattcttag ccattttctc    960
ttctccaaat ctcctcacaa cctttaacat ttctagccaa ttctttattt tctagccaat   1020
tcttgatcaa acaatggcat caaatggtca tgttaatgga ggagaaaact ttgagttgtg   1080
caaaaaatca gctgatccat tgaattggga aatggcagct gaatccttaa gagggagtca   1140
tttggatgaa gtgaaaaaaa tggtgagtga atttagaaaa ccaatggtaa aacttggtgg   1200
tgaaagttta acagtggcac aagtggctgc tattgctgtt agggacaaaa gtgcaaatgg   1260
tgttaaagtt gaacttttctg aagaggcaag agctggtgtt aaagctagta gtgattgggt   1320
tatggacagt atgaataaag gaactgatag ttatggtgtt actactggtt ttggtgctac   1380
atctcatagg agaaccaaga atggtggtgc tcttcaaaaa gaacttatta ggtaaaccac   1440
ttttcatcta cttaactttg ctttctgcac cagaatttta atattttgtt tcctcctaaa   1500
gattttttatc gttaagtgtg ttaaataatt taaattaatt attttcaaga tatacgagtt   1560
tattatacac aagatttctg tcagaagttt gcagtgaccc ttagtccgaa aaaataata   1620
gcatctacat ttttctatga cagcgttaag gaaattttac acggtcagta gaaaggtta   1680
ttttacgtta ttattttagt ttattgtaag cagctatata tatatatata tatatatata   1740
tatatatata tatatatata gttatgtttt agatggtcgt aaatttattt tgtgttgacc   1800
atgtatagta atagttaaat tcttattctg caagaaaatc tgactagcat ttatgagtta   1860
atgatctact attttgagtt aataactatt aatgatatat actaatttga ccttataaaa   1920
aaattatcta ttatttgag tcaatagtta ttaatgattt actttaactc ttatgtcaac   1980
tactctttt gtaagaggaa atgagttta aatgatatca actttaaggt aaaatgtgta   2040
cattttctat gtaatctaaa cgattatagc agctatattt caagttatta tttccgacca   2100
```

```
aatatgaaaa gtctcttatt attatagaac aatataatct ggtactataa attttcttta    2160
ttttatcata gtagagaaga taaagtttgt atatgtaaac atttatcaca cgcgctagac    2220
caagaactaa gtactttaga tttacatctt gaaatttgaa ttattgagta aagaaaaata    2280
ttaaatagcc cttggaaaaa tattttatat tggaacttga tacgaagtac aggaattttg    2340 catctcatc tataaatcta attatataaa ttaaattttg tacaactgta aaaaaaaaac    2400
aagccactag tttgactttt gttgggttgg aaaaagagtg tgtggttggt ggaggagatt    2460
ttagtcattt caccttcctt ctagttttgt ataaagtaca tgtaagaatt tattcagtaa    2520 attttccta ctactatttt cctaaattta gtaagaaaaa ataatttaaa taaacatctt    2580
taaatagtta aattatttt gtgggtcctc aaataataga tgagagacaa gtgggcttat    2640
ttaaacagtt taaatttcca actatttggg tcgaatccca gtagtcccat gtgctgtctc    2700
ttgtcagata tctatttatt ttaaagtaca aataattttt aaaacaaata ttgcataaat    2760
aagtaatttt atacttattt aaagagaatt gttaaaaaaa ttatgaaatg acaattttaa    2820
atctcaaatt taaacttcac ttttattttt gggcctaatt tacctttaac ctgcaccgaa    2880
actatttata tctgatagct acaaaagtgt ataaacttta tatattttt tatacaacat    2940 acatatatat atatacaaaa atatatatat attttcgctt attattttat tagcggctat    3000 gtcattttt tcctttttc atttccct cccctgccca caaggccaaa aatataacaa    3060
atgtgtgccc cactttaaag gggctttata tcacttgaaa tgatgggagt tgatgtaaca    3120
cactacaagg ttttcttttt tttttcttaa gccttataat tcttgatccc tattctagtc    3180
attttctcgt actaaacaat aatatatcca atataatctc atactaattt tctcatagac    3240
cctcggctaa ttttctcata ctagtaattt ttaaatatcg tcacaaagta gataggacaa    3300
agtacaaata aaacatgttc ttatttaaat ttggttggta caattcagtt caatagctga    3360
tgttgttgac attgaattgg caggttcttg aatgctggtg tttttggcaa tggaacagaa    3420
acaagccaca cattgccaca ttcagcaaca agggcagcta tgcttgttag gatcaacaca    3480
ctcctacaag gctactctgg catcagattt gaaatcttgg aagctattac aaaattgatt    3540
aacagcaaca tcactccatg tttacctctc cgtggaacga tcactgcctc gggtgatctt    3600 gtcccttat cctacattgc tggttttgctc actggtaggc taattccaa ggctgttggt    3660 cccaatggtg agacacttaa tgctgaagaa gcgttccgcg ttgctggtgt taacggtgga    3720
tttttcgagt tgcagcctaa ggaaggactt gcacttgtga atggtacagc tgttggttct    3780
ggtatggcat caatggtcct ctttgattcc aacattcttg ctgtaatgtc tgaagtttta    3840
tcagcaattt tcgctgaagt aatgaacgga aagcccgaat tcactgacca tttgacacac    3900
aagttgaagc accaccctgg tcaaattgag gctgctgcta ttatgaaaca tattttggat    3960
ggaagctctt atgtgaaggc ggctcaaaag ctacatgaaa tggatcctct acaaaaacca    4020
aagcaagatc gttatgctct ccgaacatct ccacaatggc ttggccctca aattgaagtc    4080
attcgcgctg caactaagat gattgagagg gagattaact cagtgaacga taacccttg    4140 atcgatgttt caagaaacaa ggcgttacat ggtggcaact ccaaggcac tcctatcggt    4200 gtttccatgg ataatgcaag attggctctt gcatcaattg ggaaattgat gtttgctcaa    4260
ttctcggaac ttgtcaacga ctattacaac aacggtttgc cctctaatct cactgcatca    4320
aggaatccaa gcttggacta tggtttcaag ggagctgaaa tcgccatggc ttcttactgc    4380
tcagaacttc aattcttggc aaatccagtg acaaaccatg tccaaagtgc tgaacaaac    4440 aaccaagatg tcaactcctt aggcttaatc tcagcaagga aaacagctga agctgttgat    4500
```

```
atcttaaagc tcatgtcatc aacttatctc gtggcacttt gccaagctat agacttgagg    4560
catttggaag aaaacttaaa gaatgcagtc aagaacacag ttagccaagt agctaagaga    4620
actcttacaa tgggtgctaa tggtgaactt catccagcaa gattctgtga aaaggaattg    4680
cttcgaatcg tggataggga atacttgttc gcctacgctg atgatccttg cagttgcaac    4740
taccctttaa tgcagaaact gagacaagta cttgttgatc atgcaatgaa taatggtgaa    4800
agtgagaaga atgtgaacag ctcaatcttt caaaagattg gagctttcga agatgaattg    4860
aaggctgttt taccaaagga agttgagagt gcaagagctg cattagaaag tggaaaccct    4920
gctattccta acaggattac agaatgcaga tcttatccat tgtacaggtt tgtgagaaag    4980
gagcttggaa cagaattatt gacaggagaa aaagtccgat caccgggcga ggagtgtgac    5040
aaagtgttca cagcaatgtg caatggacaa atcattgatc caatgttgga gtgtctcaag    5100
agctggaatg gtgctcctct tcctatctgt tagttgtttg cttgatttcg cgcggcggga    5160
acttttgtta atgtttgtca attgctattt ttcagattct ttttttactc tttggtgaat    5220
tactatcata atatgttgtg aacttatagt ttttggtta acttaaaaag agtgttagaa    5280
ctcttttaaa tatgttggat tgtagctgta aatgtctctt ttcagtataa acctaatgaa    5340
aagtgacagt gtgcttaaat cttactggca agtcttcttc tgttcaatct gttcctcttt    5400 cttttttctat tcaattcttc atcttaagta gggaatgttc agtaagcata tggaacacta    5460
ctcaaatcac caaaaactgt attccccata tgttactctg tcctcttaaa agaatagaat    5520
actaattgca agttttttaga gattttttcga aaatgagttt ttcaaaaact aaaaagtaat    5580
tttaatcaat tttccaaatt tttcggaatt ttttttccac tcttaaaatt gtaatatttc    5640
ttttcaactg aaattcacgt ccaaacataa ttttaaattc caaatatcac tcttattttt    5700
tttacattat atttttttgt ccaaacgctt actaaatata taaacaaac tattaaggga    5760 tggctgatga tttccaaatt aaaggaatat aaattgatga aattgtcgtt gatatgtctg    5820
aaacaaatga tcctaagcac aaggtaaaga tggaaattaa aaaattacaa cacatcatca    5880
atactgttat aagtggcata aaatctgtaa aatttaacac gctcattagg aaaatcacta    5940
ataaataagt attaagacaa tttccagtaa ttattgacac aagaaagaaa taagtacaat    6000
attacgttac caatgaggag acattaaaaa tcttaacacg tcatgtcatg tcactttagg    6060
aaagtcccat tcatgtcaat tatttgattt ttttttttcta ggaaagttaa aaagaaaaga    6120
gaacacaata aacatttctt attttttgtta taaatctgga ttgttgtaat aaacaattaa    6180
atcattaaac ttttttgaaat atataaacaa aacagaaagt tagtaatact tgtttaacga    6240
aataaatttt agaaaacag tataggaata atcgatacc agtggaatac acagtgtgtc    6300
cttaag                                                                6306
```

<210> SEQ ID NO 24
<211> LENGTH: 5603
<212> TYPE: DNA
<213> ORGANISM: Nicotiana tabacum

<400> SEQUENCE: 24

```
gtcgacctgc aggtcaacgg atcggttctc tcctaaaaag atactaaatt aattaagtca      60 atttttaaa tattaaaacc aatccaaacg aattaattcg atctttttatt ggttaggttg     120 ttgatttatt cgattttcgt cgatttattt tcttaaatat gagacatata tggtcaagca     180
catagtatgg tgattatatt ccaacatatt tatccaacca attaatcttt gagaaagtct     240
```

```
ttcattttc    aagatatctt    gataataatt    gaattgtata    gtgatgaata    atgtaagaat       300
tcaattaaag    acaagttatt    tttaatatga    tataaactct    tgaacttagc    aaaataaagg       360
tattttattt    tatagtatgt    agttggtttg    atttagattt    tttgcgatta    ttttcgctt        420 taaatcaaat    ttggtcggtt    tttaaaatcc    aaaaccaaat    caagccatca    aatattttg        480 ttagtttgat    tttttcagtt    tttcataaac    actggtgttt    gaaagaaaaa    gaagtctttt       540
tttctatttg    agttaaaatt    tacaaggatt    ctttcaacaa    tccaaacaac    ccctttcgca       600
aattcaccaa    cccccaacta    ttgaaggatc    caaatctaat    tacaaatccc    taattttatc       660
ccattttaat    tagtgtttca    acacccaaa     agcaccaaac    cttttcttca    aatccaccaa       720
cccccaaaac    ttttgaaagt    catgttgcat    cctttaccca    cgttgtttt     atatctcaac       780 cgctcattac    attttaatc     caacggtcca    tattaatctt    ccctatgtt     cacctaccaa       840 ggaattgttc    acacattaat    caacgattc     atattaatca    tttaagggt     ccctaattat       900 gttcacctac    caaacattat    acccatccct    ctatttatac    cacaattctt    agcttcaata       960
accaggatct    ttctacccat    cctcacattt    aattaataac    ccaattcttg    tttccaaaaa      1020
tataccttca    atttttcact    agacaaacca    accccttac     actttactc     cattttcttg      1080 aatcatttca    tttcatttca    tctacacaaa    aaaaaatggc    tggtgttgca    caaaatggtc      1140
accaagaaat    ggattttgc     atgaaagtgg    atccattaaa    ctgggaaatg    gcagctgatt      1200
cattgaaagg    aagccattta    tgatgaagtga   agaaaatggt    ggctgagttt    aggaaaccag      1260
tagtgaaact    tggaggtgag    actttgacag    tggctcaagt    tgcggctatt    gctgcaaaag      1320
ataatgttaa    aactgttaaa    gtggagcttt    ctgaaggggc    aagagctggt    gttaaagcta      1380
gcagtgattg    ggttatggac    agtatgggta    aaggaactga    tagttatggt    gttacaactg      1440
gctttggtgc    tacttcacat    aggaggacca    agaatggtgg    tgctcttcaa    aaggaactta      1500
ttaggtaaac    cacttcacat    ctaacttaat    tttgcttcac    atactatagt    aatattttac      1560
tcttttaagt    aggtttatat    ctctcaacga    gagcttggct    caactggtca    tgagtttgag      1620
cagtgaaaat    agtcttttg     taaaaataaa    gtttaagacc    gtgtaccata    gacccgtccg      1680
gccctttccg    gacccacact    taggggagct    taatgcaccc    gttttagta     tgttgtgttg      1740 aaggtttagt    gaaaaactga    cagatgttat    gaattttaca    tgttcttatg    ggaaaatata      1800
ggaatttgtt    attcttagat    aatttgacag    aaatggacag    aaaaataaga    tgttgacaaa      1860
aaggctagca    gaaaattatc    ttaatataca    gcaagcatgt    tactattgtt    atttgtaagt      1920
gattgttatt    agtgtttgat    tcttatctgc    tgtcttataa    tttgaaagtg    ccaacattgt      1980
ttacatttat    agaacatagt    tagaaccttt    tcaaaacaat    tactatgttt    tttctttaca      2040
aaaaagtact    actcctatgt    cttttgatt     aacaaccact    tctatattac    aaaactgtcc      2100
ataagttttt    gcaaacagga    agaaaaggtc    aatatttga     cgtggtaaac    agacaaagaa      2160
tttcatttct    ttgtgctaaa    agtatattac    taacaaaaag    tagctgacta    accttctgt       2220 gcataaactc    ctgagtgtaa    attaaggaaa    taggtggatg    tagccctgta    gggtaaaaaa      2280
aagtggataa    atattcaccc    gcacccaaat    atatatttat    tcctgattaa    ccttaagaac      2340
caataaaacg    aagtaaaaat    acataattac    aacagcaaca    acaatcaatt    tagtctcgta      2400
agtgagggtt    gagaagggta    aactgtaaat    acactttacc    cataccttta    aaaggaaaag      2460 aatttattt     tgatataccc    tcaactaaaa    atacataatt    aagtgtttaa    aaaatgtaat      2520
atgctaaaca    tatgttttat    ataaattgat    tttgtgtaaa    aattggaagg    aaataagttt      2580
ttacctagta    gtgtgtggtg    ccccagctgg    agccattcag    agacgagtta    agtgacatgt      2640
```

-continued

```
gggcacgtgc agacagttta gcctttccta cattttttggt tcagagggct cactgtcgtg    2700
ccatgtgctt ccttctcaca ttaccaaatc ctataaataa caaattccaa taaatgctgg    2760
agtaatatgc ctaaatgaat tttttctctt tttgggaatt gtcactttc ttaacaaaaa    2820
tatttacaaa tcttggctgc ttttagttct tgatttgtta gattttggcg aaaaggtcat    2880
ttttctaaag tcttgaacac ctatctaacc taacatgctc ttctccctta cacaattgtc    2940
cacacgcttg aaagtgtttt acttgaaaat gatgtacaga ataatgactc atattttttca    3000
agtgtttctt ttattttttcc tacataattc agacttatgg cctattcctc tcttttacta    3060
tagtaaaggt atccattaac attatagatt tatttaatta ctatgacttg atgttgtgtg    3120
gtgactgagt tgagggaagc cctatgagtc actgaaacga tggcaggagt gcccttttttc    3180
tatcaataga gagagcaaaa aatgggcttt gctccccttt aagatatgaa gaaagaaata    3240
agggtcggaa tttagaccgc tcacagtaat tcgcccaacc tgtatataac agtcacgttt    3300
gttccaatat ttttttggtgc tatagtgaag tgttgttata gagaatatat attataacat    3360
aacataaaaa atcgatttcg agaaaaactt agctttttatt gtgaatgatt attatatatg    3420
gatggtgata tagagaggtt tggctgtatc taattttgat gatagttgct atggcaggtt    3480
cttgaatgct ggagttttttg gcaatggaac agagtcatgt cacacattac cacaatcagg    3540
gacaagggca gctatgttag ttaggatcaa cactctcctt caagggtact ctggcatcag    3600
atttgaaatc ttagaagcaa tcactaaatt gcttaaccac aatgttactc catgtttgcc    3660
ccttcgcggc accatcaccg cctctggtga tctcgtcccc ttgtcctaca ttgccggttt    3720
actcactggt cggcctaatt ctaaagcagt tggacctaat ggcgaaaccc tcaacgctga    3780
agaagcgttt cgtgttgctg gagttaacgg tggatttttttc gagttgcagc ctaaggaagg    3840
ccttgctctt gtgaatggta ctgcagttgg ttctggtttg gcctcaatgg ttctctttga    3900
tgctaatgtt ctcgcggtct tttctgaagt tctctcagct atttttgctg aggtaatgaa    3960
tggaaagccc gagttcactg accacttgac acacaagttg aagcatcacc ccggacaaat    4020
tgaggctgct gctattatgg aacacatttt ggatggtagc tcttatgtga aggcggctca    4080
gaagcttcac gaaacggatc ctctccaaaa accaaagcaa gatcgttatg ctcttagaac    4140
gtcgccccaa tggcttggcc ctcaaattga ggtcatccgt tctgcaacca agatgattga    4200
gagggagatt aattcagtga acgacaaccc tttgatcgat gtttcaagaa acaaggcatt    4260
acacggtggc aacttccagg gcactccaat tggtgtctct atggacaatg ctagattagc    4320
ccttgcatca atagggaaat tgatgtttgg ccaattctcc gagcttgtca acgattacta    4380
caacaacgga ttgccatcta atctgacagc aggaaggaat cctagcttgg actatggttt    4440
caagggatct gagattgcca tggcttcata ctgttcagaa cttcaattct tggcaaatcc    4500
agtgactaac cacgtacaaa gcgccgagca acacaaccaa gatgtgaact ccttggactt    4560
aatctcagct agaaaaacag ctgaagccgt ggacatctta aagctaatgt catccacata    4620
tctagttgca ctttgccaag caatagactt gaggcatttg gaagaaaatc tgaggaatgc    4680
agtcaagaac acggtgagcc aagtcgcaaa gagaacttta acaatgggta ccaatggaga    4740
acttcatcca tcaagattct gtgaaaagga cttgcttcga gtcgtggaca gggaatacgt    4800
cttcgcctat gctgacgacg cctgcagcgc taactaccca ctgatgcaga aactaaggca    4860
agtcctcgtc gaccacgcct tgcaaaatgc cgaaaatgag aagaacgcaa acagctcaat    4920
cttccaaaag atactagctt ttgaagacga gctaaaggcc gtgttgccaa aagaagtcga    4980
```

-continued

| | |
|---|---|
| gagtgcaaga gccgcgctgg aaagtgggaa ccctgcaatt gccaacagga taaaagaatg | 5040 |
| cagatcttat ccactttaca ggtttgttag aggagaactt ggagctgaat tattgacggg | 5100 |
| agaaaaagtc aggtcaccag gtgaagaatg tgacaaagtg ttcacagcaa tgtgcaatgg | 5160 |
| acaaattatt gattcattgt tagaatgtct caaggaatgg aatggtgcac ctcttccaat | 5220 |
| ctgttagaag ttggttctca acaacagga tctttgttaa tgtttgtcaa ttacctgtta | 5280 |
| tttttctatt tttactttt cttttgggg ttgattaaat gtaaactctc ttgaatatgt | 5340 |
| tggtttgtag ttgtattagt ctcttttccg tacaaataaa tgaaaagtga caatgtgctt | 5400 |
| atatgttctt gaaatttac tctctcatta tcattagtgt attatgcaga tattgccgtc | 5460 |
| tttaataagt tgacataaat atgcttatgt agtccaatac ttgcttcaaa tatgctttta | 5520 |
| atttaatgcc tcatatggaa ggcatatttg gtctcacaca catactttga gggcatattt | 5580 |
| aacccattaa tgttcttaag ctt | 5603 |

<210> SEQ ID NO 25
<211> LENGTH: 1870
<212> TYPE: DNA
<213> ORGANISM: Medicago truncatula

<400> SEQUENCE: 25

| | |
|---|---|
| acaaacccca cctaaccctc tacagtaaat ccacctaacc aaaacccat acacatcatc | 60 |
| atcatcatca tcatcatcaa aacctctcta taaaaaccca acaaccactc caaacatttt | 120 |
| cattacccaa aacacaaaaa cacactcaac aatggatctt ctcctccttg aaaagaccct | 180 |
| tttagccctc ttcattgccg ccacaatcgc catcacaatc tcaaaactcc gtggcaaacg | 240 |
| cttcaaactc ccaccaggtc caatcccagt ccctatcttc ggtaactggc ttcaagtcgg | 300 |
| agatgatctc aaccaccgta acctcaccga ttacgccaaa cgcttcggcg aaatgttcct | 360 |
| cctacgtatg ggccaacgta acctcgtggt agtttcttcc ccagaactcg ccaaagaagt | 420 |
| cctccacaca caaggtgttg aattcggatc acgtacacgt aacgtagttt tcgatatctt | 480 |
| cactggtaaa ggacaagaca tggtgttcac agtctacggc gaacattggc gtaaaatgcg | 540 |
| cagaatcatg acagttccgt ttttacaaa caaggttgtt caacagtatc gttacgggtg | 600 |
| ggagtctgaa gctgagagtg ttgttaacga tgttaagaac aacgccgaag caagtattgg | 660 |
| tgggattgtt ataaggaaga ggttgcagtt gatgatgtat aatattatgt ataggattat | 720 |
| gtttgataga agatttgaaa gtgaagagga tccttatttt gtcaagttga agctttgaa | 780 |
| tggtgaaagg agtcgtttgg ctcaaagttt tgagtataat tatggtgatt ttattcctat | 840 |
| tttgagacct ttttgaaag gctatttgaa ggttttgtaaa gaggttaaag atcgtaggtt | 900 |
| gcagcttttc aaagactatt tcgttgatga agaagaag cttgaaagca ccaagagcac | 960 |
| cacgagcaat gatggactaa aatgtgctat tgatcacatt tggatgcac aaaagaaggg | 1020 |
| tgaaatcaat gatgacaacg ttcttttacat tgttgagaac atcaatgttg ctgcaattga | 1080 |
| aacaacacta tggtcaattg aatggggaat tgctgagcta gtgaaccacc aaggcatcca | 1140 |
| aaacaaagta agggaagaaa tggacagagt tcttggacca ggacaccaag taactgagcc | 1200 |
| agatctccac aagctacctt acctacaagc tgtgatcaaa gagacacttc gtctacgaat | 1260 |
| ggcgatccca ctcctcgtac cacatatgaa ccttcatgat gcaaagctca atggtttcga | 1320 |
| tatcccagcc gagagcaaga tattggtcaa tgcatggtgg cttgcaaaca acccggctca | 1380 |
| ctggaaaaag ccggaggaat tcaggcccga acggttcttg gaggaagagt ctcatgtcga | 1440 |
| agctaatgga aatgatttta ggtaccttcc tttcggtgtt ggtagaagaa gttgccccgg | 1500 |

```
aattattctt gccttgccta tccttggtat cactattggg cgtctggttc agaatttcga    1560
gcttttgcct ccacctggac aatcaaagat tgacacttct gagaaaggag gacagtttag    1620
tctgcatata ctcaaacatt caaccattgt tgctaagcca agatcatttt aattagtctt    1680
cacactaata ccctttaat ttgttttact ttactttgtg taatgcattt taataattca     1740
aaatgtggga atgttattaa aatgtcttat tagcctgcaa ttgggtaggt gaataatgtt    1800
gttgttttgt gcttgtccca tgtataaagc tttgaacttt gaagtaatgg ttttgagatg    1860
attttttccc                                                           1870

<210> SEQ ID NO 26
<211> LENGTH: 1803
<212> TYPE: DNA
<213> ORGANISM: Arabidopsis thaliana

<400> SEQUENCE: 26
ctcagcagct tcttctgctt tcaattactc tcgccgacga ttttctcacc ggaaaaaaac      60
aatatcattg cggatacaca aactataatg gacctcctct tgctggagaa gtctttaatc     120
gccgtcttcg tggcggtgat tctcgccacg gtgatttcaa agctccgcgg caagaaattg     180
aagctacctc caggtcctat accaattccg atcttcggaa actggcttca agtcggagat     240
gatctcaacc accgtaatct cgtcgattac gctaagaaat tcggcgatct cttcctcctc     300
cgtatgggtc agcgaaacct agtcgtcgtc tcctcaccgg atctaacaaa ggaagtgctc     360
ctcactcaag gcgttgagtt tggatccaga acgagaaacg tcgtgttcga cattttcacc     420
gggaaaggtc aagatatggt gttcactgtt tacggcgagc attggaggaa gatgagaaga     480
atcatgacgg ttcctttctt caccaacaaa gttgttcaac agaatcgtga aggttgggag     540
tttgaagcag ctagtgttgt tgaagatgtt aagaagaatc cagattctgc tacgaaagga     600
atcgtgttga ggaaacgttt gcaattgatg atgtataaca atatgttccg tatcatgttc     660
gatagaagat ttgagagtga ggatgatcct cttttcctta ggcttaaggc tttgaatggt     720
gagagaagtc gattagctca gagctttgag tataactatg gagatttcat tcctatcctt     780
agaccattcc tcagaggcta tttgaagatt tgtcaagatg tgaaagatcg aagaatcgct     840
cttttcaaga agtactttgt tgatgagagg aagcaaattg cgagttctaa gcctacaggt     900
agtgaaggat tgaaatgtgc cattgatcac atccttgaag ctgagcagaa gggagaaatc     960
aacgaggaca atgttcttta catcgtcgag aacatcaatg tcgccgcgat tgagacaaca    1020
ttgtggtcta tcgagtgggg aattgcagag ctagtgaacc atcctgaaat ccagagtaag    1080
ctaaggaacg aactcgacac agttcttgga ccgggtgtgc aagtcaccga gcctgatctt    1140
cacaaacttc catacattca agctgtggtt aaggagactc ttcgtctgag aatggcgatt    1200
cctctcctcg tgcctcacat gaacctccat gatgcgaagc tcgctggcta cgatatccca    1260
gcagaaagca aaatccttgt taatgcttgg tggctagcaa acaaccccaa cagctggaag    1320
aagcctgaag agtttagacc agagaggttc tttgaagaag aatcgcacgt ggaagctaac    1380
ggtaatgact tcaggtatgt gccatttggt gttggacgtc gaagctgtcc cgggattata    1440
ttggcattgc ctattttggg gatcaccatt ggtaggatgg tccagaactt cgagcttctt    1500
cctcctccag gacagtctaa agtggatact agtgagaaag gtggacaatt cagcttgcac    1560
atccttaacc actccataat cgttatgaaa ccaaggaact gttaaactt ctgcacaaaa     1620 aaaaggatga agatgacttt ataaatgttt gtgaaatctg ttgaaatatt cccttgtttt    1680
```

```
gcttttgtga gatgttttg tgtaaaatgt ctttaaatgg ttcgttctac gattgcaata    1740
ataattagtg gtgctcattg ttttggatgg atcaatgtta tacttatatc atttgaaaat    1800
ctc                                                                  1803
```

<210> SEQ ID NO 27
<211> LENGTH: 1352
<212> TYPE: DNA
<213> ORGANISM: Camellia sinensis

<400> SEQUENCE: 27

```
atggtgttca ctgtatacgg tgagcactgg aggaagatga ggaggatcat gacggttcct     60 tttttttacca acaaggtggt gcagcagtac aggttcgggt gggaggacga ggcgggtcgg    120
gtcgtggagg atgtgaagaa gaacccggaa gcgaagacca tgggatcgt gctgaggagg     180 cggttgcagc tgatgatgta caataacatg tacaggatta tgtttgattc gaggttcgag    240
agcgaggagg acccgttgtt cgtgaaattg aaggcgttga atggagagag gagtaggttg    300
gctcagagct ttgagtataa ctacggcgat tttattccga ttttgaggcc gttcttgaga    360
gggtacttga gatctgcaa agaagttaaa gagaggaggt tgcagctttt caaggactat    420
tttgtcgatg aaaggaagaa gttagccaag ccacgaagag ccatggacac agttactcta    480
aaatgtgcga ttgatcatat tttggatgct caacaaaagg gagagatcaa cgaggacaac    540
gttctttaca tcgtggagaa cattaacgtc gctgcaattg agacaacatt atggtcgata    600
gaatggggca tagcagaact tgtaaaccac ccccaaatcc agaaaaagct tcggcacgaa    660
cttgacacca tgcttggcct tggagtccaa atcaccgagc cagacaccta caaactcccc    720
tacctccaag ctgtagtcaa agagaccctc cgcctccgga tggcaattcc cctcttagtc    780
ccccacatga acctccacga tgcaaagctc tctggctatg acatccctgc tgagagcaaa    840
atcttggtaa acgcgtggtg gcttgcaaac aaccccgaca actggaagaa cccagaagag    900
ttcaggcccg agaggttctt ggaagaggag gctaaggttg aggccaatgg caatgacttt    960
aggtaccttc cgtttggtgt cggaaggagg agttgccctg aattatcct tgctctgcca    1020 attctcggca tcactttggg aaggttggtt cagaatttcg agctcttgcc tcctccggga    1080
caggccaaga ttgatactgc tgagaagggg ggacagttca gcttgcatat tttgaagcac    1140
tcgaccattg ttctgaaacc aagatcgttc tgattttcat aaatttatgt ttttgtttta    1200
ttgtgttttg aagtgagtgg ggtgggggtt gagaaggaat tggggagatg ttgatctgtg    1260
tgtgattgta aatctctgtt gatgtgcaag gacaattcag aagtttgcaa ggagtatttt    1320
tctaaaaaaa aaaaaaaaaa aaaaaaaaaa aa                                  1352
```

<210> SEQ ID NO 28
<211> LENGTH: 1750
<212> TYPE: DNA
<213> ORGANISM: Mesembryanthemum crystallinum

<400> SEQUENCE: 28

```
cttattatat ctaccaaact tctcatagca agaatctccc atcctattaa tcaaatctag     60
gatggcaaaa atggaaactc attcaaaacc catgtccaaa aaacttgcta gaaacctcat    120
acttcttgcc atttccatca tagtgctaac aacttcatca tcaaatccaa acttttccta    180
ctatcttgcc atttcctac ccatcatagt ttacttggtc cattccattt gcttccaccg    240
tgcacaaaat tccggaacta ccctcccgg ccccctcgct ctcccatct tcgggaactg    300 gctgcaggtt gggaacgatc taaaccaccg ctgcctagcg gctctggcaa agacctatgg    360
```

```
gcccatgttt ctactcaagc tcggggtcag gaacctggtg gtggtgtcga accctgagct    420
ggcgtgcgag gttctccacg cacatggggt ggagtttggg tcgcgcccta ggaatgtcgt    480
ctttgacatc ttcaccgggg gcggccagga catggtgttc accgagtacg ggaccattg    540
gaggaagatg aggcggatca tgaccgtgcc tttcttcacc aacaaggtgg tgaacaacta    600
tagcccaatg tgggaggatg aaatggacaa agttgtgaat gacttgaacc acaatgaaaa    660
gattagcatc aaggcaaaac atgaagggtt tgtgataagg aagaggttgc aacttatgtt    720
gtataacatc atgtatagga tgatgtttga tgaggggttt gagtctatgg aagatcctat    780
gtttatcgat gcgacgaagt ttaactccga aaggagtagg ttggctcaaa gctttgagta    840
taactatgga gatttcatac cttttctcag acctttctta aggagttact tgagcaagtg    900
tagggacttg cagaagagcc gtcttgcatt tttcaacaac tactttgttg agaaaagaag    960
gaaaataatg gcagccaatg gagaacacca caagataagc tgtgcaattg accacataat   1020
tgaagctcaa atgaagggag aaatcaatgc agagaatgtc ctctacattg tagaaaacat   1080
caatgtagca gccatagaaa caaccctatg gtccatggaa tggcactag ctgagctagt   1140
aaaccaccct gaaatccaga aaaaaatccg acacgaaatc gccatgaaac ttgaggggaa   1200
acccgtcacg gaatcgaacc tcgagcaact tccctacttg caagctgtgg tgaaggaaac   1260
cctgaggcta cacaccccta tcctttgtt agtgccccat agtaaccttg aggaagctaa   1320
gctaggtggt tacacaatcc ctaagaactc aaaggttgtg gtcaacgcgt ggtggcttgc   1380
caacaaccct gagtggtggc gggacgcgga ggagttccgg cccgagcggt tcctcgagga   1440
ggaggccggg gcggatgcag ccgtgggggg tggaaaggtc gattttcggt ttgtgccatt   1500
tggggttggg aggaggagtt gccctgggat tatattggca ttgccaatat tagggcttgt   1560
tattgctaag ttggtgagta attttgagat gaagcctcca ccaggggaag aaaagattga   1620
tgtgagtgag aaaggaggac agtttagcct ccacattgct aagcattcaa cagtagtttt   1680
tcacccaatt catgcagctt gatttggtga taataatgaa gttttttatg tataactttc   1740
acttatgacc                                                           1750

<210> SEQ ID NO 29
<211> LENGTH: 1801
<212> TYPE: DNA
<213> ORGANISM: Petroselinum crispum

<400> SEQUENCE: 29
gaattcggca cgagcgtgtt ccctaagtct ttcatttcca caatctatct aaactacaca    60
taaacaaaac acacacagac ataaaacaca tcaccattta tatataatct acaacaccct   120
ttgtttctcc tattctctca tccaataaaa catgatggac tttgttttgt tggagaaggc   180
cctgttgggc ttgttcattg caacaattgt agccatcact atttccaagt tacgtggcaa   240
gaaactcaaa ctcccaccag ggcctattcc tgttcctgtg tttggtaact ggttacaagt   300
tggtgatgat cttaaccaga ggaacctggt ggactatgcc aagaagtttg gagacttgtt   360
tatgttacgt atgggacaga ggaacttggt tgttgtgtcc tcacctgaat ggctaaaga   420
tgttttgcat acacagggtg ttgagtttgg atcacgcact cgtaacgttg ttttcgatat   480
cttcacaggc aagggacagg acatggtgtt cacagtctat agtgagcatt ggagaaagat   540
gaggagaatc atgacagtac ctttctttac gaacaaagtt gtccagcagt atcgattcgg   600
gtgggaggat gaggctgccc gtgttgttga ggatgttaag gccaatcctg aggctgctac   660
```

```
caatgggatc gtgttgagga accgattgca gttgctcatg tataataata tgtacagaat    720
catgtttgat agaaggtttg agagcgtaga tgatcctttg tttttgaagc ttaaggcatt    780
gaatggggag cgcagtaggc ttgctcagag cttcgaatac catttcggag attttatccc    840
tattcttcgc cctttcttga gaggttatct taaactttgc caggaaatca aggacaaaag    900
gttgaagctc tttaaggatt attttgtgga cgagaggaag aagcttgaaa gcataaagag    960
tgtagataac aacagcttga agtgcgccat agatcacatt atagaagctc agcaaaaggg   1020
agagatcaac gaggacaacg ttctttacat tgttgaaaac attaatgttg ctgcaattga   1080
aacaacacta tggtcaattg aatggggcat tgcggaacta gttaataacc ctgaaatcca   1140
gaagaagctg aggcatgagt tggacactgt gcttggggcc ggagttcaga tctgtgagcc   1200
agacgtccag aagctcccct accttcaagc tgtgatcaaa gagactcttc gatacagaat   1260
ggccattcct cttttagtcc ctcatatgaa ccttcatgat gcgaagcttg cgggttatga   1320
catcccggca gagagcaaaa tcttggtcaa tgcatggtgg cttgccaaca atcccgctca   1380
ctggaataaa ccagatgagt ttaggcctga gaggttcttg gaagaagaat ctaaagttga   1440
ggctaatgga aatgatttca gtacatacc attcggagta gggaggagaa gctgccctgg   1500
aattattctt gcattgccta tcctcggtat cgtaatcgga cgtttggtgc agaattttga   1560
gctcttgcct cctcctggac agtccaagat tgatacagca gagaaggag gacagttcag   1620 tcttcaaatt ttgaagcact ccactatcgt ctgcaagcca agatcacttt aaaataaaat   1680
ttgtctcttc tacgtttaca tttgactgta aaattgggtg gactggatac cattttgcta   1740
caatatttta ataatttgtg taaatctatg aatttctgaa aaaaaaaaaa aaaaactcga   1800
g                                                                  1801

<210> SEQ ID NO 30
<211> LENGTH: 1803
<212> TYPE: DNA
<213> ORGANISM: Populus tremuloides

<400> SEQUENCE: 30
gtcgacccac gcgtccgctc ttcttaccta aaaaatcccc acctcttttt gacaaagaaa     60
ccagttccaa gatcatggat ctcctactcc tggagaagac cctcttgggt tctttcgttg    120
ccattctcgt tgccattctc gtttctaaac tacgtggcaa acgttttaaa ctccctccag    180
gtcctttacc tgtccccgtg tttggaaact ggcttcaagt tggtgatgat ttgaaccacc    240
gtaacctcac cgacttagcc aagaaaattcg gtgacatcct cctccttcgc atgggccaac    300
gcaatcttgt agtcgtctcc tcacctgagc tatccaaaga ggttctgcac acacaaggtg    360
ttgagttcgg gtcgagaaca agaaatgttg tttttgatat ctttactgga aagggacaag    420
acatggtgtt cactgtctat ggtgagcatt ggaggaagat gaggagaatc atgacagtcc    480 cttttctttac aaacaaggtt gtccaacaat ataggtatgg atgggaagag gaagcggctc    540
aagttgtcga ggatgttaag aaaaaccccg gggctgcaac tcatgggatt gttttgagga    600
ggagactgca actgatgatg tataacaaca tgtataggat tatgtttgat aggagatttg    660
agagcgaaga agatcctttg tttaataaac ttaaggcttt gaatggtgag aggagcagat    720
tggctcagag ttttgattat aattatggtg atttcatccc catttgaga cctttcttga    780 gaggttactt gaagatctgc caggaggtta aggagagaag gttgcaactc ttcaaggact    840
actttgtcga tgagaggaag aaacttgcaa gcacaaagaa catgtgcaat gaagggttga    900
agtgcgcaat agaccatatc ctggatgctc aaaagaaggg agagatcaac gaggacaacg    960
```

-continued

```
tcctttacat tgttgagaac atcaacgtcg ctgcaattga acaacacta tggtcgatcg     1020
agtggggaat tgctgagctt gtgaaccatc ctgaaatcca aagaagttg cgccatgagc     1080
tcgatacctt gcttggacct ggtcaccaaa tcaccgagcc tgacacctac aagctccctt    1140
accttaacgc tgttgtcaaa gagaccctcc gactcaggat ggcaattcct ctactcgtcc    1200
cacacatgaa ccttcatgat gccaagcttg gaggctttga cattccagct gagagcaaga    1260
tcttggtcaa cgcctggtgg ctcgccaaca accctgccca ctggaaaaac cctgaagaat    1320
tcaggccaga gaggttcttg gaagaggagg ccaaggtcga ggccaatggc aatgatttca    1380
ggtaccttcc atttggagtt gggagaagga gctgccctgg gattattctt gcattgccaa    1440
ttcttggcat tactctggga cgtctggtac agaatttcga gctcttgcct cctcctggac    1500
agtcaaagat cgacacctca gagaaaggtg gacagttcag tttgcacata ttgaagcact    1560
ccactattgt tgcaaagcca aggtcctttt aatttcattt cacacttctt ttttttttgt    1620
cttttttttt ttcctgggtg tgctgttact gtaagactgt tgaagaagaa aagcgggatg    1680
gttttggatg cgggatccag atggaattgt ctaattatga tgatataatg ggggtgtctc    1740
tgtaaatcat gaagttatga actcaaaagg gatcttttt aagactttgc aataatttca     1800
cta                                                                  1803
```

<210> SEQ ID NO 31
<211> LENGTH: 1713
<212> TYPE: DNA
<213> ORGANISM: Catharanthus roseus

<400> SEQUENCE: 31

```
gccaccgcca ccacaatcac agccatttcc cgttgatttc ccaccaccga ttatggatct      60
tctcctctta gagaagaccc ttttgggctt atttgccgcc atcattgtgg cctctatagt     120
ttcaaagcta cgaggaaaga aatttaagct tcctccaggt cctatcccgg taccggtttt    180
tggaaactgg cttcaagttg gggatgactt gaatcacaga atctatcgg attacgctaa     240
gaaatttggc gaaattttct tacttagaat gggccaacgt aatctggttg tggtttcatc    300
tcctgaactg gctaaagaag tttgcacac tcaggggggtt gaatttggct cccgtactag    360
aaatgttgtg tttgatatct tcacaggaaa aggacaggac atggtttta ccgtttatgg     420
tgaacattgg aggaaaatga aagaatcat gactgtcccg ttttttacta ataaagtagt     480
tcaacagtat agatatggat gggaagaaga ggcagcccgt gttgttgagg atgtgaagaa    540
aaatcctgaa tctgcaacta tgggattgt attgaggaga aggttacaac ttatgatgta    600
caataacatg tacaggatta tgtttgatag aaggtttgag agtgaggatg atcctctttt    660
tgttaaactt aaggccttga atggtgaaag gagtagattg gcccagggct tgagtacaa     720
ttatggcgat tcattccaa ttttgaggcc tttcttgaga ggttatttga ggatctgtaa      780
ggaggttaag gagagacgat tgcagctttt caaggattac ttcgtcgacg aaaggaagaa    840
gtttgggagt acaaaaagca tggataacaa cagcttgaaa tgtgccattg atcatatcct    900
agaagctcag caaaagggag agatcaacga ggataatgtc ctttacattg ttgaaaacat    960
caatgttgct gccatcgaga caacactatg gtccattgag tggggaattg cagaattggt    1020
gaaccaccct gaaatccaga agaagctacg agacgagctt gagactgtgc taggacccgg    1080
cgtgcagatc actgaaccgg atacttacaa gttaccatac cttcaggcag tgatcaagga    1140
gacacttcgt ctcagaatgg cgattcccct tttcctgcct cacatgaacc tacacgatgc    1200
```

-continued

```
caagcttggt ggctatgaca ttccagcgga gagcaaaata ctggtgaatg cctggttttt      1260
agccaacaat ccggagcatt ggaagaagcc tgaagagttc agaccggaaa ggttcttgga      1320
agaggaatcg aaagttgagg ctaatggcaa tgacttcaga tatctaccat ttggtgttgg      1380
taggagaagt tgccctggta ttattctagc attgccaatt cttggcatta ccataggacg      1440
attggttcag aactttgagc ttttgcctcc accaggaaaa tctaagattg atactagtga      1500
gaaaggtgga caattcagtt tgcacatttt gaagcactct actattgtac tcaagcctag      1560 gacttttttag attcattttta tcatcatttc ttgaaaaact gttgtaaaaa ttgaatctcc      1620
gctgcagatt tgagtcggaa cgggtgtgct tgtcaatctt tctttaatca tcatgtaacc      1680
gattattatt attaaaaaaa aaaaaaaaaa aaa                                    1713
```

<210> SEQ ID NO 32
<211> LENGTH: 1620
<212> TYPE: DNA
<213> ORGANISM: Helianthus tuberosus
<220> FEATURE:
<221> NAME/KEY: modified_base
<222> LOCATION: (1588)..(1608)
<223> OTHER INFORMATION: N = A, C, G and/or T/U

<400> SEQUENCE: 32

```
aaatcacaca acaccaccac caccgtaacc atggacctcc tcctcataga aaaaccctc       60 gtcgccttat tcgccgccat tatcggcgca atactaatct ccaaactccg cggtaaaaaa     120
ttcaagctcc cacctggccc aatcccggtt ccaattttcg gcaactggct acaagttggc     180
gatgatttga accaccggaa cttaaccgat ctggctaaga ggtttggtga gatcttgctg     240
ctacgcatgg ggcagaggaa tctggtagtt gtgtcttcgc ctgagcttgc taaagaggtg     300
ttgcatacac aaggagtgga gtttggttcg agaacaagga atgttgtgtt cgatattttt     360
actgggaagg gtcaggatat ggtgtttacg gtttatggtg agcattggag gaagatgagg     420
aggatcatga ccgtaccctt tttcaccaac aaagttgttc agcaatacag gtatgggtgg     480
gaggctgagg ccgcggcggt tgtggacgat gtgaagaaga atccggctgc agcaactgaa     540
ggaatcgtga tccgaagacg gttacaactc atgatgtata acaacatgtt cagaatcatg     600
ttcgacagac gattcgaaag tgaagatgat cccttgtttt tgaaactcaa ggcgttgaac     660
ggtgagagga gtcgattggc gcagagcttt gagtacaact atggcgattt catccctatt     720
ttgcggccgt ttttgagaaa ttatttgaag ttgtgcaagg aagttaaaga taaaaggatt     780
cagctcttca aggattactt cgttgacgaa aggaagaaga ttggaagcac taagaaaatg     840
gacaacaatc agttgaaatg tgccattgat cacattcttg aagctaaaga gaagggtgag     900
atcaatgaag acaatgttct ttacattgtt gaaaacatca atgttgcagc aatcgagaca     960
actctatggt cgatcgaatg gggaattgcg gagctagtta accatcccga gatccaagcc    1020
aaactcaggc acgagctcga caccaagctc gggcccggtg tccagatcac cgagcccgac    1080
gtccaaaacc tcccttacct ccaagccgtg gtcaaggaaa ccctccgtct ccgtatggcg    1140
atcccgcttc tagtcccaca catgaacctc atgacgcta agctcggcgg gtttgacatc    1200
ccggccgaaa gcaagatctt ggtcaacgcg tggtggttag caaacaaccc cgaccaatgg    1260
aagaaacccg aggagtttag gccagagagg tttttggaag aggaagcgaa ggttgaggct    1320
aacgggaatg attttaggta cttgccgttt ggagtcggga aaggagttg ccccgggatt    1380 attcttgcat tgccgatact tggtattaca atcgggcgtt tggtgcagaa tttcgagctg    1440
ttgcctccac cgggacagtc taagatcgat accgatgaga agggtgggca gtttagtttg    1500
```

```
catatcttga agcactctac tatcgtagct aaacctaggt cattttaagg attcttgttt    1560
atgttcttta ttgtatgata aaccaagngg ngnnggngnn gngngannaa aaaaaaaaaa    1620

<210> SEQ ID NO 33
<211> LENGTH: 1996
<212> TYPE: DNA
<213> ORGANISM: Pinus taeda

<400> SEQUENCE: 33
gagcagctcg gggctgtgaa tgtttcttca atttcaattg cagaggcatt gaattctccg      60
agtacacaat aatggagatc atgactgtgg caagtctaga aaaggggctt ctggccattt     120
tcgctgtaat tgtcggtgcc atttcatat cgaagctcaa atccaagaag ctcaagctgc      180
cccccggccc gctggcggtg cccatcttcg ggaactggct gcaggtgggg gacgatctca     240
atcacaggaa cctgggggac ttggcgaaga agtatggcga gatctttctg ctgaagatgg     300
ggcagaggaa tctggttgtg gtgtcatcgc cggatctcgc caaggaggtt ctgcacacgc     360 aggggggtgga gttcggctcg cggactcgga acgtggtgtt cgatatattc acggggaagg     420
ggcaggacat ggtgttcacg gtgtacggcg agcattggcg gaagatgcgg cggatcatga     480
cggtgccctt ctttaccaac aaggtcgtcc agcagtacag attcgcgtgg aagacgagc      540 tcggccgcgc ggtggatgat atcaagaaac gacccgaggc gtctaccacg gggattgtga     600
tcaggaggcg cctgcagctg gtgatgtata acatcatgta caggatgatg tttgacaggc     660
gcttcgagag cgaggacgac ccgctcttcc tccgcctcaa ggctctcaat ggcgagagga     720
gccgcctggc ccagagcttc gagtataact atggtgactt cattcctgtt ctcaggccgt     780
tcctcagagg gtacctgaag atctgcaagg aggtgaaaga aagcaggctg ttgcttttca     840
aggattattt cattgatgag aggaagaaat tggccagtac cacaggctcc aaggtcaccg     900
gcgataagtg cgctattgat cacatcttcg aagctgagga aagggcgaa atcaacgaag      960 acaatgtcct ctacatcgtg gagaacatta atgttgcagc aatcgagaca actttatggt    1020
ccatggaatg gggactcgcc gaaatcgtga accaccccga gattcagcag aagatccgcg    1080
ccgagctgga cgctgtaatc gggcggggcg tccccttgac ggagccggac actaccaaat    1140
tgccctacct ccaagccgtg gtcaaagaaa ccctgcgtct ccacatggcg attcccctgc    1200
ttgtgcctca catgaacctt caccaggcca agctcggcgg ctacgacatt ccggccgaaa    1260
gcaaaatact ggtgaatgcc tggtttctgg ccaacaatcc cgagtggtgg agaaaacccg    1320
aggaatttat tcccgagagg tttctgggag aagagaagat tgaagccagc gggaacgatt    1380
tcagattcct accattcggc gttggaagga ggagctgccc tggaattatc ttggctctgc    1440
caatcctggc tctggcgctt ggaaggctgg ttcagaactt tgagctgctg cctccgcctg    1500
ggcaatccaa ggtggatgtg acagagaaag gagggcaatt cagcctgcac attctcaacc    1560
actccgttgt tgtggccaaa ccaatagcct gaagctcaga tcctgaaaaa aaatatagaa    1620
tttcttccaa gtctggagga gctggaagca ataaacactt tatatataca gttgcagcca    1680
aatgaagtgt ggatttccat tgtaattcat ccccagatgg tttgttttgt tgtcagtagt    1740
tttgaagtcc gtcagattgc ttgcccgaat atgcactgta tccaaaaatt tgttatgcat    1800
tttggaaaaa attgtttgtg atcactcatt gtaaaagtac accaattggg cttttaatat    1860
tatggttttt cagtgaattc tgtccttctg atcaggattc agaagcatgt ggacaggggg    1920
tttttggaaa aaattgtttg tgatcactca ttgtaaaagt acaccaattg ggcttttaat    1980
```
attatggttt ttcagt 1996

<210> SEQ ID NO 34
<211> LENGTH: 1750
<212> TYPE: DNA
<213> ORGANISM: Populus trichocarpa x populus deltoides

<400> SEQUENCE: 34

| | | |
|---|---|---|
| cccctctttt tgacaaagaa accagttcca atatcatgga tctccttctc ctggagaaga | 60 |
| ccctcttggg ttctttcgtt gccattctcg ttgccattct cgtttctaaa ctacgtggca | 120 |
| aacgttttaa actccctcca ggtcctatac ctgtccccgt gtttggaaac tggcttcaag | 180 |
| ttggtgatga tttgaaccac cgtaacctca ccgacttagc caagaaattc ggtgacatct | 240 |
| tcctccttcg tatgggccaa cgtaaccttg ttgtcgtctc ttctcctgac ctatccaaag | 300 |
| aggttctgca cacacaaggt gttgagttcg ggtcgagaac aagaaatgtt gtttttgata | 360 |
| tctttactgg aaagggacaa gacatggtgt tcactgtcta cggtgaacat tggaggaaga | 420 |
| tgaggagaat catgactgtc cctttcttta caaacaaggt tgtccaacaa tataggtatg | 480 |
| gctggggagga ggaagccgct caagttgtcg aggatgttaa gaaaaaccct gaggctgcaa | 540 |
| ccaatgggat tgttttgagg aggcgattgc aactcatgat gtataataat atgtacagga | 600 |
| ttatgtttga taggagattt gagagcgaag acgatccttt gtttaacaag ctcaaggctt | 660 |
| tgaatggtga gaggagcaga ttggctcaga gttttgatta taattatggt gatttcatcc | 720 |
| ccattttgag acctttcttg agaggttact gaagatctg ccaggaggtt aaggagagaa | 780 |
| ggttgcaact cttcaaggac tactttgtcg atgagaggaa gaaacttgcc agcacaaaga | 840 |
| acatgagcaa tgaagggttg aagtgcgcaa tagaccacat cctcgatgct caaaagaaag | 900 |
| gagagatcaa cgaggacaac gttctttaca ttgttgagaa catcaacgtc gctgcaattg | 960 |
| agacaacact atggtcgatc gagtggggaa ttgctgagct tgtgaaccat cctgaaatcc | 1020 |
| agaagaagtt gcgccatgag ctcgatacct tgcttggacc tggtcaccaa atcaccgagc | 1080 |
| ctgacaccta caagctccct taccttaatg ctgttatcaa agagaccctc cgactcagga | 1140 |
| tggcaattcc tctacttgtc ccacacatga accttcatga tgccaagctt ggaggcttcg | 1200 |
| acattccagc tgagagcaag atcttggtca atgcctggtg gctcgccaac aaccctgccc | 1260 |
| actggaaaaa ccctgaagaa ttcaggccag agaggttctt ggaagaggag gccaaggttg | 1320 |
| aggccaatgg caatgatttc aggtaccttc catttggagt tgggagaagg agctgtcctg | 1380 |
| gaattattct tgcattgcca attcttggca ttactctggg acgtctggta cagaatttcg | 1440 |
| agctcttgcc tcctcccgga cagtcaaaga tcgacaccgc agagaaaggt ggacagttca | 1500 |
| gtttgcacat attgaagcac tccactattg ttgcaaagcc aagtcctttt aatttcatt | 1560 |
| tcacactttt tgttttctgg gtgttttgtt actgtaagac tgttgaagaa gaaaagcggg | 1620 |
| atggttttgg atgcgggatc cagatggaat tgtctaatta tgatataatg ggggtgtcac | 1680 |
| tgtaaatcta tgaagctatg aactcaaaag ggatcttttt tttaagactt tgcaataagt | 1740 |
| ttctcgtgcc | 1750 |

<210> SEQ ID NO 35
<211> LENGTH: 1065
<212> TYPE: DNA
<213> ORGANISM: Phaseolus vulgaris

<400> SEQUENCE: 35
tttactgttt atggtgaaca ctggcgcaca atgcgcacaa tcatgaacct gccattcttc     60

| accaagaaag gtgttcacaa ctacagcacc atgtgggagg aagaaatgga attggtggtg | 120 |
| cgtgacctca aggtgaatga gcatgtgagg agcgaaggaa ttgttatcag aaagcggctt | 180 |
| cagttgatgc tatacaatat catgtatagg atgatgtttg acgccaagtt tgagtcacaa | 240 |
| gaggacccct tgttcattca ggccacgagg tttaactctg agcgaagccg tttggcacag | 300 |
| agttttgaat acaattatgg agattttata ccattgctca ggccattctt gaggggatac | 360 |
| ctgaacaaat gcaaggactt gcaatctagg aggcttgcat ttttcaacac ccactatgtt | 420 |
| cagaaaagaa gacaaataat ggctgccaat ggggagaagc acaagatcag ctgtgcaatt | 480 |
| gatcacatca tagacgctca gatgaaggga gaaatcagtg aagagaatgt gatatatata | 540 |
| gtagaaaaca tcaatgttgc agcaattgag acaacattat ggtccatgga atggcaata | 600 |
| gctgagttgg tgaatcatcc aagcgttcaa agcaagatac gtgatgagat atcagaagtg | 660 |
| cttaaagggg agccagtgac ggaatcaaac ctacacgagc taccatactt acaagcaact | 720 |
| gtgaaagaaa cactgagact tcacacccca attcttcttt tggtgcctca catgaacctg | 780 |
| gaagaagcaa agctaggagg atacacagta ccaaaagagt ccaaggtggt ggtaaatgct | 840 |
| tggtggcttg ccaataaccc atcatggtgg aagaatccag aggagtttag gccagaaagg | 900 |
| tttttggaag aggagtgtgc aacagatgct gttgcaggag gaaaggttga tttaggttc | 960 |
| gtgccatttg gtgtgggaag gaggagttgc cctggaatca tacttgcatt accaatactt | 1020 |
| ggacttgtga ttgcaaagat ggtgtcaaat tttgagctca gtgct | 1065 |

<210> SEQ ID NO 36
<211> LENGTH: 1623
<212> TYPE: DNA
<213> ORGANISM: Ammi majus

<400> SEQUENCE: 36

| ccttcattct cctattctca tcctcaacca acaaaacatg atggactttg ttctgttaga | 60 |
| gaaggccctg ttgggcttgt tcattgcaac cattgtagcc atcactattt ccaagttacg | 120 |
| tggcaagaaa ctcaagctcc caccagggcc tatccctgtt cctgtgtttg gtaactggtt | 180 |
| gcaagttggt gatgatctta accagaggaa cctggtggag tatgccaaga gtttggtga | 240 |
| cttgtttctt ttgcgtatgg gacagaggaa cttggtcgtt gtgtcttctc ctgatttggc | 300 |
| taaagatgtt ttgcatacac agggtgttga gtttggttca cgcactcgta acgttgtttt | 360 |
| cgatatcttc actggcaagg gacaggacat ggttttcacg gtctacagtg agcattggag | 420 |
| gaagatgagg agaatcatga cagtacccttt ctttaccaac aaagttgtgc agcagtatcg | 480 |
| atttgggtgg gaggatgagg ctgcccgtgt tgttgaggat gttaaggcca atcctgaggc | 540 |
| tgctaccaat gggatcgtgt tgaggaaccg actgcagttg ctcatgtaca ataatatgta | 600 |
| cagaattatg tttgatagaa ggtttgagag tgtagatgat cctttattct tgaagcttaa | 660 |
| ggcattgaat ggggagcgta gtagacttgc tcagagcttt gagtacaatt tcggagattt | 720 |
| tatccctatt cttcgccctt tcttgagagg ttatcttaaa cttttgccagg aaatcaagga | 780 |
| caaaagattg aagctctttta aggattattt cgtggacgag aggaagaagc ttgaaagcat | 840 |
| aaagagcgta ggtaacaaca gcttgaagtg cgccattgat cacatcatag aagctcagga | 900 |
| aaaggagag atcaatgagg acaacgttct ttacattgtt gaaaacatta atgttgctgc | 960 |
| aattgaaaca acactatggt caattgaatg gggcattgcg gaattagtta ataaccctga | 1020 |
| aatccagaag aagctgaggc atgagttaga cactgtgctt ggggctggag ttcagatctg | 1080 |

```
tgagccagac gtccagaagc tcccttacct tcaagctgtg atcaaagaga ctcttcgata      1140
cagaatggcc attcctcttt tagtccctca catgaacctt catgaagcaa agcttgcggg      1200
ttatgacatc ccggcagaga gcaaaatctt ggtcaatgca tggtggcttg ccaacaatcc      1260
cgctcactgg aataaaccag atgagtttag gcctgagagg ttcttggaag aagaatcaaa      1320
agttgaggct aatggaaatg atttcaagta cataccattc ggagtcggga ggagaagctg      1380
ccctggaatt atccttgcat tgcctatcct gggtatcgta atcggacgtt tggtgcagaa      1440
ctttgagctc ttgcctcctc ctggacagtc taagattgat acagcagaga aaggaggaca      1500
gttcagtctt caaattttga agcactccac tatcgtttgc aagccaagat catcttaata      1560
atattcgtct cctctacgtt tacatttgat tgtaaaattg ggtggacttg ataccattat      1620
acc                                                                    1623

<210> SEQ ID NO 37
<211> LENGTH: 1661
<212> TYPE: DNA
<213> ORGANISM: Medicago truncatula

<400> SEQUENCE: 37
gcaccagctc tcttgcagtt cacacatacc aaatctcaaa ccacttcaac acaactcaat        60
acgacacttc tcttcatcaa ggaccaaacc actccaagaa aaacaaagat gatcataaa        120 cgttagagat tcgacaatgg tgcggccgtc agaggaggtt acacagcgga cggtgtggaa       180
ttccaacgtt gatttggtgg taccgaattt ccatacacca agtgtttact tttatagacc       240
taatggtgct tccaatttct ttgatgccaa ggttcttaaa gaagctctta gcaaggtgct       300
tgtcccgttt tatccaatgg ctggtcgtct tcgtcgtgat gaagatggtc gtgttgagat       360
tgattgtgat ggtcaagggg tgctctttgt cgaggctgac accggtggag tcgttgatga       420
ttttggagac tttgctccca cgcttgagct ccgccagctt atcccagccg ttgattattc       480
gcgcggaatc gaaacatatc cccttcttgt attgcaggta acatatttca aatgtggagg       540
agtctcactt ggtgttggta tgcaacatca tgtagcagat ggagcttctg gtcttcattt       600
catcaataca tggtcagatg tagctcgtgg cctagacgtt tccatgccac cattcattga       660
ccggacacta ctccgtgccc gcgatcctcc ccgacctgtt ttcgatcaca tcgaatacaa       720
gcctccacca tcaatgaaga ctcatcaaca accaacaaaa ccaggctcag atggtgcagc       780
agtttcgatt tcaaattga ctcgcgaaca actcaacaca ttgaaagcta agtccaaaga       840
agccggcaac acaatccact acagttctta tgagatgtta gccggacatg tttggagaag       900
tgtctgcaaa gcaagatcat tacctgatga tcaagaaacc aaattgtata ttgcaaccga       960
tggacgggca aggttgcaac ctcctcctcc accaggttac ttcggcaatg tgatattcac      1020
aacaacacct atagctatag caggtgatct catgacgaaa ccaacatggt atgctgcaag      1080
tagaattcac aacgcgttgt cgcgaatgga caacgagtat ttgagatcag ctcttgattt      1140
tcttgagcta caacctgatc ttaaggctct tgttcgcggt gcacatactt tcaagtgtcc      1200
gaatcttggt attactagtt gggctaggct tccgatacat gatgctgatt ttggttgggg      1260
aaggcctatt ttcatgggac ctggtgggat tgcttatgaa gggctttctt tcataattcc      1320
aagctcagca aatgatggaa gtttatctgt ggcaattgct cttcagcatg aacatatgaa      1380
agtgttcaag gacttcttgt atgatatttg aagatacaaa atgtcacttg gaataccact      1440
aagtttctaa ggtggcattt tgtttcctag ttttttgttt tcttttaggt acttttggtg      1500
aactatatgc aaatgttaat gttaatggga cttgtttcag cttctataat ctgtaaacaa      1560
```

```
tttaatttga tatgttgcag ttagcacaag acttcaaaca tttggatacc tgttactggg    1620
tattgtagtt atttatcgat gatttcactc tcccctcgtg c                       1661

<210> SEQ ID NO 38
<211> LENGTH: 1507
<212> TYPE: DNA
<213> ORGANISM: Nicotiana tabacum

<400> SEQUENCE: 38
tttggaattc atttcaggga attgaaccgg ttgatcaacg atgaagatcg aggtgaaaga      60
atcgacgatg gtaaagccgg cggcggagac gccacaacag aggctgtgga actctaatgt    120
ggatttggtg gtgccgaatt ccacacgcc aagtgtttat ttttacaggc cgacgggatc     180
cccaaatttc ttcgacggaa aagtgctgaa ggaagctcta agcaaagcac ttgtgccgtt    240
ttatcctatg gcggggaggc tgtgtaggga cgaagatggt cgtattgaga ttgactgtaa    300
aggtcagggg gtgcttttg tggaagctga gtcggatggt gtggtggatg attttggtga     360
ttttgccccg acgttagaac tccgtcaact catccccgcc gttgattact cacaaggaat    420
tcaatcgtat gctctcttag tgttgcagat aacacatttt aaatgtgggg gagtttccct    480
tggtgtgggc atgcaacatc atgcagcaga tggagcttct ggtcttcact tcatcaacac    540
atggtctgat atggctcgtg gtctggacct caccatccca cctttcattg accggaccct    600
cctccgtgct cgtgatccac ctcagcctca gtttccccat gtcgagtacc agccacctcc    660
cactctcaag gtaactccag aaaacacccc tatatctgaa gctgttcctg aaaccagcgt    720
gtccatcttc aaattaaccc gtgatcaaat caataccctc aaagcgaagt ccaaggaaga    780
tggaaatacc gttaactaca gctcctacga gatgttggca ggacatgtgt ggcgctccac    840
gtgcatggca cgaggactcg ctcatgatca agaaaccaaa ttgtacatag caacagatgg    900
acgttccagg cttcggccct ctctcccacc aggctatttc ggtaatgtga tatttactac    960
cactcctatt gcagtcgcag gtgatatcca atcgaagcct atttggtatg ctgccagtaa   1020
attacatgat gcattggcta gaatggacaa cgattactta agatcagctc ttgattattt   1080
ggagttgcag cctgacttaa aggctcttgt tcgtggtgca catacgttta agtgcccgaa   1140
tttaggaata actagttggt ctaggctgcc aatccatgat gctgattttg ctgggtag     1200 gcctatattt atgggacctg gtggtattgc ttatgaaggt ttaagcttta tattgccaag   1260
tcctacaaat gatggcagtc aatctgttgc aatctctcta caagcagaac acatgaaact   1320
tttcgagaag ttcttgtatg acttttgaaa gaaaccaaat cttttgtgctg cttctttttgg  1380 ggtttatatt gatggatatg taaaagactc ctttttatttt ttcattggag ctgttcttt   1440 cttcttcttt ttttcctcag tggaacttcg gtcatattca taatagacat cagttctatt   1500
tctgctt                                                              1507

<210> SEQ ID NO 39
<211> LENGTH: 1560
<212> TYPE: DNA
<213> ORGANISM: Medicago sativa

<400> SEQUENCE: 39
atggattcgc ttctaaaatt tccaatcatg gtgaacttga aggaagaacc atttcttatg      60
gcaatcatgg tcatcgtacc actaacactc ttgttgggtt taatgtcacg aatcctcaaa    120
agaccaagat atccaccagg accaaaaggg ttacctatta taggtaacat gctaatgatg    180
```

```
gaccaattaa cccaccgtgg tctagccaac ttagccaaaa aatatggagg catctttcac    240
ctacgcatgg gattcctcca catggtagct atttccgacg cggacgccgc acgacaagtt    300
ctccaagttc aagacaacat cttttccaac cggccagcaa ctgtggctat taaataccta    360
acttacgacc gtgctgacat ggcgttcgct cactacggtc ccttttggcg ccagatgcga    420
aaactctgcg tgatgaagct tttcagccgc aagcacgcag agtcttggca atctgttaga    480
gacgaggttg actatgctgt ccgaactgtt tcggacaaca taggcaaccc tgtgaatatc    540
ggagaactgg tgttcaattt aactaaaaac attatatatc gagcggcttt cgggtcgagc    600
tcaagagaag gacaagatga gttattgga atattgcaag agttttccaa attgtttgga    660
gcttttaata tttccgactt tgtaccttgt tttggagcta ttgaccctca agggcttaat    720
gctaggcttg tgaaggctcg taaagatttg gatagtttca tagacaaaat catagatgaa    780
catgtggaga agaagaagag tgttgttgat gaagaaacgg atatggtgga tgagttgctt    840
gctttctata gtgaggaggc taaattgaat aatgaatcag atgatttgca taattccatc    900
aaacttacca aggataacat caaagccatc ataatggacg tgatgtttgg aggaacggaa    960
acggtagcat cagcaatcga atgggttatg gcagagttaa tgaaaagccc agaagaccta   1020
aaaaagttc aacaagaact agcagaagtt gtgggtctga gccgacaggt tgaagaaccc   1080
gatttcgaga aactaaccta tctaaaatgc gctcttaagg aaaccctacg ccttcaccca   1140
ccaattcctt tgcttcttca tgaaactgcg gaagaagcaa cggttaatgg ttatttcatt   1200
ccaaagcaag cgcgcgtgat gataaacgca tgggctattg aagagacgc aaattgttgg   1260
gacgaacccg agagttttaa accgtcgcgg ttttgaaac caggtgtgcc cgattttaaa   1320
gggagtaatt ttgagtttat tccgtttggg tcaggacgta gatcctgtcc cggtatgcag   1380
ttgggtttgt atgcgcttga tttggcagtg gctcatttac ttcattgctt tacttgggag   1440
ttgccggatg gaatgaaacc gagtgagatg gatatgagtg atgtatttgg actcactgca   1500
ccaagagcga gtcgactcat tgctattcct actaagcgtg tcttgtgtcc tttggattaa   1560
```

<210> SEQ ID NO 40
<211> LENGTH: 1563
<212> TYPE: DNA
<213> ORGANISM: Medicago sativa

<400> SEQUENCE: 40

```
atggattcac ttcatcaagc aaaaacaaca ctaggacaat tccaaacaac tctactatta     60
gttctcccag tcactttgtt tctactacta aatttagcat caaaatttcg taaaagagca    120
ccatatccac ctggaccaag agggttaccc ttaataggca acatgaacat gttggacaaa    180
ctcacacata gaggcttagc aaaattagca aaacaatatg gcggggtttt gcacctccgc    240
atggggttta tccacatggt ggcaatttca atcccgaagc agcgcgtgaa gtgttacaa    300
ttacacgaca gcatcttttc aaatcggcca gcgaccgtag ccataagtta cctcacttat    360
aaccgtgctg acatggcgtt cgcacactac ggtccatttt ggcgccagat gcgaaaactt    420
tgtgtcatga aactctttag ccgcaaacgt gctgagtcat ggcaatctgt taaagacgaa    480
gttgaggccg ttatcaccaa cgttaacaat aacttgggaa agtctgttaa cgttggtgag    540
ttggttttta acttgacaaa aaatattatc tatcgcgcgg cttttgggtc gtgttcaaaa    600
gaaggacaag atgagttcat ttcgatactt caagagtttt cgaaattgtt tggtgctttt    660
aatattgctg attttgttcc ttgtttgaaa tgggttgatc ctcaaggttt taatgctagg    720
cttgttaagg ctcgtggtgc gttggatggt tttattgata agattttga tgaacatgtg    780
```

```
gagaagaaga ggaatatgag tggtgattgt ggtgatgaag atagtgatat ggttgatgaa      840
ttgttggctt tttacagtga tgaagctaaa gtagataatg aatcggatga tcttcataac      900
tccatcaaac tcaccaggga taacatcaaa gccattatca tggatgtgat gttcggagga      960
acagaaacag tggcatcagc aatggaatgg gcaatgtcgg agctaatgag aaatccagaa     1020
gaactaaagc gtgtgcaaca agaaatcgcc actgtggttg gcctagaccg gcgtgtggag     1080
gaatcagaca tcgagaaact cacttatcta aagtgtgccg tcaaggagac gttgcgtctc     1140
caccctccca tccccttct cctccacgaa accgcgagg acgcgacagt tggtggttat       1200
tttgttccta agggctcgcg tgtgatgata aatgtgtggg ctataggcag agacaaagaa     1260
tcgtgggaag atccagaaga gtttaggcct tcgcgatttt tggattcaag tgcacccgat     1320
tttaaaggaa gtcattttga gtttattcca ttcggatcag gtcgaaggtc ttgccccggg     1380
atgcaattgg gcctttatgc tttggatttg gctttggccc atttacttca ttgctttact     1440
tgggagttgc ccaatgggat gaaggctagt gagatggata cgagtgatgt ttttggactc     1500
actgctccga gagcaagtcg actcattgca gttccagcta agcgtgttgt gtgccctctc     1560
tga                                                                   1563

<210> SEQ ID NO 41
<211> LENGTH: 1560
<212> TYPE: DNA
<213> ORGANISM: Medicago sativa

<400> SEQUENCE: 41
atggattctc ttctaaaata tccaatcatg gagaacttta aggaagaacc atttcttatg       60
gcaatcatgt tcatcttacc actaatactc ttgttgggtt tagtgtcacg aatcctcaaa      120
aggccaagat atccaccagg accaaaaggg ttacctgtta taggtaacat gctaatgatg      180
gaccaattaa cccaccgtgg tctagccaac ttagccaaaa aatatggagg catctttcac      240
ctacgcatgg gattcctcca catggtagct atttccgacg cagacgccgc acgacaagtt      300
ctccaagttc aagacaacat cttttccaac cggccagcaa ctgtagccat aaataccta      360 acttacgacc gtgctgacat ggcgttcgct cactacggtc ccttttggcg ccagatgcga      420
aaactttgcg tgatgaagct tttcagccgc aagcacgcag agtcttggca atctgttaga      480
gacgaggttg accatgctat ccgaactgtt tcggacaaca taggcaaccc tgtgaacatt      540
ggagaactgg tgttcaattt aactaaaaac attatatatc gagcggcttt cgggtcgagc      600
tcaagagaag acaagatga gtttattgga atattgcaag agtttccaa attgtttgga        660 gcttttaata tttccgactt tgtaccttgt tttggagcta ttgaccctca agggcttaat      720
gctaggcttg tgaaggctcg taaagatttg gatagtttca tagacaaaat catagatgaa      780
catgtgcaga agaagaaaag tgttgttgat gaagaaacgg atatggtgga tgagttgctt      840
gctttctata gtgaggaggc taaattgaat aatgaatcag atgatttgca taattccatc      900
aaacttacca aggataacat caaagccatc ataatggacg tgatgtttgg aggaacggaa      960
acggtagcat cagcaatcga atgggctatg gcagagttaa tgaaaagccc agaagatctt     1020 aaaaagtcc aacaagaact agcagaagtt gtcggcctga gccgacaggt cgaagagccc      1080
gatttcgaga aactaactta tctgaaatgc gctcttaagg aaaaccctacg tcttcaccca    1140 ccaattcctt tgcttcttca cgaaactgcg gaagaagcaa cggttaatgg ttatttcatt    1200
ccaaagcaag cgcgtgtgat gataaacgca tgggctattg gaagagacgc aaattgttgg     1260
```

| | |
|---|---|
| gaagaacccg agagttttaa gccatcacgg tttttgaaac caggtgtgcc cgattttaaa | 1320 |
| gggagtaatt ttgagtttat tccgtttggg tcaggacgta gatcctgtcc aggtatgcag | 1380 |
| ttgggtttgt acgcgcttga tttggcggta gctcatttac ttcattgctt tacttgggag | 1440 |
| ttgccggatg gaatgaaacc aagtgagatg gatatgagtg atgtatttgg actcactgct | 1500 |
| ccgagagcaa gtcgactcat tgctattcct actaagcgtg tcttgtgtcc tctggattag | 1560 |

<210> SEQ ID NO 42
<211> LENGTH: 806
<212> TYPE: DNA
<213> ORGANISM: Medicago truncatula

<400> SEQUENCE: 42

| | |
|---|---|
| ctgtcagcaa taataatact tcttgttttt tgccggtcaa attttttgtg tacataggat | 60 |
| atgttgatag gtgcaacaga tacttctgca acagcaattg agtggacaat ttcagagcta | 120 |
| ttaaaaaatc caagagttat gaaaaggtg caaaagagt tggaaatagt ggtgggtatg | 180 |
| aagagaaaag tggaggaatc agatttggag aagttggagt atttgaacat ggttataaaa | 240 |
| gaaagcctca ggtttcatcc agtggtaccc ctatcagtac cacaccaatc catgaaagat | 300 |
| tgcactgttg aagaattttt catacctaaa aactcaagga tcatggtgaa tgcatgggca | 360 |
| attatgagag atccaaattc ttggactgac cctgagaagt tttggcctga gagatttgaa | 420 |
| ggaaacaaca tagatgttgg agggcaacac tttcatctta taccatttgg ctctggaaga | 480 |
| aggggatgtc ctggattgca attaggtcta actatggtgc gtttggcggt agcccaactt | 540 |
| gtgcattgct ttgattttaa attgcctaat gatatgttac caagtgactt ggacatgaca | 600 |
| gaatcatttg gtgttactat gcctagagcc aatcatctaa ttgcaatccc tgtttatcgt | 660 |
| ctctaagtta aaaaaaaaac aaatgtagtt gacattgcaa tttatgtttg aaaaatattt | 720 |
| gtagacaaat aagttgtcat ttgttttctc aattgatttt acacataatg gagtgtgctt | 780 |
| tgaaattcaa ataatttcc tttctt | 806 |

<210> SEQ ID NO 43
<211> LENGTH: 1927
<212> TYPE: DNA
<213> ORGANISM: Medicago truncatula
<220> FEATURE:
<221> NAME/KEY: modified_base
<222> LOCATION: (1420)
<223> OTHER INFORMATION: N = A, C, G and/or T/U

<400> SEQUENCE: 43

| | |
|---|---|
| tataaaggct ccaatactct tcgctcaact cagcaacact caaatatagt tgcaagcaat | 60 |
| atcttgaaac ccaaaaaact aacgcacatc cacaatcata tagctgcata aattaacaca | 120 |
| aaaccatata tatggattcg cttctaaaat ctccaatcat ggagaacttg aaggaagaac | 180 |
| catttcttat ggcaatcatg ttcatcgtac cactaatact cttgttgggt ttagtgtcac | 240 |
| gaatcctcaa aagaccaaga tatccaccag gaccaatagg gttacctatt ataggtaaca | 300 |
| tgttaatgat ggaccaatta acccaccgtg gtctagccaa cttagcccaa aaatatggtg | 360 |
| gcatctttca cctacgcatg ggattcctcc acatggtagc tatttccgac gcggatgccg | 420 |
| cacgacaagt tctgcaagtt caagacaaca tcttttccaa ccggccagca actgtagcca | 480 |
| ttaaataccct aacttacgac cgtgctgaca tggcgtttgc tcactatggt ccctttggc | 540 |
| gccagatgcg aaaactctgc gtgatgaagc ttttcagccg taaacacgcc gagtcttggc | 600 |
| aatctgttag agacgaggtt gactatgctg tccgaactgt ttcagacaac ataggcaacc | 660 |

| | |
|---|---|
| ctgtgaacat tggagaacta gtattcaact taaccaaaaa cattatatat cgagcggctt | 720 |
| tcgggtcgag ctcgagagaa ggacaagatg agtttattgg aatattgcaa gagttttcca | 780 |
| aattgtttgg agcttttaat atttctgatt ttgtaccttg ctttggagct attgatcctc | 840 |
| aagggcttaa tgctaggctt gtgaaggctc gtaaagaatt ggatagtttc atagacaaaa | 900 |
| tcatagatga acatgtgcag aagaagaaga gtgttgttga tgaagaaacg gatatggtgg | 960 |
| atgagttgct tgctttctat agcgaggaag ctaaattgaa taatgaatca gatgatttga | 1020 |
| ataattctat caaacttacc aaggataata tcaaagccat catcatggac gtgatgtttg | 1080 |
| gaggaacgga aacggtagca tcagcaattg aatgggccat ggcagagtta atgaaaagcc | 1140 |
| cagaagacct aaagaaagtc caacaagagc tagcagaagt tgtgggcctg agccgacagg | 1200 |
| tcgaagagtc cgattttgag aaactaactt atctgaaatg cgctcttaag gaaaccctac | 1260 |
| gtcttcaccc accaattcca ttgcttcttc acgaaactgc ggaagaagca acagttaatg | 1320 |
| gttatttcat tccaaagcaa gcgcgtgtga tgataaacgc atgggctatt ggaagagatg | 1380 |
| caaattgttg ggaggaacct cagagtttta agccgtcacn ggttttgaa accaggtgtg | 1440 |
| cccgatttca aaggaagtaa ttttgagttt attccatttg ggtcaggacg tagatcctgt | 1500 |
| cccggtatgc agttgggttt gtacgcgctt gatttggcgg tagctcattt acttcattgc | 1560 |
| ttcacttggg agttgccaga tggaatgaag ccaagtgaga tggatatgag tgatgtattt | 1620 |
| ggactcactg ctccaagagc gagtcgactc gttgctatcc ctactaagcg tgtcttgtgt | 1680 |
| cctctggatt agaaagaaaa agatcaagaa aaaaaaatgg aattgagttt tctattttgg | 1740 |
| gttttcttct tttattatta ttctattaga caataagcat aagtgttttg tgatgataaa | 1800 |
| ataagacacg taacaagcac gtgagtgtgt aaaagaattg gaattttctt cacttttctt | 1860 |
| gccgtacgct tctatttca aatattataa tgtattatac tatcctataa gaaacaattc | 1920 |
| attgtat | 1927 |

<210> SEQ ID NO 44
<211> LENGTH: 1819
<212> TYPE: DNA
<213> ORGANISM: Arabidopsis thaliana

<400> SEQUENCE: 44

| | |
|---|---|
| aaaaaaaaca ctcaatatgg agtcttctat atcacaaaca ctaagcaaac tatcagatcc | 60 |
| cacgacgtct cttgtcatcg ttgtctctct tttcatcttc atcagcttca tcacacggcg | 120 |
| gcgaaggcct ccatatcctc ccggtccacg aggttggccc atcataggca acatgttaat | 180 |
| gatggaccaa ctcacccacc gtggtttagc caatttagct aaaaagtatg gcggattgtg | 240 |
| ccatctccgc atgggattcc tccatatgta cgctgtctca tcacccgagg tggctcgaca | 300 |
| agtccttcaa gtccaagaca gcgtcttctc gaaccggcct gcaactatag ctataagcta | 360 |
| tctgacttac gaccgagcgg acatggcttt cgctcactac ggaccgtttt ggagacagat | 420 |
| gagaaaagtg tgtgtcatga aggtgtttag ccgtaaaaga gctgagtcat gggcttcagt | 480 |
| tcgtgatgaa gtggacaaaa tggtccggtc ggtctcttgt aacgttggta agcctataaa | 540 |
| cgtcggggag caaattttg cactgacccg caacataact taccgggcag cgtttgggtc | 600 |
| agcctgcgag aagggacaag acgagttcat aagaatctta caagagttct ctaagctttt | 660 |
| tggagccttc aacgtagcgg atttcatacc atatttcggg tggatcgatc cgcaagggat | 720 |
| aaacaagcgg ctcgtgaagg cccgtaatga tctagacgga tttattgacg atattatcga | 780 |

```
tgaacatatg aagaagaagg agaatcaaaa cgctgtggat gatggggatg ttgtcgatac      840
cgatatggtt gatgatcttc ttgcttttta cagtgaagag gccaaattag tcagtgagac      900
agcggatctt caaaattcca tcaaacttac ccgtgacaat atcaaagcaa tcatcatgga      960
cgttatgttt ggaggaacgg aaacggtagc gtcggcgata gagtgggcct taacggagtt     1020
attacggagc cccgaggatc taaaacgggt ccaacaagaa ctcgccgaag tcgttggact     1080
tgacagacga gttgaagaat ccgacatcga aagttgact tatctcaaat gcacactcaa      1140 agaaaccta aggatgcacc caccgatccc tctcctcctc cacgaaaccg cggaggacac      1200
tagtatcgac ggtttcttca ttcccaagaa atctcgtgtg atgatcaacg cgtttgccat     1260
aggacgcgac ccaacctctt ggactgaccc ggacacgttt agaccatcga ggttttgga     1320 accgggcgta ccggatttca aagggagcaa tttcgagttt ataccgttcg ggtcgggtcg     1380
tagatcgtgc ccgggtatgc aactagggtt atacgcgctt gacttagccg tggctcatat     1440
attacattgc ttcacgtgga aattacctga tgggatgaaa ccaagtgagc tcgacatgaa     1500
tgatgtgttt ggtctcacgg ctcctaaagc cacgcggctt ttcgccgtgc caaccacgcg     1560
cctcatctgt gctcttaag tttatggttc gagtcacgtg gcaggggtt tggtatggtg      1620 aaaactgaaa agtttgaagt tgccctcatc gaggatttgt ggatgtcata tgtatgtatg    1680
tgtatacacg tgtgttctga tgaaaacaga tttggctctt tgtttgccct ttttttttt     1740 ttctttaatg gggattttcc ttgaatgaaa tgtaacagta aaaataagat ttttttcaat    1800
aagtaattta gcatgttgc                                                  1819

<210> SEQ ID NO 45
<211> LENGTH: 1873
<212> TYPE: DNA
<213> ORGANISM: Populus trichocarpa

<400> SEQUENCE: 45
ctgtgatgca cacaatacaa tacataccat agacacaaac acaaaatct gcatccatgg       60 attctcttct ccaatctttg caaactttac ccatgtcttt cttcttgatc attatctctt     120 caatttctt cttaggtcta atctctcgcc ttcgccggag atcaccatat ccaccagggc      180
ctaaagggtt tccacttatt ggtagcatgc atctgatgga ccaattaact gaccgtggct     240
tagctaaact agctaaacaa tatggtgggc tatttcatat gcgtatgggg tacttgcata    300
tggtagctgg ttcatctcct gaagtagctc gccaagtttt gcaagtccag gataacatgt    360
tctccaatag accagccaac atagccataa gctacttaac ctatgatcgt gccgatatgg   420
cctttgccca ctatggtccg ttctggcgcc agatgcgtaa gctctgcgtc atgaagctat    480
ttagccggaa aagggctgaa tcatgggagt ctgtgagaga cgaggtggac tcaatggtta   540
agacagttga atccaatata ggcaagcctg tgaacgttgg agaattgata tttacactga    600
ccatgaatat cacttataga gcagcttttg gggccaaaaa tgaaggacaa gatgagttca    660
tcaagatttt gcaggagttc tccaagcttt ttggagcatt caacatttcg gatttcattc    720
cttggcttgg ttgattgac ccccaagggc tcaccgctag acttgtcaag gctcgaaaag    780
cacttgataa attcatcgac catatcatcg atgatcatat ccaaaaaga aaacagaata    840 actactctga gaggctgaa accgatatgg ttgatgacat gctaaccttt tacagtgaag    900
agacaaaagt aaacgaatca gatgatttac aaaacgccat caaacttact agagacaaca    960
tcaaagccat catcatggat gtgatgtttg gtggacgga gacagtggcg tcggctatag    1020
agtgggccat ggcagagcta ttgaagagtc cagaagatat aaaaagagtc cagcaagagc    1080
```

```
tcgccgacgt ggttggttta gagcggcgcg tggaggaaag tgattttgat aaactaacat    1140
tcttcaaatg cacgcttaaa gaaaccttaa gacttcaccc accaatccca cttctcttac    1200
acgaaacatc tgaagatgct gaggttgctg gttattacgt tccaaaaaag acaagggtca    1260
tgatcaatgc ttatgctatt ggcagagaca agaattcatg ggaagatcct gattctttta    1320
agccttcgag gtttttggaa ccaggggtgc ctgatttcaa agggaatcac ttcgaattta    1380
ttccgttcgg gtcaggtcgg aggtcttgcc ctggcatgca actggggtta tacgcccttg    1440
atttggctgt tgctcatttg cttcattgtt ttacttggga gttgcctgat ggcatgaaac    1500
caagtgaact cgacatgact gatatgtttg gactcactgc gccaagagca actcgactcg    1560
ttgccgtccc gagaaagcgc gtggtctgtc cactttaagg aaggggaaag aaaaggtaag    1620
gaatataaat ggagggagtt tcctcaatct gtgtattcta taaataatta gggccatgtt    1680
ggagaaggtg acagcaggtg gatttgcatg ttttttcct agttttttt tttttttac      1740 tttttatata aaattgaaaa aaaaaagaga gagaataatg aagagataaa aatgggagag    1800
atcggatttt ttacttgctg aatatgttta caaagactcc aatttcattt gatttaaaaa    1860
aaaaaaaaaa aaa                                                        1873
```